(12) United States Patent
Dalbow et al.

(10) Patent No.: US 11,944,559 B2
(45) Date of Patent: Apr. 2, 2024

(54) SYSTEMS AND METHODS FOR CRIMPING AND DEVICE PREPARATION

(71) Applicant: EDWARDS LIFESCIENCES CORPORATION, Irvine, CA (US)

(72) Inventors: Brendan Michael Dalbow, Huntington Beach, CA (US); Ashley Akemi Ishigo, Torrance, CA (US); Jennifer Marie Reitmajer, Costa Mesa, CA (US); Quang Ngoc Vu, Aliso Viejo, CA (US); Gonzalo German Angelico, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/114,897

(22) Filed: Feb. 27, 2023

(65) Prior Publication Data

US 2023/0218415 A1 Jul. 13, 2023

Related U.S. Application Data

(63) Continuation of application No. PCT/US2021/042276, filed on Jul. 20, 2021.

(60) Provisional application No. 63/220,024, filed on Jul. 9, 2021, provisional application No. 63/137,658, filed (Continued)

(51) Int. Cl.
*A61F 2/24* (2006.01)
*A61F 2/95* (2013.01)

(52) U.S. Cl.
CPC .......... *A61F 2/9525* (2020.05); *A61F 2/2418* (2013.01); *A61F 2/2433* (2013.01); *A61F 2/9524* (2020.05)

(58) Field of Classification Search
CPC .... A61F 2/9525; A61F 2/2418; A61F 2/2433; A61F 2/9524
See application file for complete search history.

(56) References Cited

U.S. PATENT DOCUMENTS

| 519,297 | A | 5/1894 | Bauer |
| 1,438,681 | A | 12/1922 | Bath |
| 1,493,515 | A | 5/1924 | Berthold |

(Continued)

FOREIGN PATENT DOCUMENTS

| DE | 19532846 A1 | 3/1997 |
| DE | 19907646 A1 | 8/2000 |

(Continued)

*Primary Examiner* — Suzette J Gherbi
(74) *Attorney, Agent, or Firm* — Klarquist Sparkman, LLP; Sean Seung Kyu Kim

(57) ABSTRACT

Apparatuses, systems, and methods for crimping prosthetic implants onto a delivery apparatus are disclosed. In some examples, a support body for a prosthetic heart valve can comprise a first portion comprising an alignment device configured to couple with a crimping device, and a second portion comprising a support surface that tapers from a wider end disposed adjacent the first portion to a narrower end, where the support surface is configured to receive the prosthetic heart valve thereon and hold one or more leaflets of the prosthetic heart valve in an open position. The support body can further comprise a central channel extending through the first portion and the second portion, the central channel configured to receive a delivery apparatus for the prosthetic heart valve therethrough.

6 Claims, 34 Drawing Sheets

Related U.S. Application Data on Jan. 14, 2021, provisional application No. 63/072,444, filed on Aug. 31, 2020.

(56) References Cited

U.S. PATENT DOCUMENTS

| | | |
|---|---|---|
| 2,079,498 A | 5/1937 | Douglas |
| 2,664,996 A | 1/1954 | Andrews |
| 2,787,925 A | 4/1957 | Buchanan et al. |
| 2,974,367 A | 3/1961 | Doering et al. |
| 3,154,978 A | 11/1964 | Baker |
| 3,307,451 A | 3/1967 | Schuetz |
| 3,417,598 A | 12/1968 | Valente |
| 3,695,087 A | 10/1972 | Tuberman |
| 4,035,849 A | 7/1977 | Angell et al. |
| 4,308,744 A | 1/1982 | Baker |
| 4,350,036 A | 9/1982 | Valente |
| 4,454,657 A | 6/1984 | Yasumi |
| 4,578,982 A | 4/1986 | Schrock |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,261,263 A | 11/1993 | Whitesell |
| 5,266,073 A | 11/1993 | Wall |
| 5,325,845 A | 7/1994 | Adair |
| 5,358,496 A | 10/1994 | Ortiz et al. |
| 5,411,521 A | 5/1995 | Putnam et al. |
| 5,411,552 A | 5/1995 | Andersen et al. |
| 5,437,083 A | 8/1995 | Williams et al. |
| 5,554,185 A | 9/1996 | Block et al. |
| 5,591,195 A | 1/1997 | Taheri et al. |
| 5,599,305 A | 2/1997 | Hermann et al. |
| 5,626,604 A | 5/1997 | Cottone, Jr. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,749,921 A | 5/1998 | Lenker et al. |
| 5,782,809 A | 7/1998 | Umeno et al. |
| 5,810,873 A | 9/1998 | Morales |
| 5,824,044 A | 10/1998 | Quiachon et al. |
| 5,836,952 A | 11/1998 | Davis et al. |
| 5,840,081 A | 11/1998 | Andersen et al. |
| 5,893,852 A | 4/1999 | Morales |
| 5,908,405 A | 6/1999 | Imran et al. |
| 5,913,871 A | 6/1999 | Werneth et al. |
| 5,916,147 A | 6/1999 | Boury |
| 5,918,511 A | 7/1999 | Sabbaghian et al. |
| 5,944,690 A | 8/1999 | Falwell et al. |
| 5,951,540 A | 9/1999 | Verbeek |
| 5,961,536 A | 10/1999 | Mickley et al. |
| 5,968,068 A | 10/1999 | Dehdashtian et al. |
| 5,992,000 A | 11/1999 | Humphrey et al. |
| 6,007,543 A | 12/1999 | Ellis et al. |
| 6,009,614 A | 1/2000 | Morales |
| 6,019,777 A | 2/2000 | Mackenzie |
| 6,027,510 A | 2/2000 | Alt |
| 6,033,381 A | 3/2000 | Kontos |
| 6,051,002 A | 4/2000 | Morales |
| 6,074,381 A | 6/2000 | Dinh et al. |
| 6,082,990 A | 7/2000 | Jackson et al. |
| 6,125,523 A | 10/2000 | Brown et al. |
| 6,143,016 A | 11/2000 | Bleam et al. |
| 6,162,208 A | 12/2000 | Hipps |
| 6,167,605 B1 | 1/2001 | Morales |
| 6,168,614 B1 | 1/2001 | Andersen et al. |
| 6,174,327 B1 | 1/2001 | Mertens et al. |
| 6,176,116 B1 | 1/2001 | Wilhelm et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,309,383 B1 | 10/2001 | Campbell et al. |
| 6,352,547 B1 | 3/2002 | Brown et al. |
| 6,360,577 B2 | 3/2002 | Austin |
| 6,364,870 B1 | 4/2002 | Pinchasik |
| 6,379,372 B1 | 4/2002 | Dehdashtian et al. |
| 6,383,171 B1 | 5/2002 | Gifford et al. |
| 6,387,117 B1 | 5/2002 | Arnold, Jr. et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,558,418 B2 | 5/2003 | Carpentier et al. |
| 6,579,305 B1 | 6/2003 | Lashinski |
| 6,582,462 B1 | 6/2003 | Andersen et al. |
| 6,618,921 B1 | 9/2003 | Thornton |
| 6,629,350 B2 | 10/2003 | Motsenbocker |
| 6,651,478 B1 | 11/2003 | Kokish |
| 6,652,578 B2 | 11/2003 | Bailey et al. |
| 6,682,553 B1 | 1/2004 | Webler, Jr. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,769,161 B2 | 8/2004 | Brown et al. |
| 6,823,576 B2 | 11/2004 | Austin |
| 6,830,584 B1 | 12/2004 | Seguin |
| 6,840,081 B2 | 1/2005 | Kokish |
| 6,889,579 B1 | 5/2005 | Brown |
| 6,893,460 B2 | 5/2005 | Spenser et al. |
| 6,908,481 B2 | 6/2005 | Cribier |
| 6,915,560 B2 | 7/2005 | Austin |
| 6,920,674 B2 | 7/2005 | Thornton |
| 6,925,847 B2 | 8/2005 | Motsenbocker |
| 6,931,899 B2 | 8/2005 | Goff et al. |
| 6,968,607 B2 | 11/2005 | Motsenbocker |
| 6,988,881 B2 | 1/2006 | Votsenbocker et al. |
| 7,010,953 B2 | 3/2006 | Stupecky |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,021,114 B2 | 4/2006 | Perreault |
| 7,069,794 B2 | 7/2006 | Motsenbocker et al. |
| 7,096,554 B2 | 8/2006 | Austin et al. |
| 7,137,993 B2 | 11/2006 | Acosta et al. |
| 7,143,625 B2 | 12/2006 | Edin |
| 7,152,452 B2 | 12/2006 | Kokish |
| 7,207,204 B2 | 4/2007 | Weber et al. |
| 7,225,518 B2 | 6/2007 | Eidenschink et al. |
| 7,276,084 B2 | 10/2007 | Yang et al. |
| 7,284,401 B2 | 10/2007 | Larson et al. |
| 7,318,278 B2 | 1/2008 | Zhang et al. |
| 7,320,702 B2 | 1/2008 | Hammersmark et al. |
| 7,320,704 B2 | 1/2008 | Ashinski et al. |
| 7,374,571 B2 | 5/2008 | Pease et al. |
| 7,389,670 B1 | 6/2008 | Kokish et al. |
| 7,393,360 B2 | 7/2008 | Spenser et al. |
| 7,415,861 B2 | 8/2008 | Sokel |
| 7,435,257 B2 | 10/2008 | Lashinski et al. |
| 7,487,579 B2 | 2/2009 | Eidenschink et al. |
| 7,510,575 B2 | 3/2009 | Spenser et al. |
| 7,530,253 B2 | 5/2009 | Spenser et al. |
| 7,585,321 B2 | 9/2009 | Cribier |
| 7,587,801 B2 | 9/2009 | Austin |
| 7,594,926 B2 | 9/2009 | Linder et al. |
| 7,597,709 B2 | 10/2009 | Goodin |
| 7,618,446 B2 | 11/2009 | Andersen et al. |
| 7,628,051 B1 | 12/2009 | Kokish et al. |
| 7,780,723 B2 | 8/2010 | Taylor |
| 7,785,366 B2 | 8/2010 | Maurer et al. |
| 7,892,201 B1 | 2/2011 | Laguna et al. |
| 7,895,876 B2 | 3/2011 | Spenser et al. |
| 7,959,661 B2 | 6/2011 | Hijlkema et al. |
| 7,967,138 B2 | 6/2011 | Ryan et al. |
| 8,006,535 B2 | 8/2011 | Righini et al. |
| 8,029,556 B2 | 10/2011 | Rowe |
| 8,112,857 B2 | 2/2012 | Voelkl |
| 8,167,932 B2 | 5/2012 | Bourang et al. |
| 8,312,614 B2 | 11/2012 | Sokel |

(56) References Cited

U.S. PATENT DOCUMENTS

| | | | |
|---|---|---|---|
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2* | 6/2015 | Le | A61M 25/01 |
| 9,119,716 B2 | 9/2015 | Lee et al. | |
| 9,795,477 B2 | 10/2017 | Tran et al. | |
| 11,026,788 B2* | 6/2021 | Metchik | A61F 2/2433 |
| 11,273,038 B2 | 3/2022 | Tang et al. | |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2003/0192164 A1 | 10/2003 | Austin | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1* | 9/2005 | Forster | A61F 2/2427 623/2.11 |
| 2005/0203617 A1 | 9/2005 | Forster et al. | |
| 2005/0245894 A1 | 11/2005 | Zadno-Azizi | |
| 2006/0025857 A1 | 2/2006 | Bergheim et al. | |
| 2006/0213049 A1 | 9/2006 | Serrano et al. | |
| 2006/0282150 A1 | 12/2006 | Olson et al. | |
| 2007/0005131 A1 | 1/2007 | Taylor | |
| 2007/0056346 A1 | 3/2007 | Spenser et al. | |
| 2007/0061009 A1 | 3/2007 | Spenser et al. | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock, Jr. | |
| 2009/0043249 A1 | 2/2009 | Sokel | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1* | 11/2009 | Le | A61F 2/2433 623/2.11 |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2010/0292780 A1 | 11/2010 | Straubinger et al. | |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0123529 A1 | 5/2012 | Levi et al. | |
| 2012/0239142 A1 | 9/2012 | Liu et al. | |
| 2013/0030519 A1 | 1/2013 | Tran et al. | |
| 2013/0317598 A1 | 11/2013 | Rowe et al. | |
| 2014/0296962 A1 | 10/2014 | Cartledge et al. | |
| 2017/0049567 A1* | 2/2017 | Metchik | A61F 2/2433 |
| 2017/0065415 A1 | 3/2017 | Rupp et al. | |
| 2018/0153675 A1 | 6/2018 | Maimon et al. | |
| 2018/0344456 A1 | 12/2018 | Barash et al. | |
| 2020/0360134 A1* | 11/2020 | Peterson | A61F 2/2433 |
| 2021/0030533 A1* | 2/2021 | Tamir | A61L 2/0094 |
| 2021/0290386 A1* | 9/2021 | Metchik | A61F 2/2433 |
| 2022/0338889 A1* | 10/2022 | Sirhan | A61M 25/1011 |
| 2023/0190456 A1* | 6/2023 | Bialas | A61F 2/24 623/2.1 |
| 2023/0190464 A1* | 6/2023 | Murad | A61F 2/2436 623/2.11 |
| 2023/0190465 A1* | 6/2023 | Murad | A61M 25/10 623/2.11 |
| 2023/0190466 A1* | 6/2023 | Bialas | A61M 25/10 623/2.11 |
| 2023/0210657 A1* | 7/2023 | Murad | A61F 2/2418 623/2.11 |

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 | 6/2003 |
| WO | 2004019825 A1 | 3/2004 |
| WO | 2005084595 A1 | 9/2005 |
| WO | 2005102015 A2 | 11/2005 |
| WO | 2006032051 A2 | 3/2006 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2010121076 A2 | 10/2010 |

* cited by examiner

SYSTEMS AND METHODS FOR CRIMPING AND DEVICE PREPARATION

CROSS-REFERENCE TO RELATED APPLICATIONS

This application is a continuation of PCT Application No. PCT/US2021/042276, filed Jul. 20, 2021, which claims the benefit of U.S. Provisional Application Nos. 63/072,444, filed Aug. 31, 2020, 63/137,658, filed Jan. 14, 2021, and 63/220,024, filed Jul. 9, 2021, the entire contents of each of which are incorporated by reference herein.

BACKGROUND

Field

Certain embodiments disclosed herein may relate to apparatuses, systems, and methods for crimping implants. The systems in certain embodiments may be for use in crimping a prosthetic implant. Certain embodiments disclosed herein may relate to apparatuses, systems, and methods for device preparation.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life-threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. A delivery apparatus may be provided to deploy such an implant to the desired location in the human body. The implant may be in a compressed state when coupled to the delivery apparatus, and thus must be compressed for delivery to the desired location of implantation within the patient's body.

Such implants may be self-expandable, or balloon-expandable, or may be mechanically expandable. Balloon-expandable prosthetic valves are typically crimped from an initial large diameter to a smaller diameter prior to advancement to a treatment site in a body. Before crimping, a balloon expandable prosthetic valve is typically placed over an inflatable balloon on a catheter shaft. Once delivered to the implantation site, the balloon can be inflated to expand the prosthetic valve to its functional size. Self-expanding prosthetic implants are typically also crimped to a smaller diameter, but are then inserted into a sheath. After placement in the body, the sheath is retracted, and the prosthetic valve expands inside the body. Mechanically expandable prosthetic implants may also be crimped to a smaller diameter.

Methods exist to crimp such implants prior to delivery, however, it may be desirable to provide improved apparatuses, systems, and methods for use in crimping and other device preparation.

SUMMARY

Embodiments of the present disclosure may be directed to apparatuses, systems, and methods for use in crimping an implant, and other apparatuses, systems, and methods for device preparation. The apparatuses, systems, and methods disclosed herein may be directed to more accurately positioning an implant upon a delivery apparatus and more effectively crimping the implant to the delivery apparatus. Certain features disclosed herein may be directed to improving the functioning of the implant following deployment, including a reduced possibility of damage to the implant during the crimping process. Other features may be directed to improved methods of bending or otherwise positioning an elongate shaft of a delivery apparatus during a crimping procedure, or during another device preparation procedure.

One or more embodiments of the present disclosure include a system for use in crimping a prosthetic implant having one or more leaflets to a delivery apparatus. The system may include a support body configured to be inserted into a crimping device and having a support surface configured to be positioned between the one or more leaflets and the delivery apparatus and for supporting the one or more leaflets in an open position.

One or more embodiments of the present disclosure include a system for use in crimping a prosthetic implant having one or more leaflets to a delivery apparatus. The system may include a ring body including one or more indicators indicating a rotational position of the prosthetic implant relative to the ring body.

One or more embodiments of the present disclosure include a method. The method may include positioning a delivery apparatus within a channel of a crimping device including one or more pressing surfaces configured to radially compress a prosthetic implant within the channel.

The method may include positioning the prosthetic implant within the channel and around the delivery apparatus, the prosthetic implant including one or more leaflets. The method may include positioning a support body within the channel and between the one or more leaflets and the delivery apparatus.

The method may include supporting the one or more leaflets in an open position with the support body. The method may include crimping the prosthetic implant to the delivery apparatus utilizing the one or more pressing surfaces of the crimping device.

One or more embodiments of the present disclosure include a system for use in crimping a prosthetic implant having one or more leaflets to a delivery apparatus. The system may include a stopper housing including a cavity configured to receive a portion of the delivery apparatus distal of an implant retention area of the delivery apparatus and including a contact surface configured to abut the delivery apparatus to impede axially distal movement of the delivery apparatus when the delivery apparatus is positioned within a crimping device configured to crimp the prosthetic implant to the delivery apparatus.

One or more embodiments of the present disclosure include a method. The method may include positioning a delivery apparatus within a channel of a crimping device including one or more pressing surfaces configured to radially compress a prosthetic implant within the channel. The method may include positioning the prosthetic implant within the channel and around the delivery apparatus.

The method may include abutting a portion of the delivery apparatus distal of an implant retention area of the delivery apparatus against a stopper housing to define a position of the delivery apparatus within the channel of the crimping device. The method may include crimping the prosthetic implant to the delivery apparatus utilizing the one or more pressing surfaces of the crimping device.

One or more embodiments of the present disclosure include a system for use in crimping a prosthetic implant having one or more leaflets to a delivery apparatus. The system may include a spacer body configured to extend over a portion of the delivery apparatus distal of an implant retention area of the delivery apparatus, and including a contact surface for a distal end of the prosthetic implant to abut to define a position of the prosthetic implant upon the delivery apparatus.

One or more embodiments of the present disclosure include a method. The method may include positioning a spacer body over a portion of a delivery apparatus distal of an implant retention area of the delivery apparatus. The method may include positioning a prosthetic implant over the delivery apparatus.

The method may include abutting a distal end of the prosthetic implant against a contact surface of the spacer body to define a position of the prosthetic implant upon the delivery apparatus. The method may include crimping the prosthetic implant to the delivery apparatus at the position.

One or more embodiments of the present disclosure include a system. The system may include an elongate body including a channel for receiving an elongate shaft of a delivery apparatus having a proximal portion and a distal portion, the elongate body configured to bend in at least one plane to move the distal portion of the delivery apparatus proximate the proximal portion of the delivery apparatus.

One or more embodiments of the present disclosure include a method. The method may include bending an elongate body that includes a channel receiving an elongate shaft of a delivery apparatus in at least one plane to bend the elongate shaft such that a distal portion of the delivery apparatus is positioned proximate a proximal portion of the delivery apparatus.

One or more embodiments of the present disclosure include a crimping system for a prosthetic implant. The crimping system may include a plurality of elongate strands each having a first end and a second end and arranged to form an elongate tube extending around an axis and surrounding a channel configured to receive the prosthetic implant and having a central portion with an interior diameter. The crimping system may include a first support body coupled to the first end of each of the plurality of elongate strands. The crimping system may include a second support body coupled to the second end of each of the plurality of elongate strands and configured to rotate about the axis relative to the first support body to reduce the interior diameter and compress the prosthetic implant within the channel.

One or more embodiments of the present disclosure include a method. The method may include positioning a prosthetic implant within a channel of a crimping device. The crimping device may include a plurality of elongate strands each having a first end and a second end and arranged to form an elongate tube extending around an axis and surrounding the channel and having a central portion with an interior diameter, a first support body coupled to the first end of each of the plurality of elongate strands, and a second support body coupled to the second end of each of the plurality of elongate strands. The method may include rotating the second support body about the axis relative to the first support body to reduce the interior diameter and compress the prosthetic implant within the channel.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
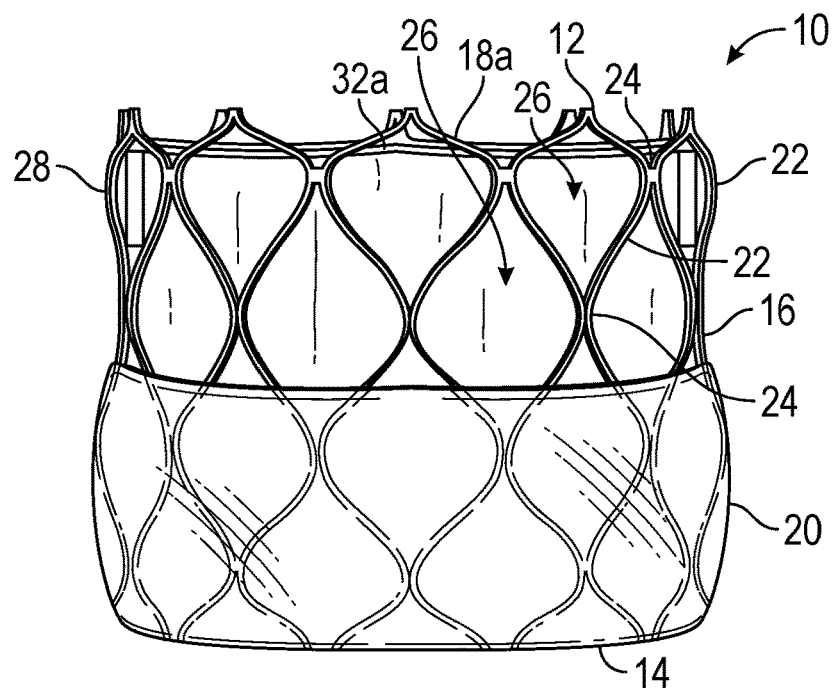
FIG. 1 illustrates a side perspective view of a prosthetic implant according to an embodiment of the present disclosure.

FIG. 1 illustrates a perspective view of a prosthetic implant 10 in the form of a replacement heart valve. The prosthetic implant 10 may be configured to be deployed within a portion of a patient's body. The prosthetic implant 10, for example, may be deployed within a native heart valve annulus, which may comprise a native aortic valve, or in embodiments may comprise a native mitral, tricuspid, or pulmonary valve. In embodiments, the implant 10 may have other forms, and may comprise a stent or other form of medical implant as desired.

The prosthetic implant 10 may include a proximal end 12 and a distal end 14, and a length therebetween. The prosthetic implant 10 may include a body in the form of a frame 16. The prosthetic implant 10 may further include one or more of a plurality of leaflets 18a-c coupled to the frame 16 and may include a skirt 20 covering an outer surface of a distal portion of the frame 16.

The frame 16 may comprise a plurality of struts 22 connected at junctures 24. A plurality of openings 26 may be positioned between the struts 22. The openings 26 may be configured to reduce the overall weight of the frame 16, and also allow the frame 16 to be compressed to reduce a diameter of the frame 16 and be expanded to increase a diameter of the frame 16. The frame 16 may be configured to be radially compressed and axially lengthened while being radially compressed. The struts 22 may be configured such that as the frame 16 is compressed to reduce a diameter of the frame 16, the length of the frame 16 may increase. Also, as the frame 16 is expanded to increase the diameter of the frame 16, the length of the frame 16 may decrease. The frame 16 may be compressed in a variety of manners, including use of a crimping device, and may be expanded in a variety of manners, including being expanded with a balloon, being self-expandable, or being mechanically expandable. Embodiments herein may refer to a balloon expandable implant, yet self-expandable implants or mechanically expandable implants may be utilized as well.

The frame 16 may include an outer surface 28 configured to be pressed against interior vasculature of a patient's body. For example, as the frame 16 is expanded, the outer surface 28 may contact and press against the interior vasculature of the patient's body. The outer surface 28 may press against a native annulus, or native leaflets of a heart valve in embodiments. The frame 16 may include an interior surface 30 (marked in FIG. 2) configured to face opposite the outer surface 28 and configured to face towards a flow channel of the implant 10.

The skirt 20 may cover the outer surface 28 of the distal portion of the frame 16 as shown in FIG. 1 and may comprise a membrane or other form of skirt 20. The skirt 20 may improve compliance of the frame 16 with a native valve in which the implant 10 is implanted and may be utilized to couple the leaflets 18a-c to the frame 16 via sutures of another form of coupler.

Figure 2:
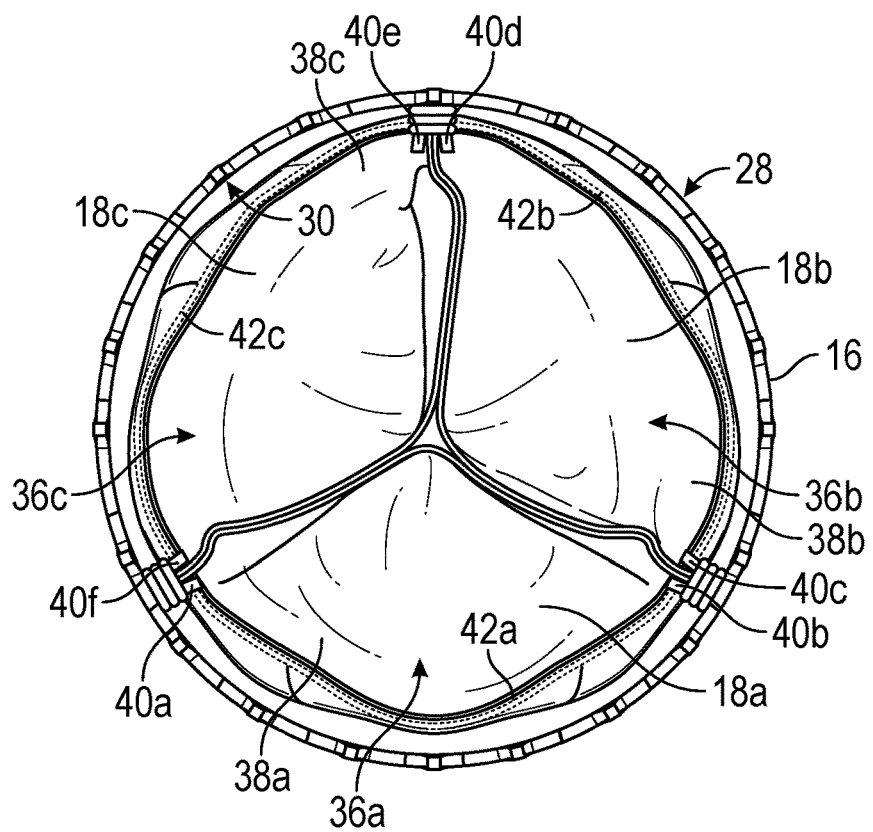
FIG. 2 illustrates a top view of the prosthetic implant shown in FIG. 1 with the leaflets of the implant in a closed position.
Figure 3:
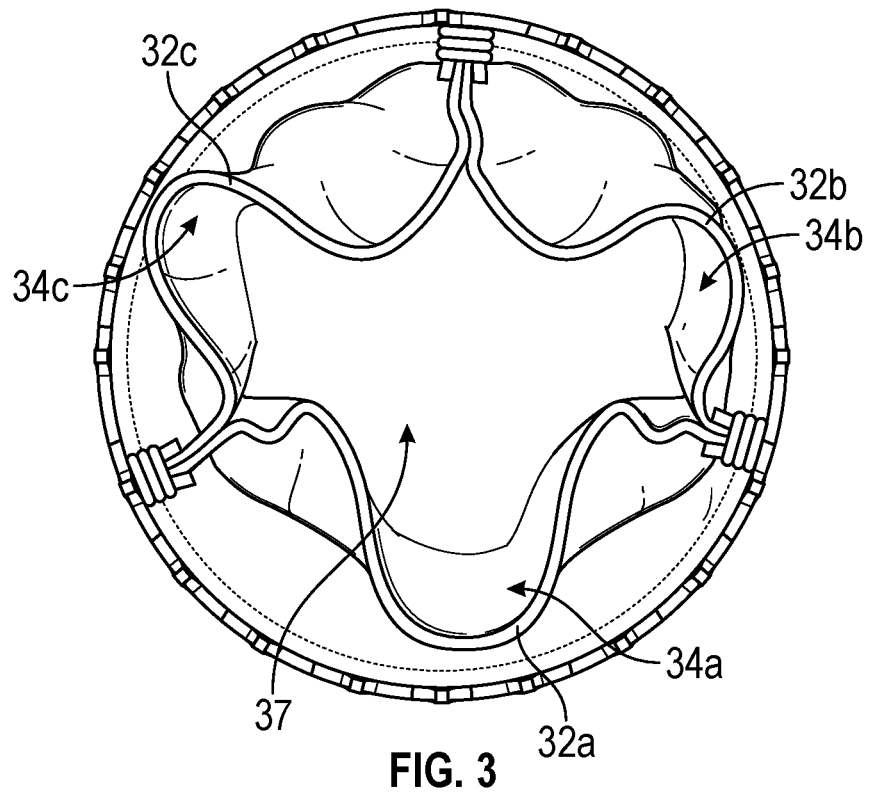
FIG. 3 illustrates a top view of the prosthetic implant shown in FIG. 1 with the leaflets of the implant in an open position.

The plurality of leaflets 18a-c (more clearly shown in FIG. 2) may extend inward from the interior surface 30 of the frame 16. The plurality of leaflets 18a-c may be configured to move towards each other to move to a closed position (as shown in FIG. 2) and be moved away from each other to move to an open position (as shown in FIG. 3). The leaflets 18a-c may each include upper end portions 32a-c (marked in FIG. 3) that are configured to contact each other to close the flow channel of the implant 10 when the leaflets 18a-c are in the closed position. The upper end portions 32a-c are configured to move away from each other to open the flow channel of the implant 10 when the leaflets 18a-c are in the open position. The leaflets 18a-c may move back and forth between open and closed positions or states or configurations to replicate the motion of a native valve.

Each leaflet 18a-c may include an interior surface 34a-c (marked in FIG. 3) configured to face towards the flow channel of the implant 10, and an exterior surface 36a-c (marked in FIG. 2) facing opposite the interior surface 34a-c and facing away from the flow channel 37 of the implant 10. Portions of the interior surface 34a-c of respective leaflets 18a-c may contact each other when the leaflets 18a-c move to the closed position.

Each leaflet 18a-c may include a respective outer portion 38a-c (marked in FIG. 2) that couples to the frame 16 of the implant 10. The coupling may have a variety of forms. For example, each leaflet 18a-c may include tabs 40a-f at the respective outer portion 38a-c of the leaflet 18a-c. The tabs 40a, b may extend from the leaflet 18a, the tabs 40c, d may extend from the leaflet 18b, and the tabs 40e, f may extend from the leaflet 18c. The tabs 40a-f may extend through openings in the frame 16 to couple to the frame 16 and then may be sutured to hold the tabs 40a-f in position. The tabs 40a-f may form commissures of adjacent leaflets 18a-c.

Further, the outer portion 38a-c of each leaflet 18a-c may be sutured to the skirt 20 along a suture line 42a-c. For example, a lower end portion of each leaflet 18a-c opposite the upper end portion 32a-c may be sutured to the skirt 20 at a respective suture line 42a-c. The sutures of the suture line 42a-c may hold the leaflets 18a-c to the frame 16 and prevent undesired fluid flow through the implant 10 outside of the flow channel 37.

The leaflets 18a-c may be configured to open and close during operation such that the proximal end 12 of the implant 10 forms an outflow end of the implant 10, and the distal end 14 of the implant 10 forms an inflow end of the implant 10. The leaflets 18a-c may be configured to impede fluid flow in an opposite direction from the outflow end to the inflow end of the implant 10 when the leaflets 18a-c are in a closed position.

In embodiments, other forms of implants may be utilized, such as stents or other forms of medical devices. The configuration of the implant shown in FIGS. 1-3 may be varied in embodiments.

Figure 4:
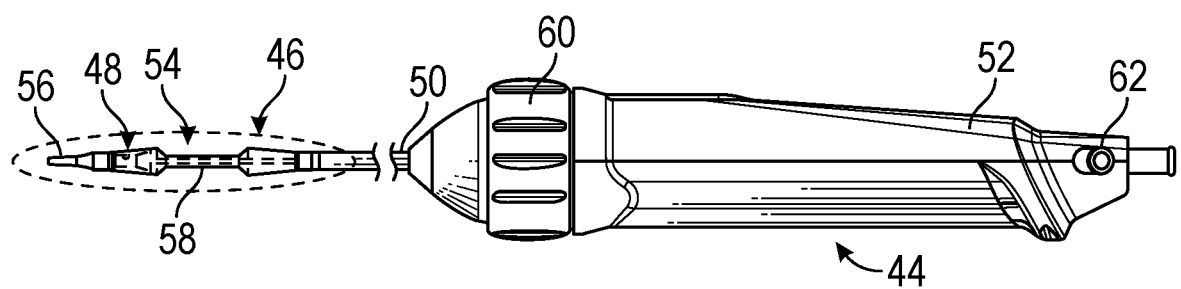
FIG. 4 illustrates a side view of a delivery apparatus according to an embodiment of the present disclosure.

The implant 10 may be configured to be delivered to an implantation site utilizing a delivery apparatus. FIG. 4, for example, illustrates an embodiment of a delivery apparatus 44 that may be utilized to deliver the implant 10 to a desired implantation site. The delivery apparatus 44 may include an elongate shaft 46 having a distal portion 48 and a proximal portion 50. The proximal portion 50 may couple to a housing in the form of a handle 52. The distal portion 48 may include an implant retention area 54 and a distal tip that may include a nose cone 56. The distal portion 48 may further include an inflatable body in the form of a balloon 58. The delivery apparatus 44 may be configured to be positioned within a crimping device to crimp the implant 10 to the implant retention area 54. The elongate shaft 46 may be positioned within the crimping device. The balloon 58 may be configured for the implant 10 to be crimped upon.

The handle 52 may be configured for a user to grip to operate the delivery apparatus 44 and to maneuver the delivery apparatus 44 through the vasculature of the patient's body. For example, the handle 52 may be moved distally to advance the elongate shaft 46 distally within the patient's body and may be moved proximally to retract the elongate shaft 46 proximally within the patient's body. As such, the implant retention area 54 and accordingly the implant 10 may be moved and positioned with the operation of the handle 52.

A control mechanism 60 may further be coupled to the handle 52. The control mechanism 60 may be configured to be operated to bend the elongate shaft 46 as desired. For example, one or more pull tethers may extend along the elongate shaft 46 and operation of the control mechanism 60 may push or pull the one or more pull tethers to cause the elongate shaft 46 to bend. The bending of the elongate shaft 46 accordingly may be controlled by the control mechanism 60. As shown in FIG. 4, the control mechanism 60 may comprise a rotatable body in the form of a control knob that may be rotated to push or pull the pull tether and cause the elongate shaft 46 to bend. Other forms of control mechanisms may be utilized as desired.

A fluid port 62 may further be coupled to the handle 52 and may be utilized to transfer fluid to and from the balloon 58 as desired. The configuration of the handle 52 may be varied in other embodiments as desired.

Figure 5:
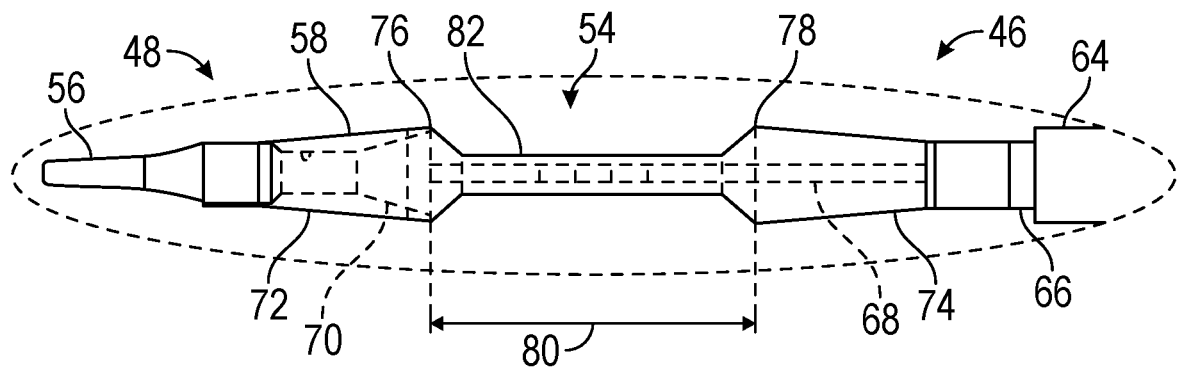
FIG. 5 illustrates a detail view of a portion of a delivery apparatus according to an embodiment of the present disclosure.

FIG. 5 illustrates a close up view of the distal portion 48 of the elongate shaft 46. The elongate shaft 46 may include one or more shafts, which may include one or more sheaths extending over each other. For example, the elongate shaft 46 may include an outer sheath 64 that may be configured to extend over and be slidable relative to a mid shaft or intermediate sheath 66 that may comprise a shaft interior of the outer sheath 64 (within the lumen of the outer sheath 64). The intermediate sheath 66 may extend over an interior shaft 68 that may extend to the nose cone 56 of the elongate shaft 46. The interior shaft 68 may be surrounded by the balloon 58. The interior shaft 68 in embodiments may include a fluid conduit that may allow fluid to be passed into and out of the balloon 58 for inflating and deflating the balloon 58 respectively. Other shafts may include one or more fluid conduits for inflating and deflating the balloon 58 as desired.

The interior shaft 68 may further comprise a distal shoulder 70 that may be positioned distal of the implant retention area 54. The distal shoulder 70 comprises a portion of the delivery apparatus 44 positioned distal of the implant retention area 54, along with other portions such as the distal tip including a nose cone 56 and a distal end 72 of the balloon 58. The distal shoulder 70 may protrude radially outward from the interior shaft 68 and may have a conical shape as desired. The taper of the conical shape may be configured such that the size of the distal shoulder 70 increases in a direction towards the implant retention area 54. The distal shoulder 70 may be configured to protect an implant 10 positioned within the implant retention area 54 as the elongate shaft 46 is advanced through the patient's body. For example, an outer diameter of the distal shoulder 70 may be at or greater than a diameter of the implant 10 when the implant 10 is in a crimped state, thus shielding the leading edge (such as the distal end 14 of the implant 10) from contacting a portion of the patient's body or snagging or snaring on a sheath that the elongate shaft 46 may be advanced through.

The balloon 58 may have a distal end 72 and a proximal end 74, and may extend over the interior shaft 68 and the distal shoulder 70. The distal end 72 may couple to the nose cone 56 and the proximal end 74 may couple to the intermediate sheath 66. The balloon 58 may extend along the length of the interior shaft 68 and may encircle the interior shaft 68. The balloon 58 is shown in a deflated state in FIG. 5, and may have a distal shoulder 76 and a proximal shoulder 78. The implant retention area 54 may have a length 80 between the distal shoulder 76 and the proximal shoulder 78. The balloon 58 may include an intermediate portion 82 between the distal shoulder 76 and the proximal shoulder 78 that may have a diameter that is less than the diameter of the distal shoulder 76 and the proximal shoulder 78. The diameter of the intermediate portion 82 may be constant in embodiments as desired.

Notably, in embodiments, the proximal shoulder 78 of the balloon 58 may be shaped as a shoulder without extending over a shoulder of the interior shaft 68. As such, the interior shaft 68 may lack an interior proximal shoulder in embodiments.

In embodiments, the interior shaft 68 may include a shoulder that is proximal of the implant retention area 54. The proximal shoulder 78 of the balloon 58 may extend over the proximal shoulder of the interior shaft 68 in such an embodiment.

The implant retention area 54 may be configured for the implant 10 to be crimped over the balloon 58 and positioned in the intermediate portion 82 between the distal shoulder 76 and the proximal shoulder 78 of the balloon 58. The implant 10 may be positioned proximal of the distal shoulder 76 and crimped in such a position. In certain embodiments, the outer sheath 64 may be advanced distally to cover the implant 10 positioned within the implant retention area 54 when the implant 10 is crimped. In certain embodiments, the outer sheath 64 may be advanced distally relative to the intermediate sheath 66 to abut a proximal edge (or the proximal end 12) of the implant 10.

In embodiments, the configuration of the delivery apparatus may be varied from the configuration shown in FIGS. 4 and 5.

Figure 6:
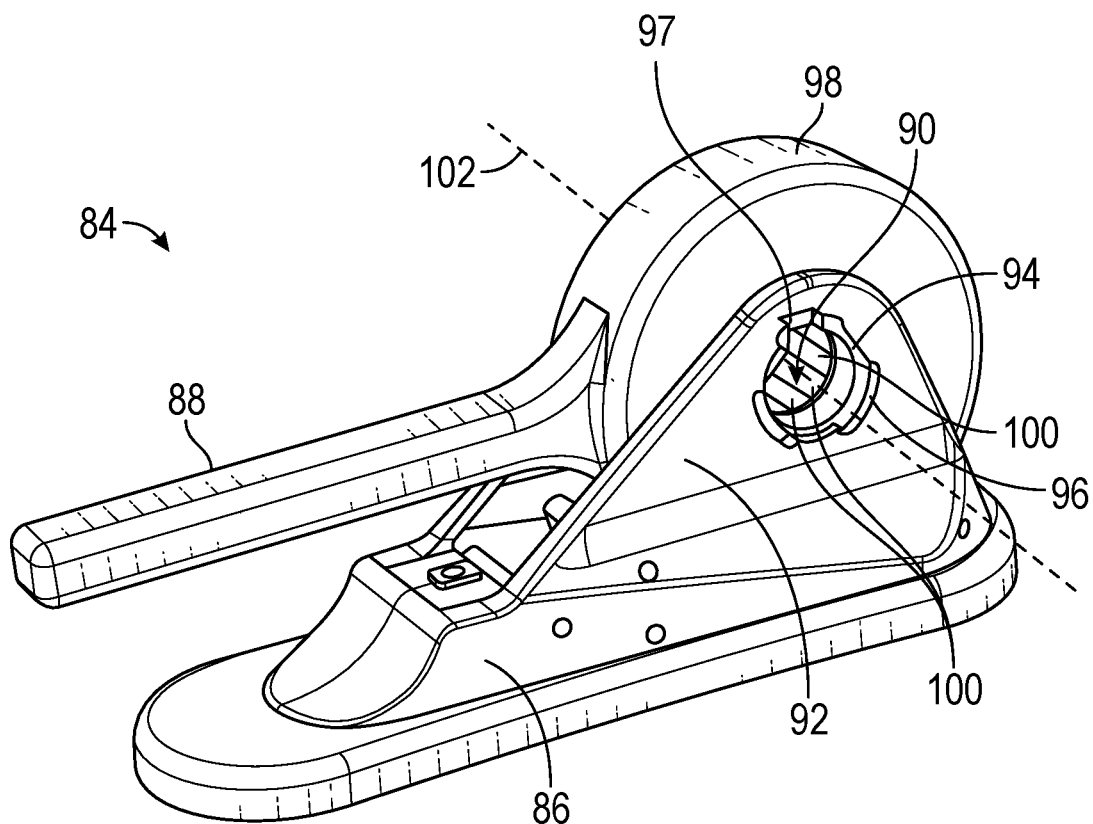
FIG. 6 illustrates a rear perspective view of a crimping device according to an embodiment of the present disclosure.
Figure 16:
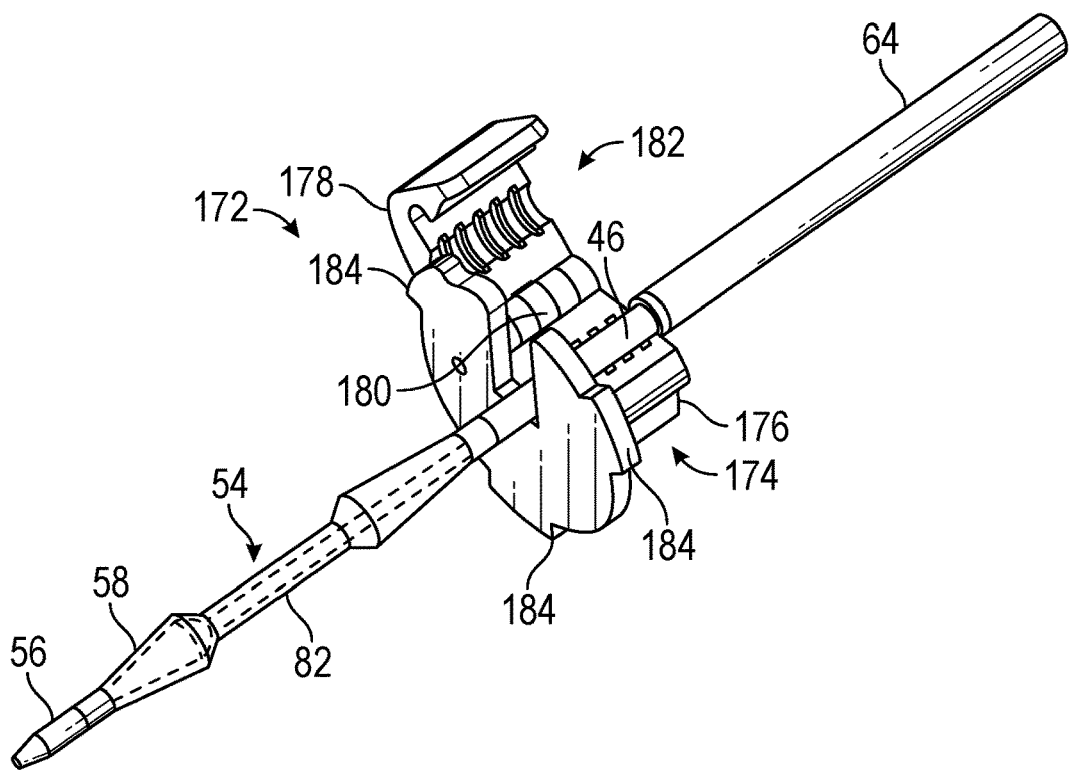
FIG. 16 illustrates a perspective view of a positioning device positioned upon a delivery apparatus according to an embodiment of the present disclosure.

The implant 10 may be crimped to the implant retention area 54 in a variety of manners. FIG. 6, for example, illustrates a rear perspective view of a crimping device 84 (or a view from the proximal side of the crimping device 84). The crimping device 84 may include a base 86, an actuator in the form of a handle 88, and a channel 90 for the implant 10 and the delivery apparatus 44 to be inserted into. The crimping device 84 may include a proximal face 92 including a proximal opening 94 that leads into the channel 90. The proximal opening 94 may be configured for the delivery apparatus 44 to be inserted into the channel 90 through. The proximal face 92 may further include mating structures 96 in the form of cut-outs that may be configured to mate with a positioning device 172, for example as shown in FIG. 16. The proximal face 92 may further include a cut out portion 97 that may be configured to receive an alignment device of a support body as disclosed herein. The cut out portion 97 may be configured as a notch or other shape in the proximal face 92.

The crimping device 84 may further include a rotatable body 98 configured to be rotated with rotation of the handle 88. The crimping device 84 may operate by a plurality of pressing surfaces 100 surrounding the channel 90 and being configured to apply a compressive force to radially compress an implant 10 positioned within the channel 90. The pressing surfaces 100 may surround an axis 102 of the channel 90. The pressing surfaces 100 may be configured such that as the rotatable body 98 is rotated, a body presses and moves the pressing surfaces 100 towards the center of the channel 90 and the diameter of the channel 90 reduces. The pressing surfaces 100 may form an iris structure that allows the pressing surfaces 100 to move towards the center of the channel 90 and reduce the diameter of the channel 90. An implant 10 positioned within the channel 90 will accordingly be compressed within the channel 90, due to the radially compressive force of the pressing surfaces 100 against the implant.

Figure 7:
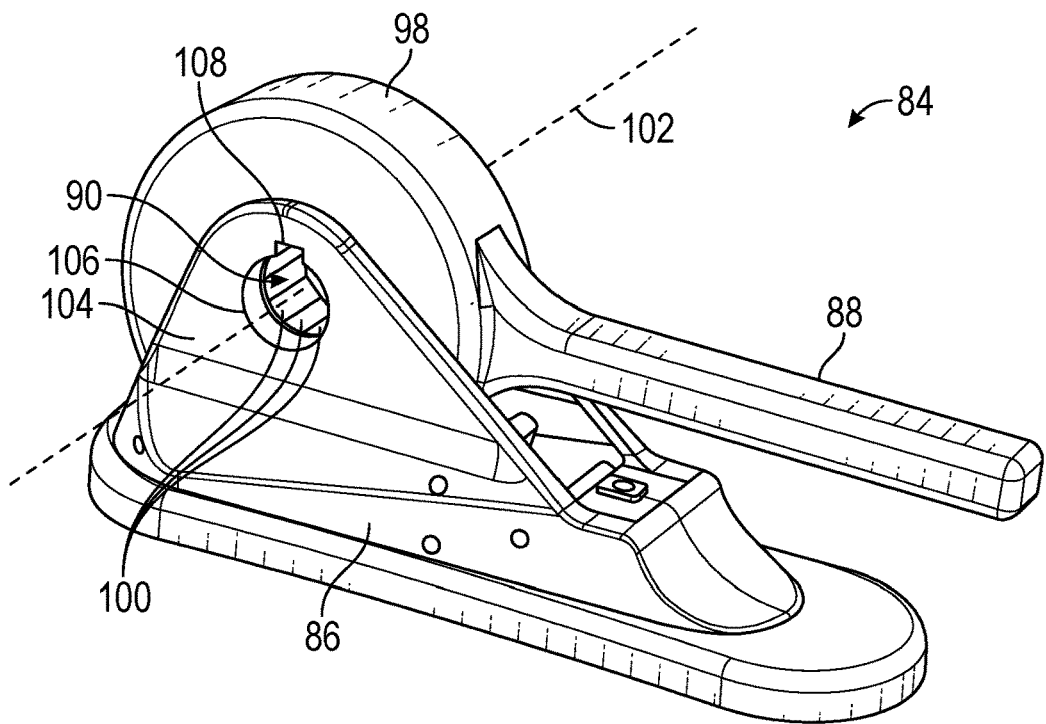
FIG. 7 illustrates a front perspective view of the crimping device shown in FIG. 6.

FIG. 7 illustrates a front perspective view of a crimping device 84 (or a view from the distal side of the crimping device 84). The crimping device 84 may include a distal face 104 including a distal opening 106 that leads into the channel 90. The distal face 104 may include a cut out portion 108 that may be configured as a notch or other shape in the distal face 104.

The distal opening 106 may be configured for a portion of the delivery apparatus 44 to pass through upon a crimping operation being performed by the crimping device 84.

The configuration of a crimping device may be varied in embodiments as desired.

In operation, the implant 10 may be positioned upon the implant retention area 54 of the delivery apparatus 44 and then the delivery apparatus 44 with the implant 10 positioned thereon may be inserted into the channel 90. Notably, however, if the leaflets 18*a-c* of the implant 10 are in a closed position (as represented in FIG. 2) upon crimping of the implant 10 to the delivery apparatus 44, then adverse conditions may result for the implant 10. For example, if the implant 10 is crimped to the delivery apparatus 44 with the leaflets 18*a-c* in a closed position, then one or more sutures coupling the leaflets 18*a-c* to the frame 16 may have the suture holes elongate. The suture holes may elongate along one or more suture lines 42*a-c* as shown in FIG. 2. The elongation of the suture holes may result in a variety of adverse conditions, including separation of the leaflets 18*a-c* from the frame 16 and may result in reduction of the integrity of the fluid seal outside of the flow channel 37 (marked in FIG. 3) of the implant 10. Further adverse conditions may include undesired pull out of the tabs 40*a-f* shown in FIG. 2, or misalignment of the tabs 40*a-f* at the commissure points. It is believed that positioning the leaflets 18*a-c* in an open position during crimping of the implant 10 may reduce one or more of the aforementioned adverse conditions.

Figure 8:
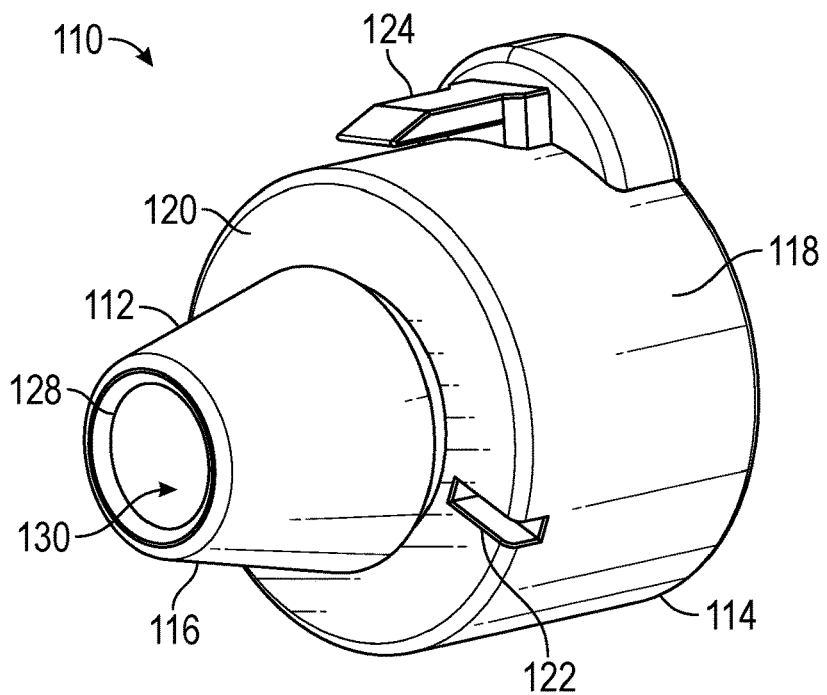
FIG. 8 illustrates a front perspective view of a support body according to an embodiment of the present disclosure.

A support body may be utilized to support the one or more leaflets 18*a-c* in an open position. FIG. 8, for example, illustrates a perspective view of a support body 110 according to an embodiment of the present disclosure. The support body 110 may be configured to be inserted into a crimping device and may have a support surface 112 configured to be positioned between the one or more leaflets 18*a-c* and the delivery apparatus 44 and for supporting the one or more leaflets 18*a-c* in an open position. The support body 110 may have a first end portion 114 and may extend to a second end portion 116 including the support surface 112. The support body 110 may comprise a system for use in crimping a prosthetic implant having one or more leaflets to a delivery apparatus, and the system may include other components as desired.

Figure 12:
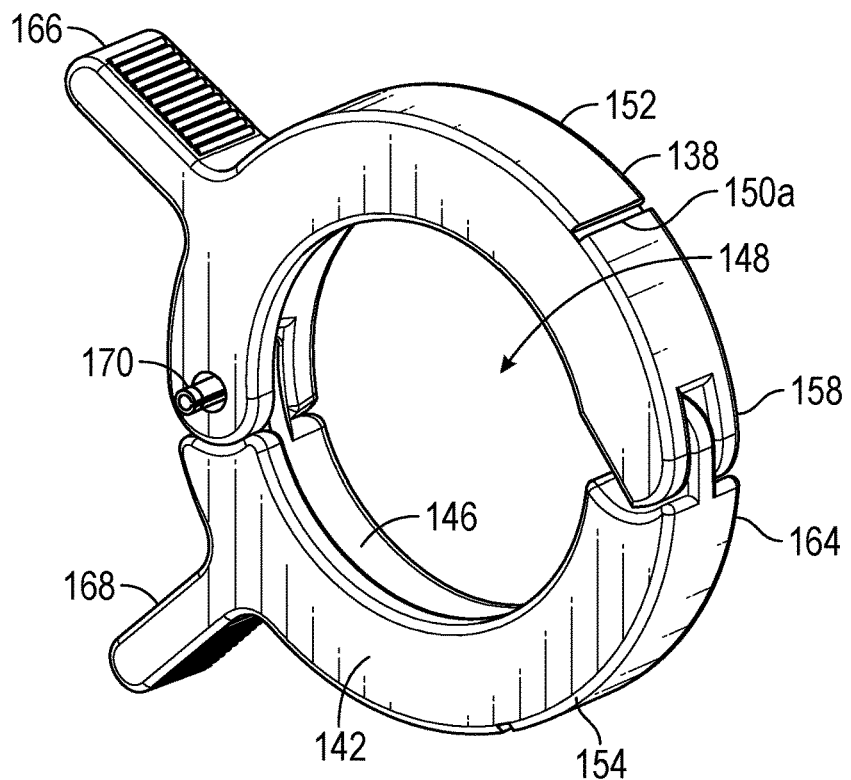
FIG. 12 illustrates a rear perspective view of the ring body shown in FIG. 11 according to an embodiment of the present disclosure.

The first end portion 114 may have a cylindrical shape with a cylindrical outer surface 118. The first end portion 114 may extend to a proximally facing surface 120 that may extend transverse to the cylindrical outer surface 118. The proximally facing surface 120 may join the first end portion 114 to the second end portion 116 including the support surface 112. The proximally facing surface 120 may include an alignment device in the form of a recess 122, which may be configured to receive a coupler 170 of a ring body 138 as shown in FIG. 12.

Figure 54:
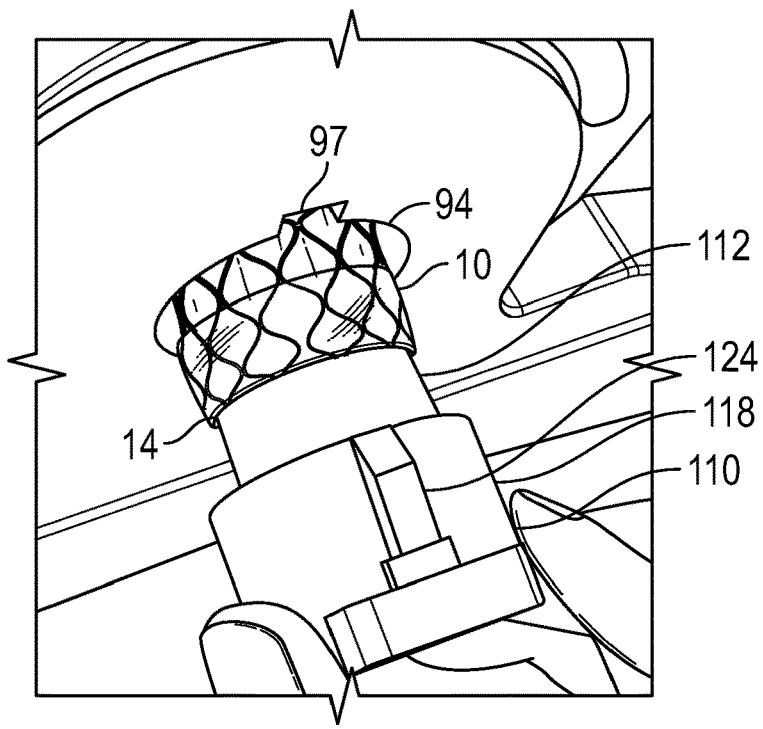
FIG. 54 illustrates a perspective view of a prosthetic implant positioned upon a support body and being inserted into a crimping device.
Figure 55:
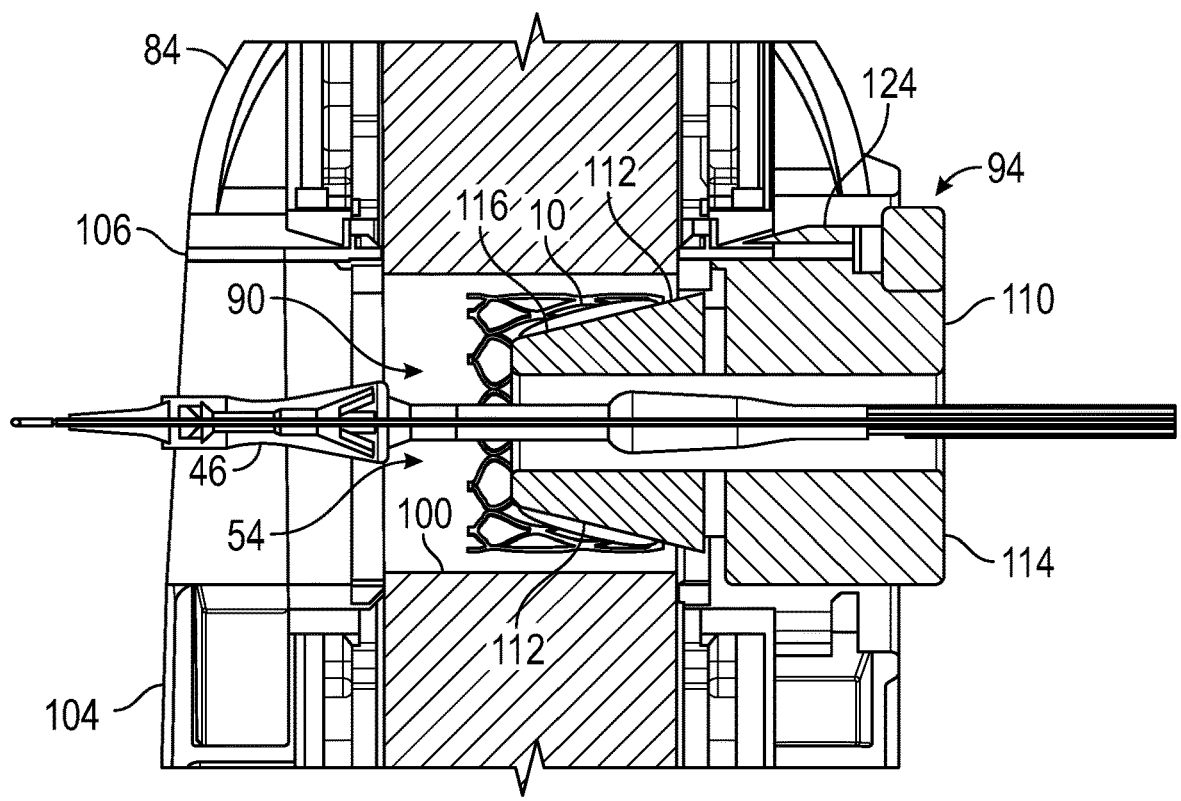
FIG. 55 illustrates a side cross sectional view of an implant positioned upon a support body and positioned within a crimping device.

An alignment device 124 may be positioned on the first end portion 114 and may be configured to rotationally align the support body 110 with the crimping device 84. The alignment device 124 may be circumferentially positioned on the first end portion 114 at a position to rotationally align the support body 110 with the crimping device 84. The alignment device 124 may comprise an axially extending protrusion as shown in FIG. 8, or in other embodiments may have other configurations, such as a recess or other forms of alignment device. The alignment device 124 may be configured to insert into the cut out portion 108 on the distal face 104 of the crimping device 84 to rotationally align the support body 110 with the crimping device 84. The alignment device 124 may further be configured to allow the support body 110 to slide distally out of the cut out portion 108 upon the crimping device 84 operating. In embodiments, the alignment device 124 may be inserted into the proximal face of the crimping device 84, and may be inserted into the cut out portion 97, for example as shown in FIGS. 54 and 55.

The second end portion 116 may extend proximally from the first end portion 114. The support body 110 at the second end portion 116 may include the support surface 112. The support surface 112 may have a tapered shape that tapers downward in a direction towards the second end portion 116. The diameter of the support surface 112 decreases in a direction towards the second end portion 116. The support surface 112 may have a conical shape as shown in FIG. 8, or may have another shape as desired in other embodiments. The support surface 112 may have a greatest diameter that is less than the diameter of the cylindrical first end portion 114 as shown in FIG. 8, or may have another configuration as desired. A connector portion 126 (marked in FIG. 10) may join the support surface 112 to the proximally facing surface 120 and may have a cylindrical shape with a constant diameter or may have another shape as desired.

The support surface 112 may be configured for the interior surfaces 34*a-c* of the leaflets 18*a-c* (marked in FIG. 3) to contact and rest upon when the implant 10 is positioned upon the support surface 112. The support surface 112 may be configured to resist the leaflets 18*a-c* from moving to a closed position when the implant 10 is positioned upon the support surface 112 and within the crimping device 84.

A tapered shape of the support surface 112 may allow the support body 110 to be slid distally when the pressing surfaces 100 of the crimping device 84 press upon the support surface 112. As such, the tapered shape may cause a pressing force applied by the pressing surfaces 100 to move proximally along the tapered shape of the support surface 112 and thus moving the support body 110 distally in response. The support surface 112, however, may yet maintain the leaflets 18*a-c* in an open position as the pressing surfaces 100 press against the tapered support surface 112. The tapered shape of the support surface of the support body may include a wide portion and a narrow portion, and positioning the prosthetic implant upon the support body may include positioning the prosthetic implant upon the support body such that the one or more leaflets open in a direction from the wide portion towards the narrow portion. The support body 110 may be configured to slide axially away from the implant 10 upon the crimping device 84 crimping the implant 10. The support body 110, for example, may be configured to insert into the channel 90 of the crimping device 84 and slide axially away from the channel 90 upon the crimping device 84 crimping the implant 10, and may slide in an axially distal direction within the channel away from the prosthetic implant.

The support body 110 may include a central aperture 128 leading to a central channel 130. The central aperture 128 and central channel 130 may be configured for the delivery apparatus 44 to extend through. The support surface 112 may extend around the central channel 130. The central aperture 128 may be positioned on the second end portion 116 and the central channel 130 may extend from the second end portion 116 to the first end portion 114.

Figure 9:
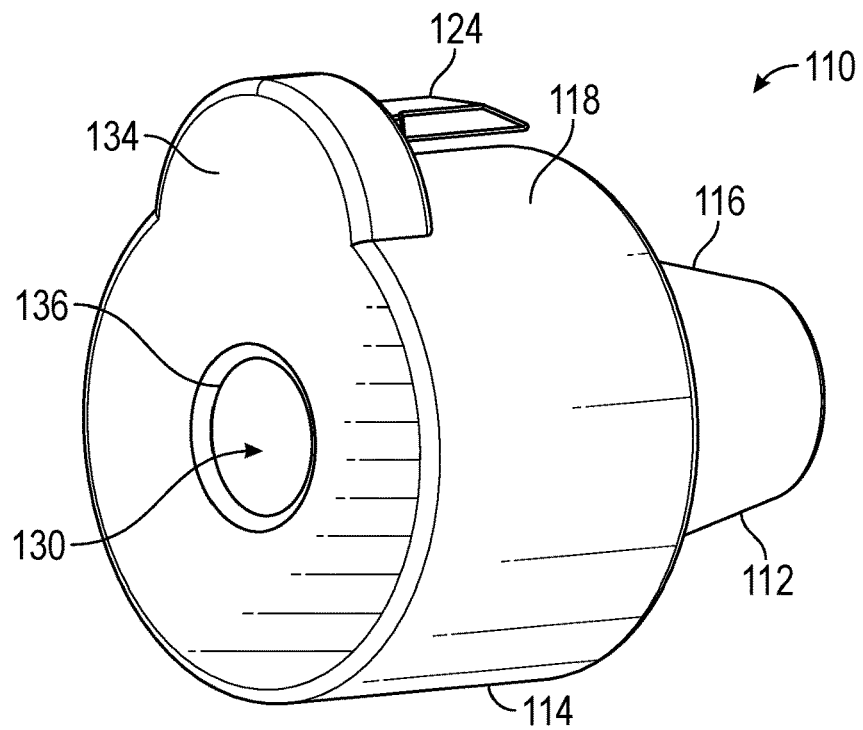
FIG. 9 illustrates a rear perspective view of the support body shown in FIG. 8 according to an embodiment of the present disclosure.

FIG. 9 illustrates a distal perspective view of the support body 110. The first end portion 114 includes a distally facing surface 134 that extends perpendicular to and joins to the cylindrical outer surface 118. The distally facing surface 134 includes a central aperture 136 that leads to the central channel 130, which extends to the central aperture 128 of the second end portion 116 (shown in FIG. 8).

Figure 10:
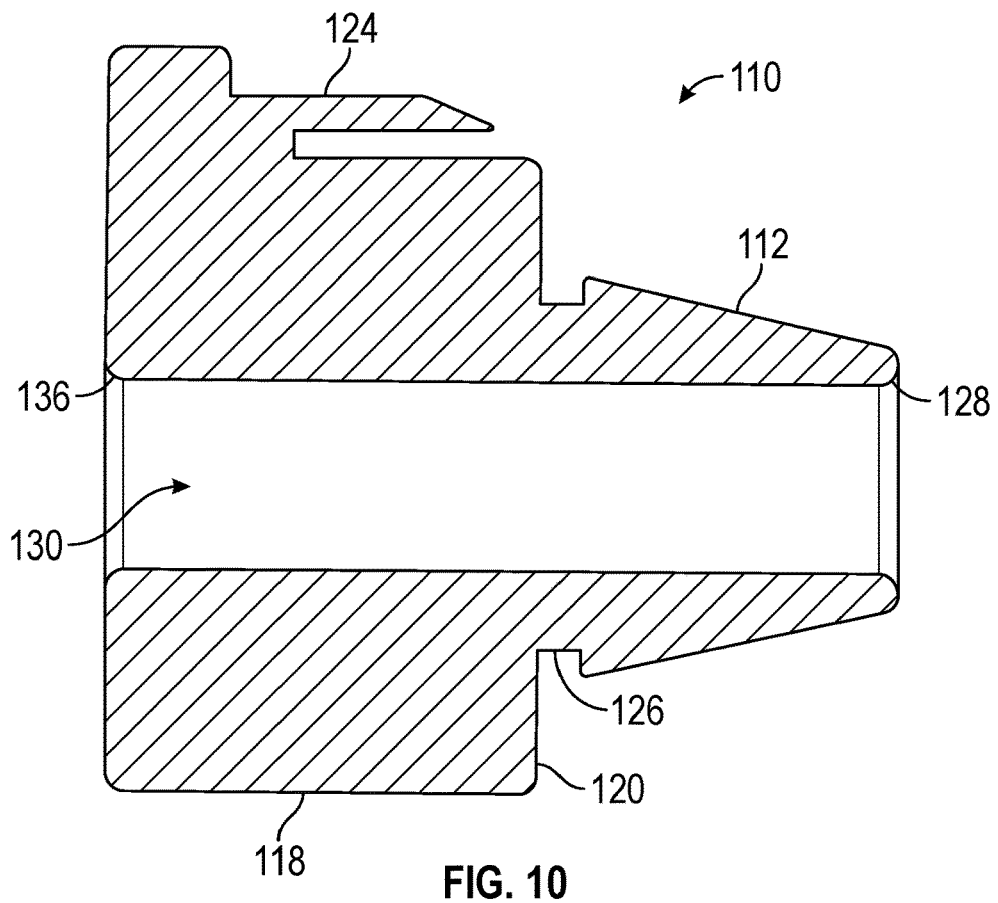
FIG. 10 illustrates a side cross sectional view of the support body shown in FIG. 8 according to an embodiment of the present disclosure.

FIG. 10 illustrates a cross sectional view of the support body 110. The central channel 130 is shown to extend from the distal central aperture 136 to the proximal central aperture 128.

In operation, the implant 10 may be slid distally onto the support surface 112 of the support body 110, with the frame 16 extending over the support surface 112 and the interior surface 34a-c of the leaflets 18a-c upon the support surface 112. The implant 10 in embodiments may be slid distally with the distal end 14 of the implant 10 leading in a direction from the second end portion 116 to the first end portion 114. In embodiments, the implant 10 may be slid onto the support body with the proximal end of the implant leading. Such a configuration may be utilized if an opposite delivery path to the implantation site may be utilized than with the distal end of the implant leading. To align the leaflets 18a-c in a desired rotational orientation upon the support surface 112, and to space the implant 10 from the proximally facing surface 120 at a desired spacing, a ring body may be utilized and positioned upon the support body 110.

Figure 11:
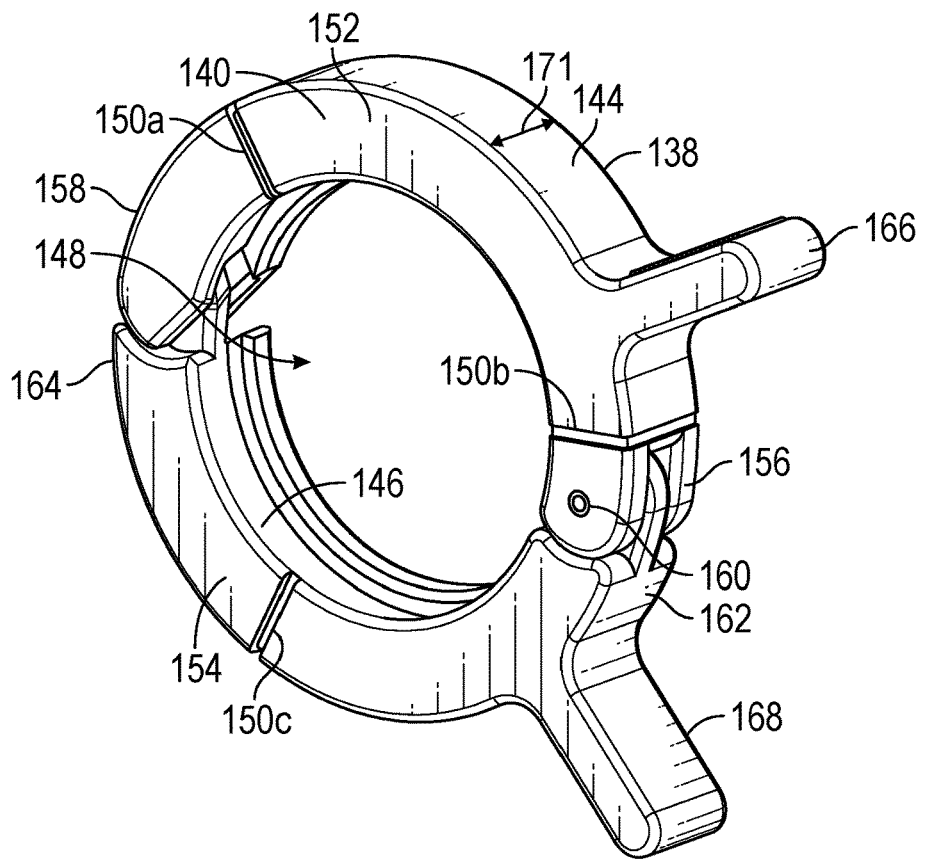
FIG. 11 illustrates a front perspective view of a ring body according to an embodiment of the present disclosure.

FIG. 11, for example, illustrates a perspective view of a ring body 138 that may be utilized with a support body 110. The ring body 138 may be configured to extend around the support body 110. The ring body 138 may include a first surface which may be a proximally facing surface 140, a second surface facing opposite the first surface and which may be a distally facing surface 142 (marked in FIG. 12) and an outer surface 144 facing outward and connecting the proximally facing surface 140 to the distally facing surface 142. The ring body 138 may include an inner surface 146 facing opposite the outer surface 144 and facing towards and surrounding a central channel 148 of the ring body 138.

An alignment guide may be positioned on the ring body 138 and may comprise one or more indicators 150a-c indicating a rotational position of the implant 10 relative to the ring body 138. Each indicator 150a-c may indicate a rotational position of the implant 10 upon the support body 110. Each indicator 150a-c may comprise a marking or other form of indicator on one or more of the proximally facing surface 140, the distally facing surface 142, or the outer surface 144 of the ring body 138. Each indicator 150a-c for example may comprise a variation in the surface profile of the ring body 138, such as a raised portion or a recessed portion. The indicators 150a-c shown in FIG. 11, for example, each comprise recessed portions in the form of grooves on the proximally facing surface 140 and extending to the outer surface 144. The indicators 150a-c may further be printed upon to vary a color of the respective indicator 150a-c such that the indicator is easier to visualize. In embodiments, the indicators 150a-c may solely be printed upon the ring body 138 without use of a variation of the surface profile.

The indicators 150a-c may be circumferentially spaced from each other on the ring body 138 and may be equally spaced from each other. The position of each indicator 150a-c may correspond to a position of one or more leaflets 18a-c of the implant 10. The position of each indicator 150a-c for example may correspond to and indicate a position of one or more commissures of the one or more leaflets 18a-c. As such, a user may position the ring body 138 on the support body 110 and align the commissures of the leaflets 18a-c with a respective indicator 150a-c.

The ring body 138 may include one or more arms 152, 154 each extending around the central channel 148. Each arm 152, 154 may have an arcuate shape forming the ring body 138. Each arm 152, 154 may comprise half of the ring body 138 or another amount as desired.

The first arm 152 may include a first end portion 156 and a second end portion 158, with the first end portion 156 positioned at a pivot 160 that couples the first arm 152 to the second arm 154. The second end portion 158 of the first arm 152 may include a coupler for coupling to the second arm 154. The second arm 154 may include a first end portion 162 positioned at the pivot 160 and a second end portion 164 positioned at the coupler. The coupler may comprise a recess in the second end portion 158 of the first arm 152, and a protrusion at the second end portion 164 of the second arm 154. The protrusion may extend into the recess and may be held in position with an interference fit or another form of coupling. As such, the second end portions 158, 164 of the respective first arm 152 and second arm 154 may be configured to couple to each other to hold the ring body 138 together. If desired, the ring body 138 may be separated and removed from the support body 110 by the second end portions 158, 164 being separated from each other and the arms 152, 154 pivoted about the pivot 160 to an open position. The ring body 138 may be opened to be removed from the support body 110 and may be closed to be held upon the support body 110.

As shown in FIG. 11, a first lever 166 may extend radially outward from the first arm 152, and a second lever 168 may extend radially outward from the second arm 154. The first lever 166 and second lever 168 may each be configured to be pressed to rotate the first arm 152 or the second arm 154 about the pivot 160 to cause the ring body 138 to move to the open position.

The ring body 138 may have an axial width 171 that may define a spacing of the implant 10 from the proximally facing surface 120 of the support body 110 shown in FIG. 8.

FIG. 12 illustrates a distal perspective view of the ring body 138. A coupler 170 may extend distally from the distally facing surface 142. The coupler 170 may be configured as a protrusion or other form of coupler. The coupler 170 may be configured to extend into the recess 122 shown in FIG. 8. The coupler 170 may be circumferentially positioned relative to the recess 122 such that the ring body 138 mates with the support body 110 at a desired rotational alignment. The coupler 170 may rotationally align the ring body 138 with the support body 110.

Figure 13:
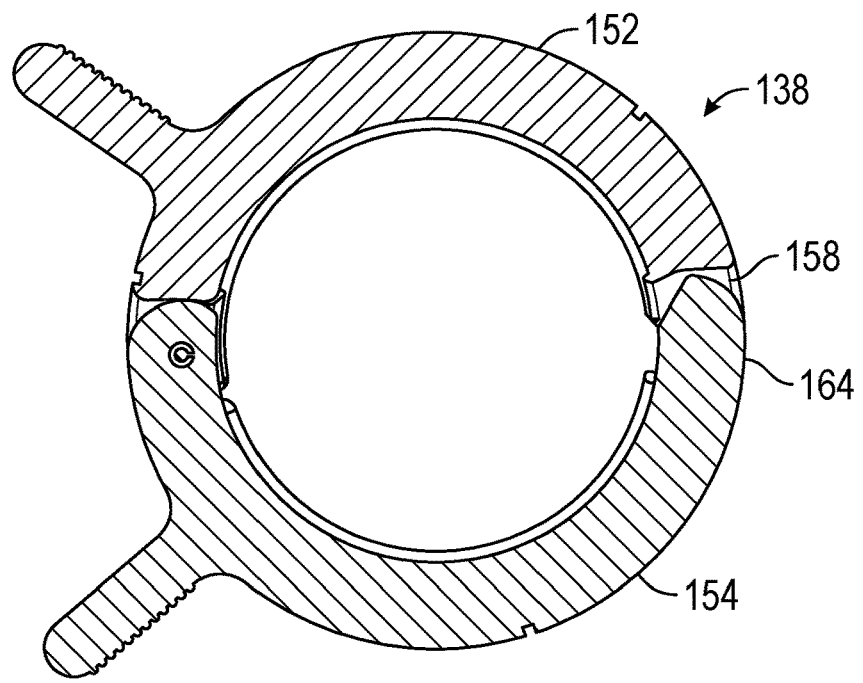
FIG. 13 illustrates a cross sectional view of the ring body shown in FIG. 11.

FIG. 13 illustrates a cross sectional view of the ring body 138. The insertion of the second end portion 164 of the second arm 154 into the recess of the second end portion 158 of the first arm 152 is shown in FIG. 13.

Figure 14:
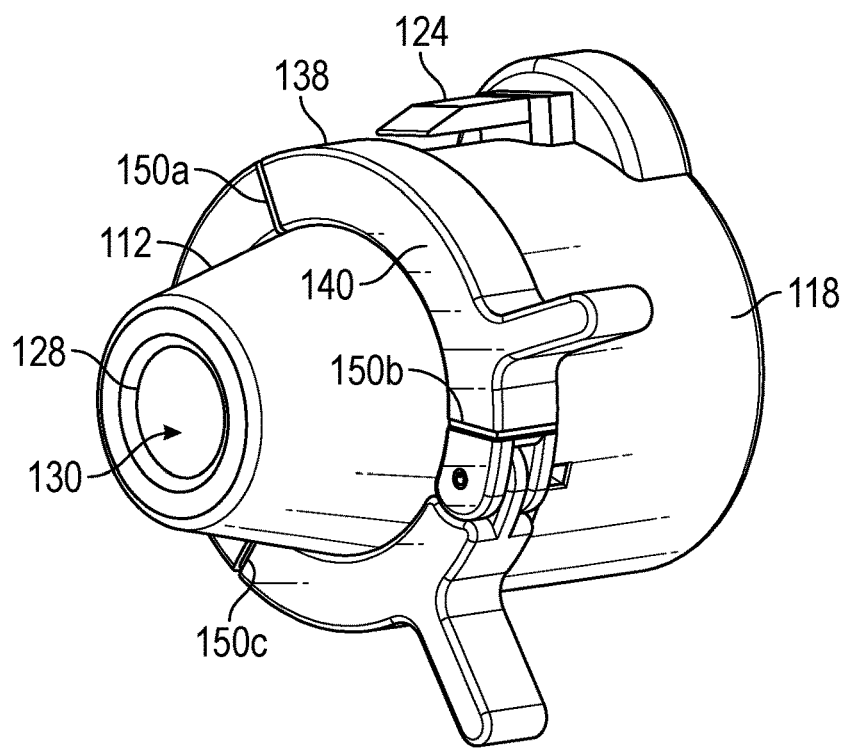
FIG. 14 illustrates the ring body shown in FIG. 11 positioned upon the support body shown in FIG. 8.
Figure 15:
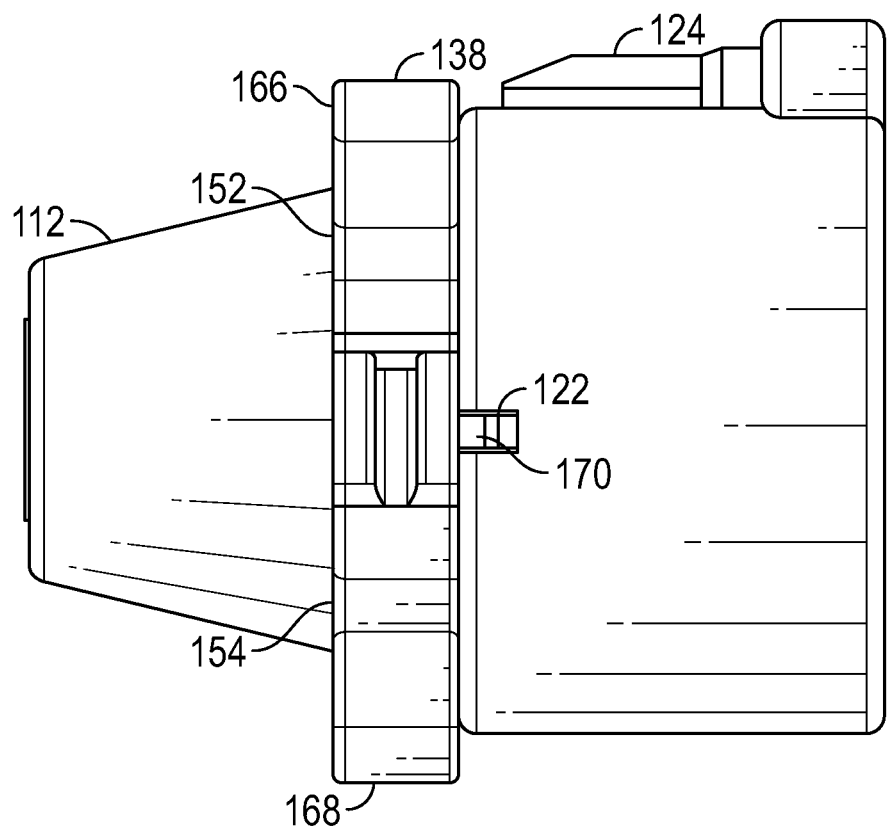
FIG. 15 illustrates a side view of the ring body positioned upon the support body in the configuration shown in FIG. 14.

In operation, the ring body 138 may be positioned upon the support body 110, with the indicators 150a-c positioned at a desired rotational alignment relative to the support body 110. The coupler 170 shown in FIG. 12, for example, may enter the recess 122 at a rotational position such that the ring body 138 is rotationally positioned as desired relative to the support body 110. FIG. 14, for example, illustrates the ring body 138 upon the support body 110 with the coupler 170 inserted into the recess 122. FIG. 15 illustrates a side view of the ring body 138 upon the support body 110 with the coupler 170 inserted into the recess 122. In other embodiments, other alignment devices may be utilized to rotationally align the ring body 138 with respect to the support body 110 in the desired rotational alignment.

The ring body 138 may abut the proximally facing surface 120 shown in FIG. 8. The axial width 171 of the ring body 138 shown in FIG. 11 may define a spacing of the implant 10 from the proximally facing surface 120 of the support body 110. The ring body 138 may be configured to abut the prosthetic implant 10 when the prosthetic implant 10 is positioned on the support body 110. As such, the implant 10 may be positioned on the support surface 112 with an end of the implant 10 abutting the proximally facing surface 140 of the ring body 138 and defining a position of the implant 10 upon the support surface 112. The ring body 138 accordingly may comprise a spacer configured to define a position of the implant 10 upon the support body 110.

The ring body 138 may be placed in an open configuration with the arms 152, 154 open and then may be placed on the support body 110 with the arms 152, 154 closed to secure the ring body 138 around the support body 110. The ring body 138 may be positioned upon the connector portion 126 shown in FIG. 10 for example.

The implant 10 may then be positioned upon the support surface 112 and abutted against the proximally facing surface 140 of the ring body 138. The implant 10 may be positioned upon the support surface 112 with the commissures of the leaflets 18a-c aligned with the indicators 150a-c and an end of the implant 10 abutting the proximally facing surface 140.

The use of the ring body 138 may beneficially allow the commissures of the leaflets 18a-c and the leaflets 18a-c themselves to be placed in a desired rotational orientation relative to the ring body 138 and thus relative to the support body 110. The alignment device 124 on the support body 110 as shown in FIG. 8 may rotationally align the support body 110 with the crimping device 84 and thus place the commissures of the leaflets 18a-c and the leaflets 18a-c themselves in a desired rotational orientation within the crimping device 84.

It may be desirable to have the commissures of the leaflets 18a-c and the leaflets 18a-c in a known rotational orientation within the crimping device 84 to have the implant 10 crimp to the delivery apparatus 44 at a known rotational orientation. As such, a user crimping the implant 10 to the delivery apparatus 44 may be aware of the position of the commissures of the leaflets 18a-c and the leaflets 18a-c upon the delivery apparatus 44 when the implant 10 is crimped. Thus, during deployment of the implant 10 from the delivery apparatus 44, a user may be able to place the commissures and the leaflets 18a-c in a desired orientation relative to the implantation site. For example, if the implant 10 is deployed to a native heart valve, the prosthetic leaflets 18a-c and commissures may be deployed in an orientation that closely matches the position of the native leaflets and commissures. A more effective deployment of the implant 10 may thus result by placing the commissures of the leaflets 18a-c and the leaflets 18a-c at a known orientation relative to the delivery apparatus 44.

The support body 110 and the ring body 138 may each be part of a system for use in crimping a prosthetic implant having one or more leaflets to a delivery apparatus. In embodiments, the systems may include a positioning device 172 configured to couple to a portion of the delivery apparatus 44 proximal of the implant retention area 54. FIG. 16, for example, illustrates an embodiment of such a positioning device 172 positioned proximal of the implant retention area 54. The positioning device 172 includes a body 174 including a first portion 176 and a second portion 178 joined at a hinge 180. The body 174 may include a central channel 182 that the delivery apparatus 44 may be positioned in, with the second portion 178 rotating about the hinge 180 to close the central channel 182 and retain the delivery apparatus 44 within the central channel 182.

The body 174 may further include mating surfaces in the forms of flanges 184 that are configured to engage the mating structures 96 of the proximal face 92 of the crimping device 84 shown in FIG. 6.

Figure 19:
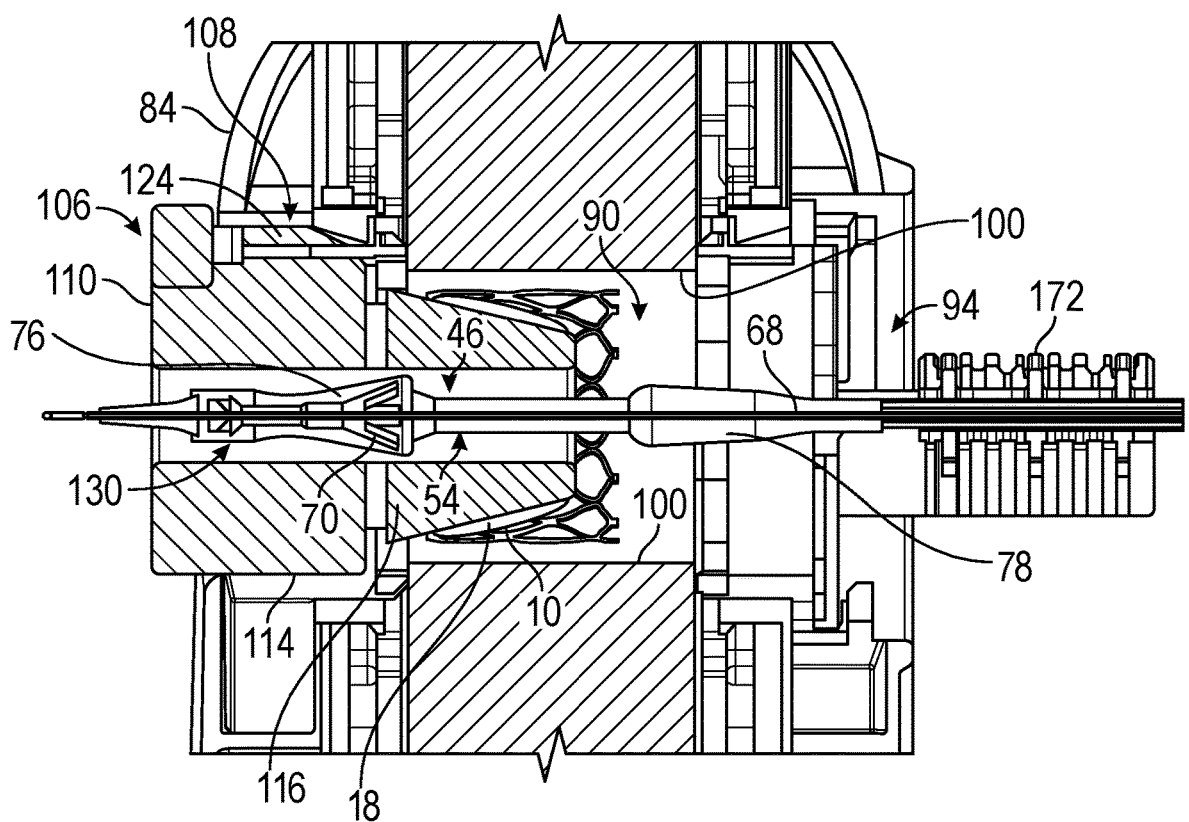
FIG. 19 illustrates a side cross sectional view of an implant positioned upon a support body and positioned within a crimping device.

The positioning device 172 may be utilized to couple to the delivery apparatus 44 and suspend the shaft of the delivery apparatus 44 in position within the channel 90 of the crimping device 84. The positioning device 172 accordingly may hold the delivery apparatus 44 spaced from the pressing surfaces 100 of the crimping device 84 as shown in FIG. 19 for example. Further, the positioning device 172 may be positioned axially along the delivery apparatus 44 such that the implant retention area 54 is held within a defined axial position within the channel 90 of the crimping device 84. Such a feature may further allow the distal shoulder 70 of the interior shaft 68 shown in FIG. 5 to be positioned outside of the channel 90 of the crimping device 84 and distal of the channel 90 such that the distal shoulder 70 is not pressed by the pressing surfaces 100 during crimping. The delivery apparatus 44 may further be held in a defined axial position relative to the implant 10 positioned upon the support body 110.

A method of operation of the systems disclosed herein may include the following steps. Steps may be modified, excluded, or substituted across embodiments as desired.

In an initial step, the implant 10 to be crimped may be soaked to improve ease of crimping for the implant 10.

The ring body 138 may then be positioned upon the support body 110 in a configuration shown in FIG. 15 for example. The ring body 138 may be rotationally oriented upon the support body 110 in a defined position, for example, via the coupling of the coupler 170 shown in FIG. 13 with the recess 122 shown in FIG. 8 for example. As such, the implant 10 may be positioned upon the support surface 112 with the commissures of the leaflets 18a-c oriented with the indicators 150a-c. The implant 10 may be abutted against the ring body 138 to define the position of the implant 10 upon the support body 110.

Figure 18:
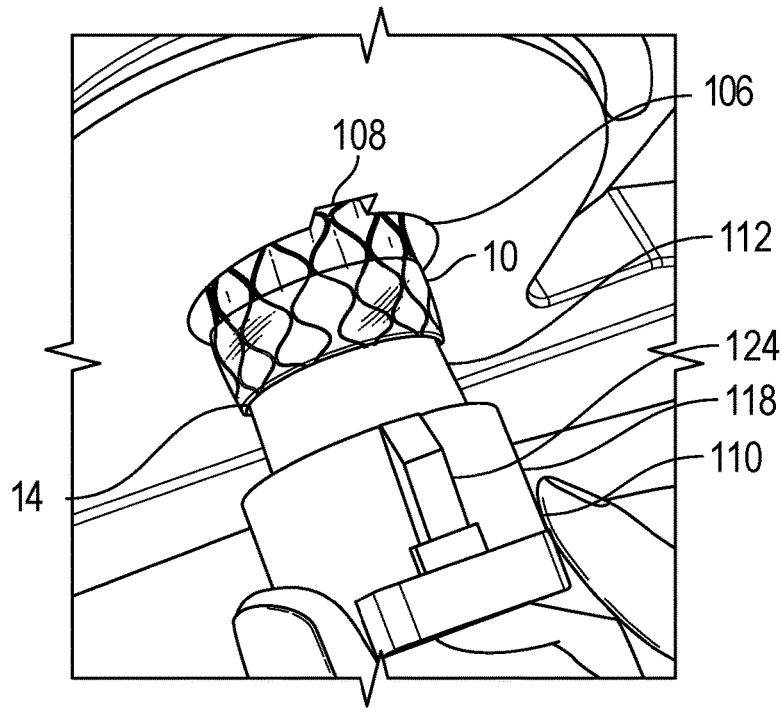
FIG. 18 illustrates a perspective view of a prosthetic implant positioned upon a support body and being inserted into a crimping device.

FIG. 18, for example, illustrates the implant 10 slid onto the support surface 112 of the support body 110 with the distal end 14 (marked in FIG. 1) abutting the proximally facing surface 140. The interior surfaces 34a-c of each of the leaflets 18a-c are in contact with the support surface 112 of the support body 110 and are held in an open position. The commissures of the leaflets 18a-c are aligned with the indicators 150a-c. The implant 10 may be held at an axial spacing upon the support surface 112 that corresponds to the axial width 171 of the ring body 138 (as marked in FIG. 11).

With the implant 10 positioned upon the support surface 112, the ring body 138 may then be removed from the support body 110 prior to crimping the implant 10 to the delivery apparatus 44. For example, the levers 166, 168 may be pressed to rotate the arms 152, 154 about the pivot 160 and open the ring body 138.

With the ring body 138 removed, the support body 110 may be inserted into the crimping device 84 with the implant 10 positioned upon the support surface 112. FIG. 18, for example, illustrates the implant 10 positioned upon the support surface 112 with the implant 10 and support body 110 being inserted into the channel of the crimping device 84. The distal opening 106 of the crimping device 84 may be configured for the support body 110 to be inserted into the channel 90 through. The support body 110 may be configured to insert into the distal opening 106 of the crimping device 84. The channel 90 of the crimping device 84 may be configured to receive the implant 10, the support body 110, and the elongate shaft 46 of the delivery apparatus 44. Upon insertion of the support body 110 into the channel of the crimping device 84, the alignment device 124 may be aligned with the cut out portion 108 of the crimping device 84. As such, the rotational orientation of the support body 110 within the channel of the crimping device 84 and accordingly the rotational orientation of the implant 10 within the channel of the crimping device 84 may be set.

With the support body 110 and the implant 10 inserted into the channel of the crimping device 84, the positioning device 172 shown in FIG. 16 may be coupled to the proximal portion of the delivery apparatus 44 and then inserted into the proximal opening 94 of the crimping device 84 as shown in FIG. 6. The flanges 184 of the positioning device 172 may mate with the mating structures 96 shown in FIG. 6.

FIG. 19 illustrates a cross sectional view of the pressing surfaces 100 in position around the channel 90 of the crimping device 84, and the support body 110 inserted into the channel 90 with the implant 10 positioned upon the support surface 112. The leaflets 18*a-c* are supported upon the support surface 112 with the interior surface 34*a-c* of the leaflets 18*a-c* in contact with the support surface 112. The leaflets 18*a-c* extend proximally and are supported in an open position. The frame 16 of the prosthetic implant 10 extends proximally and surrounds the leaflets 18*a-c*, and the support surface 112, as well as the elongate shaft 46.

The support body 110 extends proximally, with the second end portion 116 directed proximally towards the proximal opening 94 of the crimping device 84. The support surface 112 may be surrounded by the pressing surfaces 100. The first end portion 114 of the support body 110 may be positioned outside of and distal of the pressing surfaces 100, and may be retained within the distal opening 106 of the crimping device 84. The alignment device 124 may extend proximally into the cut out portion 108 of the crimping device 84.

The elongate shaft 46 of the delivery apparatus 44 is positioned within the channel 90 of the crimping device 84. The implant 10 is positioned within the channel 90 and around the delivery apparatus 44. The support body 110 is positioned within the channel 90 and between the leaflets 18*a-c* and the delivery apparatus 44. The support body 110 supports the leaflets 18*a-c* in an open position. The elongate shaft 46 of the delivery apparatus 44 extends distally within the interior channel 90 of the crimping device 84 and distally within the central channel 130 of the support body 110. The channel 90 may be configured for the elongate shaft 46 of the delivery apparatus 44 to be advanced distally through towards the distal opening 106. The support surface 112 extends around the elongate shaft 46 of the delivery apparatus 44.

The positioning device 172 may be coupled to the proximal portion of the elongate shaft 46 of the delivery apparatus 44, and may be engaged with the mating structures 96 of the proximal face 92. The positioning device 172 may be coupled to the proximal portion of the shaft 46 at a location such that the implant retention area 54 is positioned at a desired location within the channel 90 and relative to the implant 10. For example, as shown in FIG. 19, the implant 10 may surround the implant retention area 54 with the proximal shoulder 78 of the balloon 58 positioned proximal of the implant 10, and the distal shoulder 76 of the balloon 58 positioned distal of the implant 10.

Further, the positioning device 172 may be coupled to the proximal portion of the shaft 46 at a location such that the distal shoulder 70 of the interior shaft 68 is positioned distal of the pressing surfaces 100 and thus outside of and distal of the channel 90. Such a feature may reduce the possibility of the distal shoulder 70 being compressed by the pressing surfaces 100 and may reduce the possibility of damage to the distal shoulder 70 that may reduce the ability of the distal shoulder 70 to shield the crimped implant 10.

Figure 17:
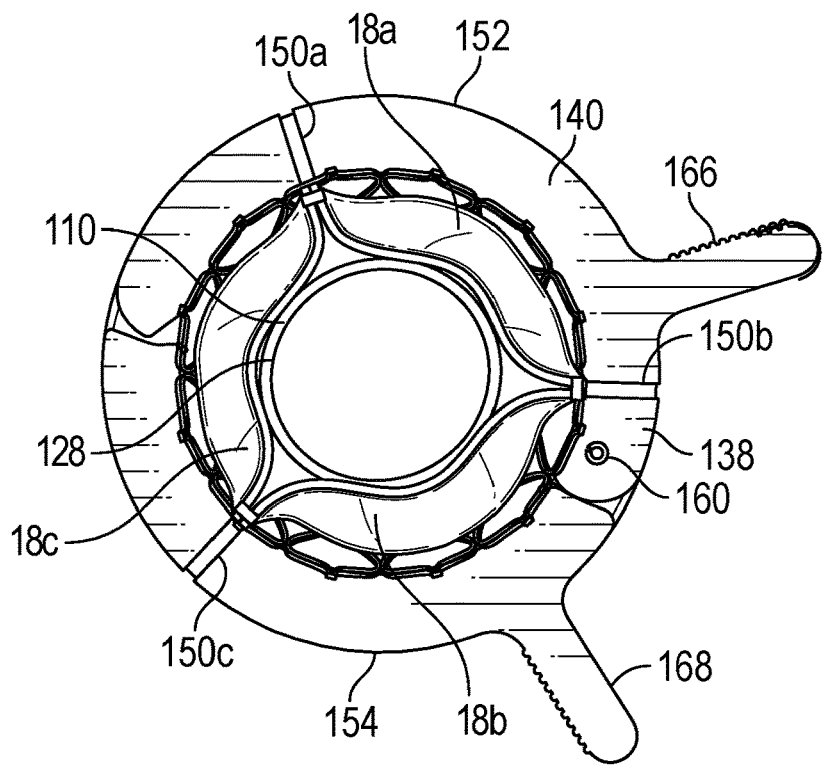
FIG. 17 illustrates a front view of a prosthetic implant positioned upon a support body and adjacent to a ring body according to an embodiment of the present disclosure.

Further, the rotational alignment of the implant 10 relative to the elongate shaft 46 may be in a desired alignment due to the prior use of the ring body 138 shown in FIG. 17.

Figure 20:
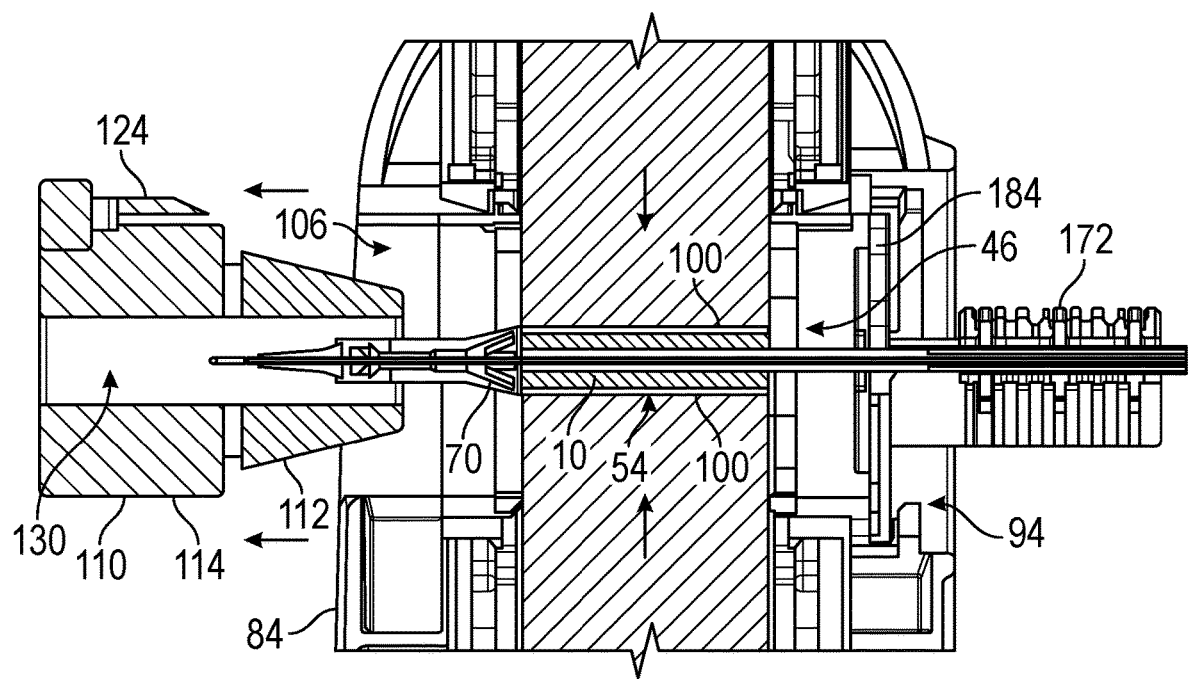
FIG. 20 illustrates a side cross sectional view of the support body shown in FIG. 19 being ejected from the crimping device.

With the elongate shaft 46, support body 110, and implant 10 in a desired position within the channel 90, the actuator of the crimping device 84 may be actuated to compress the implant 10. For example, as shown in FIG. 6, the handle 88 may be rotated to rotate the rotatable body 98 and move the pressing surfaces 100 radially inward against the implant 10. FIG. 20, for example, illustrates the pressing surfaces 100 having been moved radially inward to apply a compressive force to the implant 10. The implant 10 is crimped to the delivery apparatus 44 utilizing the pressing surfaces 100 of the crimping device 84. The implant 10 has compressed radially inward towards the implant retention area 54 of the elongate shaft 46. Further, the length of the implant 10 has axially increased. The proximal shoulder of the balloon 58 may be flattened or otherwise have its size reduced.

The implant 10 may be crimped with the leaflets 18*a-c* remaining in an open position and being retained in the open position. The supporting surface 112 accordingly may support the leaflets 18*a-c* as the pressing surfaces 100 are pressed towards the implant 10. Crimping the implant 10 to the delivery apparatus 44 may include applying a force to the support surface 112 of the support body 110 with the pressing surfaces 100 to cause the support body 110 to slide axially within the channel 90 away from the implant 10.

The tapered shape of the support surface 112 may cause the support body 110 to slide distally away from the channel 90 and away from the pressing surfaces 100 as the pressing surfaces 100 move radially inward. The support body 110 is configured to releasably couple to the crimping device 84 and slide in a direction axially away from the channel 90 upon the crimping device 84 crimping the implant 10. In embodiments, the support body 110 may eject distally from the distal opening 106 as shown in FIG. 20. The support body 110 may eject with the distal tip of the elongate shaft 46 sliding proximally relative to the central channel 130 of the support body 110 and out the central aperture 128 shown in FIG. 8. The support body 110 may slide axially relative to the leaflets 18*a-c*. The elongate shape of the alignment device 124 may allow the alignment device 124 to slide distally out of the cut out portion 108.

In embodiments, the support body 110 may not eject, but may remain coupled to the crimping device 84 during crimping. The support body 110, for example, may slide distally while a tether or another form of coupler keeps the support body 110 coupled to the crimping device 84 such that the support body 110 does not fall.

Upon the implant 10 being crimped to the elongate shaft 46, the positioning device 172 may be disengaged from the mating structures 96 and moved proximally to draw the elongate shaft 46 proximally from the proximal opening 94. The positioning device 172 may be removed from the elongate shaft 46, with the implant 10 remaining crimped to the implant retention area 54.

The use of the support body 110 may beneficially allow the leaflets 18*a-c* of the implant 10 to remain in an open position during crimping. Such a feature may reduce the possibility of adverse conditions to the implant 10 during crimping. Further, the tapered shape of the support surface 112 may allow the support body 110 to be slid distally via the radially inward movement of the pressing surfaces 100, such that the support body 110 automatically is moved distally. The support body 110 may automatically slide distally such that the support surface 112 is not positioned between the implant 10 and the pressing surfaces 100 following crimping. In embodiments, the system may be configured such that a separate mechanism slides the support body 110 distally, such that a tapered shape may not be utilized for the support surface 112. For example, arms or gears or another form of coupler may engage the support body 110 to move the support body 110 away from the implant 10.

The use of the support body 110 may further beneficially allow various sizes of implants 10 to be crimped with the same crimping device 84. If an implant having a varied diameter or length is crimped using the crimping device 84, then the size of the support surface 112 may be varied to accommodate the implant. The implant may then be positioned upon the support surface and inserted into the channel 90 of the crimping device 84 and crimped upon an implant retention area sized for the implant. The positioning device 172 may be positioned along the length of the elongate shaft 46 to continue to maintain the distal shoulder 70 of the elongate shaft outside of the pressing surfaces 100.

Figure 21:
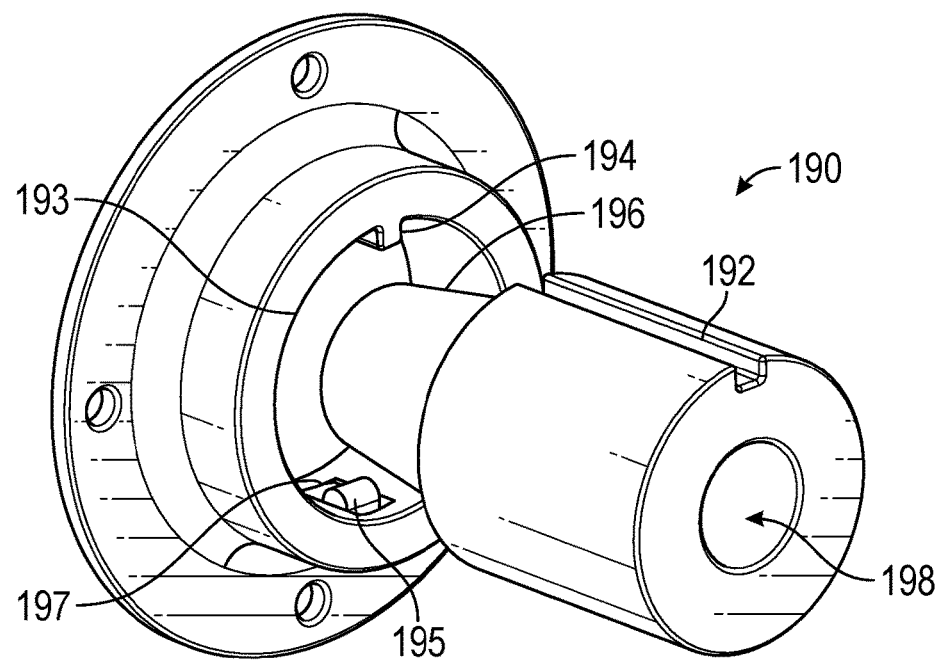
FIG. 21 illustrates a rear perspective view of a support body configured to be inserted into a crimping device according to an embodiment of the present disclosure.

FIG. 21 illustrates a distal perspective view of a variation of the support body, including a support body 190 having an alignment device 192 in the form of a recess in the outer surface of the support body 190. An opening 193 of the distal face of a crimping device (not shown) is shown, with the opening 193 being positioned upon the distal face in a similar manner as the distal opening 106 shown in FIG. 7. The alignment device 192 may be configured to rotationally align the support body 190 with an alignment guide 194 of the crimping device. For example, the alignment guide 194 may comprise a protrusion that slides within the recess of the alignment device 192 when the support body 190 is slid into the crimping device in a proximal direction. The alignment device 192 accordingly may operate to rotationally align the support body 190 in a similar manner as the alignment device 124 shown in FIG. 8.

The support body 190 may be configured to engage a retainer 195 that may be positioned on an interior surface 197 of the opening 193. The retainer 195 may be configured to selectively engage a catch on the support body 190 to allow the support body 190 to remain in position within the opening 193. The catch may disengage from the retainer 195 upon the support body 190 being slid distally. For example, the retainer 195 may comprise a detent device that deflects to allow the catch to release and allow the support body 190 to be slid distally. The relative positions of the retainer 195 and catch may further rotationally align the support body 190 with the opening 193.

The support body 190 may further include a support surface 196 that operates similarly as the support surface 112 shown in FIG. 8. The support body 190 may further include a central channel 198 that operates similar to the central channel 130 shown in FIG. 10.

The support body 190 may operate in a similar manner as the operation of the support body 110 shown in FIGS. 19 and 20.

In embodiments, other configurations of support bodies, and ring bodies may be utilized as desired. The embodiments may be utilized separately from other components disclosed herein, or with other components disclosed herein. In one embodiment, the support body may be configured to be inserted in a proximal side of the crimping body, for example, to engage the cut out portion 97 shown in FIG. 6. The support body 110 may be configured to insert into the proximal opening 94 of the crimping device.

FIG. 54, for example, illustrates the implant 10 positioned upon the support surface 112 with the implant 10 and support body 110 being inserted into the channel of the crimping device 84. The proximal opening 94 of the crimping device 84 may be configured for the support body 110 to be inserted into the channel 90 through. The channel 90 of the crimping device 84 may be configured to receive the implant 10, the support body 110, and the elongate shaft 46 of the delivery apparatus 44.

A ring body 138 as shown in FIGS. 11-15 may be coupled to the support body 110 and utilized to align the implant 10 upon the support body 110 in an embodiment in which the support body 110 is inserted into the proximal opening 94 of the crimping device 84.

In an embodiment in which the support body 110 is inserted into the proximal opening 94 of the crimping device 84, the positioning device 172 shown in FIG. 16 may be excluded from use. As such, the support body 110 may be positioned at the proximal opening 94 of the crimping device 84, and not the positioning device 172.

FIG. 55, for example, illustrates the support body 110 extending distally, with the second end portion 116 directed distally towards the distal opening 106 of the crimping device 84. The support surface 112 may be surrounded by the pressing surfaces 100. The first end portion 114 of the support body 110 may be positioned outside of and proximal of the pressing surfaces 100, and may be retained within the proximal opening 94 of the crimping device 84.

The tapered shape of the support surface 112 may cause the support body 110 to slide proximally away from the channel 90 and away from the pressing surfaces 100 as the pressing surfaces 100 move radially inward. The support body 110 is configured to releasably couple to the crimping device 84 and slide in a direction axially away from the channel 90 upon the crimping device 84 crimping the implant 10.

Figure 56:
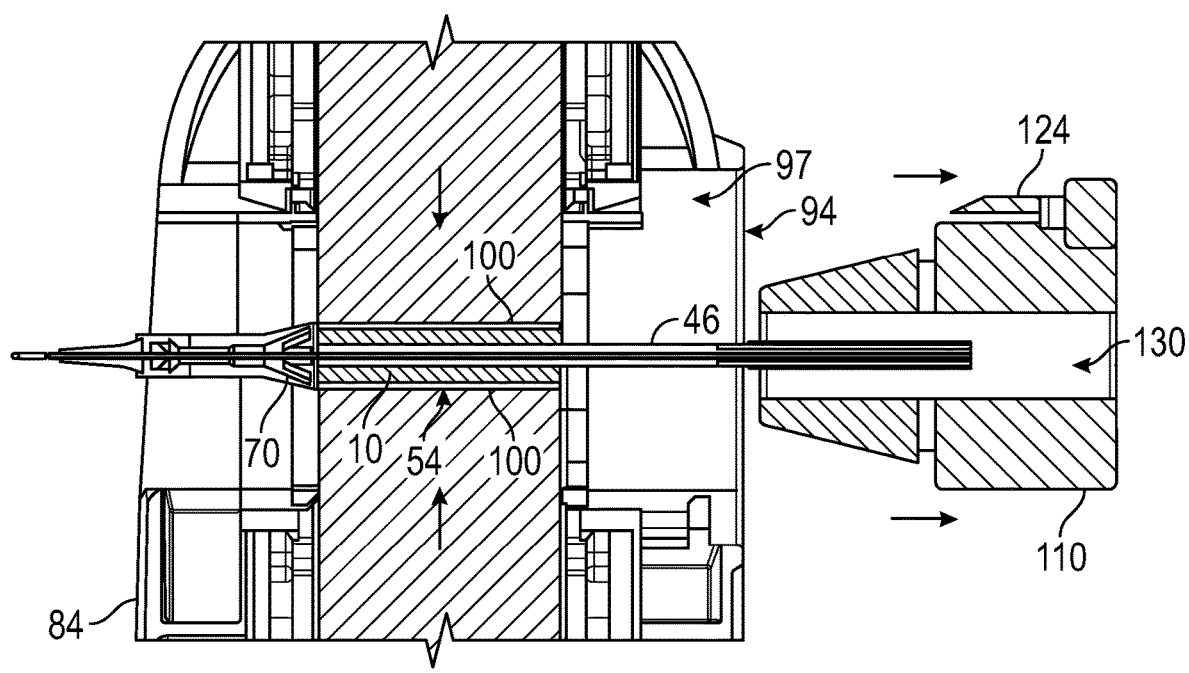
FIG. 56 illustrates a side cross sectional view of the support body shown in FIG. 55 being ejected from the crimping device.

As shown in FIG. 56, the support body 110 may eject proximally from the proximal opening 94. The support body 110 may eject with the elongate shaft 46 relatively sliding distally with respect to central channel 130 of the support body 110. The support body 110 may slide axially relative to the leaflets 18*a*-*c* and may slide in a proximal direction axially away from the channel of the crimping device upon the crimping device crimping the prosthetic implant. The elongate shape of the alignment device 124 may allow the alignment device 124 to slide proximally out of the cut out portion 97. The elongate shaft 46 may be then be withdrawn from the crimping device 84 proximally. The support body 110 may be positioned around the elongate shaft 46 and may then slid distally to be removed from the elongate shaft 46.

A configuration as shown in FIGS. 54-56 may allow the implant 10 to be crimped onto the elongate shaft 46 of the delivery apparatus in an opposite orientation than shown in FIGS. 18-20 (e.g., an antegrade crimping rather than a retrograde crimping as represented in FIGS. 18-20). As such, the orientation of the leaflets 18*a*-*c* and the direction of flow of the implant 10 may be opposite those represented in FIGS. 18-20. In FIGS. 18-20, the implant 10 may be positioned upon the elongate shaft 46 to allow for fluid flow through the implant 10 in a proximal direction when implanted. However, in an embodiment as shown in FIGS.

54-56, the implant 10 may be positioned upon the elongate shaft 46 to allow for flow in a distal direction when the implant 10 is implanted.

As such, in a configuration as shown in FIGS. 54-56, the implant 10 may be implanted to an implantation site at an opposite orientation than represented in FIGS. 18-20. The approach to an implantation site, such as a native valve, accordingly may be opposite for the embodiment of FIGS. 54-56 than represented in FIGS. 18-20. For example, in the embodiment of FIGS. 18-20, an approach to an aortic valve may occur transfemoral, and over the aortic arch and in a ventricular direction towards the aortic valve. The implant 10 may be implanted to the aortic valve, with the direction of flow extending away from the left ventricle. In an embodiment of FIGS. 54-56, an approach to an implantation site may be in an opposite direction relative to the implantation site (and the direction of flow of a native valve). For example, an approach to a mitral valve may be transseptal (e.g., from the right atrium to the left atrium through a transseptal puncture) and then in a ventricular direction towards the mitral valve. The implant 10 accordingly has a direction of flow that would be in a ventricular direction, and thus is opposite the direction represented in FIGS. 18-20.

In embodiments, other approaches may utilize the orientation of the implant 10 shown in FIGS. 54-56. For example, a transapical approach or other approach requiring an opposite orientation of the implant 10 than represented in FIGS. 18-20 may be utilized.

Other methods of crimping the implant 10 to the delivery apparatus may be utilized as desired. In embodiments, a user may be able to select whether to insert the support body 110 in the proximal opening 94 or the distal opening 106. For example, the proximal opening 94 may be configured for the delivery apparatus to be inserted into the channel through, and the distal opening 106 may be configured for the support body to be inserted into the channel through. Further, the proximal opening 94 may be configured for the delivery apparatus to be inserted into the channel through, and the proximal opening 94 may also be configured for the support body 110 to be inserted into the channel through.

Figure 22:
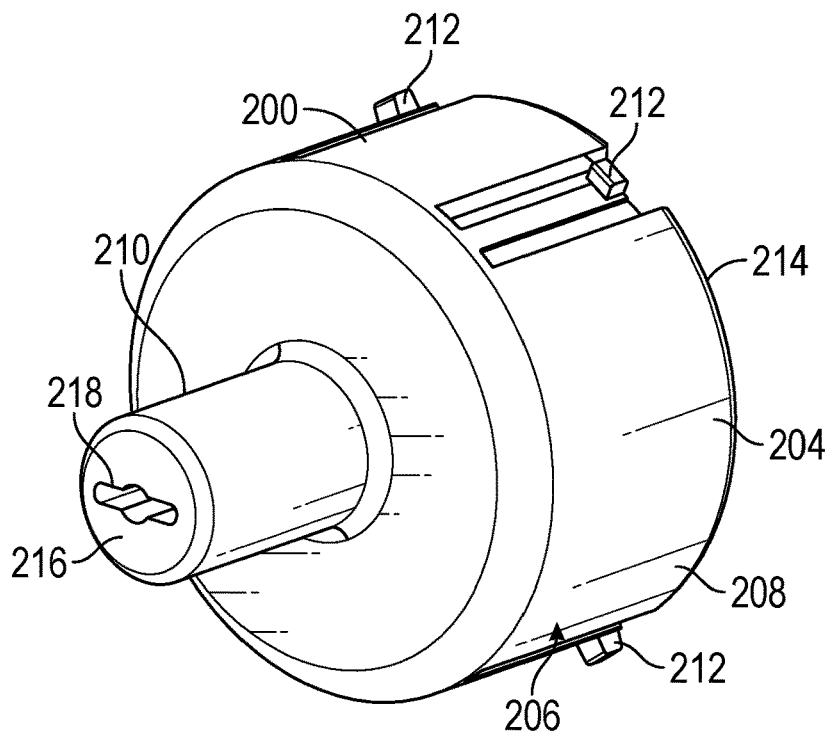
FIG. 22 illustrates a rear perspective view of a stopper housing according to an embodiment of the present disclosure.

FIG. 22 illustrates an embodiment of a stopper housing 200 according to an embodiment of the present disclosure. The stopper housing 200 may comprise a system for use in crimping a prosthetic implant 10 to a delivery apparatus 44. The stopper housing 200 may include a cavity 202 marked in FIGS. 23 and 24 that may be configured to receive a portion of the delivery apparatus 44 distal of the implant retention area 54 of the delivery apparatus 44. The stopper housing 200 may include a contact surface 224 (marked in FIG. 24) configured to abut the delivery apparatus 44 to impede axially distal movement of the delivery apparatus 44 when the delivery apparatus 44 is positioned within a crimping device 84 configured to crimp the prosthetic implant 10 to the delivery apparatus 44. The stopper housing may comprise a crimp stopper housing or crimp assist device according to embodiments.

FIG. 22 illustrates a distal perspective view of the stopper housing 200. The stopper housing 200 may comprise a body 204 having an outer surface 206 and having a large diameter proximal portion 208 and a smaller diameter distal portion 210. The outer surface 206 of the body 204 may include one or more couplers 212 that are configured to couple the stopper housing 200 to a portion of the crimping device 84. The couplers 212, for example, may comprise protrusions extending radially outward from the proximal portion 208 and positioned at a proximal end 214 of the proximal portion 208. The protrusions may extend from arms extending axially along the body 204.

Figure 25:
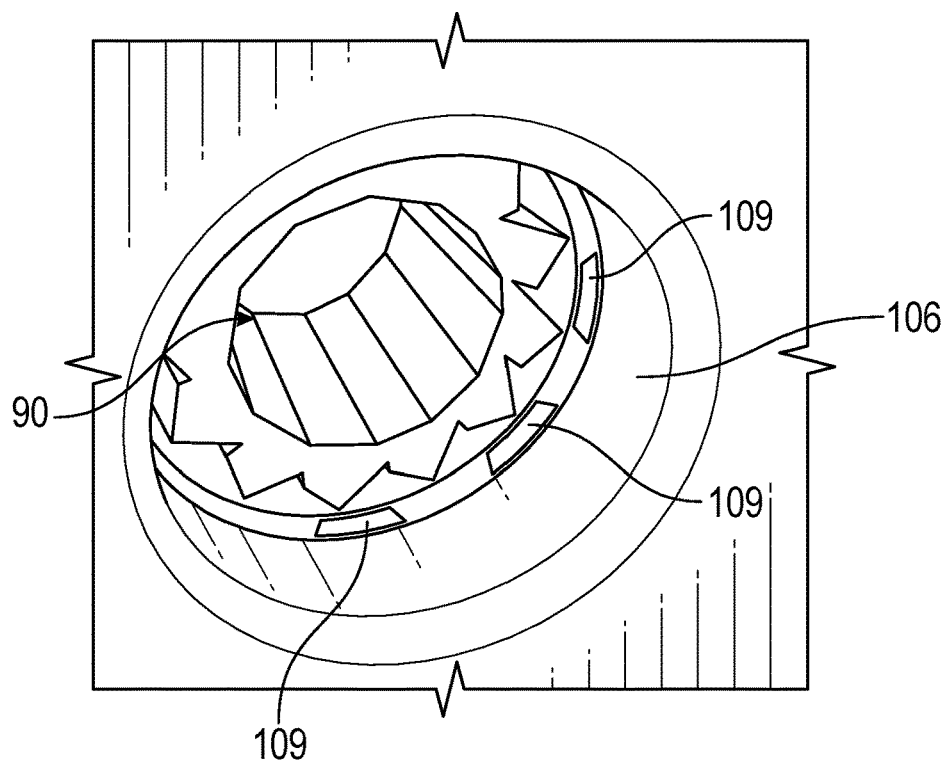
FIG. 25 illustrates a front perspective view of a crimping device according to an embodiment of the present disclosure.

In embodiments, the couplers 212 may be configured to selectively engage a portion of the crimping device 84. For example, the couplers 212 may be configured to deflect radially inward to allow the stopper housing 200 to be engaged or disengaged from the crimping device 84. The couplers 212 may be configured to deflect radially outward to allow the stopper housing to remain engaged to the crimping device 84. FIG. 25, for example, illustrates a perspective view of the distal opening 106 of the crimping device 84. The crimping device 84 may include a plurality of receivers 109 circumferentially spaced about the opening of the channel 90 that may be configured for the couplers 212 to be passed into, to engage the stopper housing 200 to the crimping device 84. In embodiments, other forms of coupling may be utilized.

A distal end 216 of the stopper housing 200 may include an opening 218 for a portion of the delivery apparatus 44 to pass through. For example, the distal tip of the delivery apparatus 44 may be configured to pass through the opening 218 either fully or partially.

Figure 23:
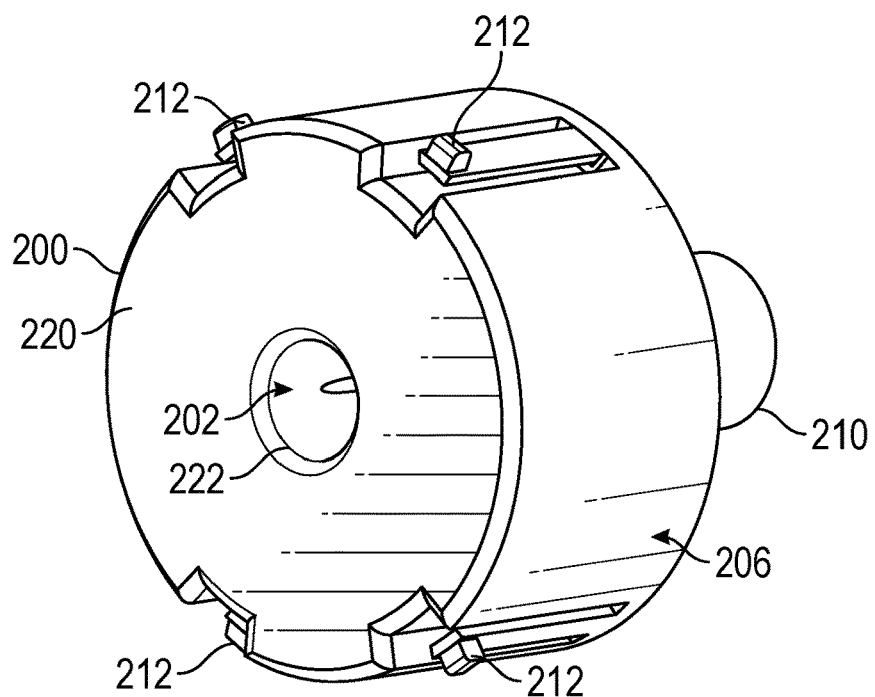
FIG. 23 illustrates a front perspective view of the stopper housing shown in FIG. 22.

FIG. 23 illustrates a proximal perspective view of the stopper housing 200. The stopper housing may include a distal face 220 extending to the outer surface 206 of the stopper housing 200. The cavity 202 may extend distally from the distal face 220 of the stopper housing 200 and may extend from an opening 222 in the distal face 220.

Figure 24:
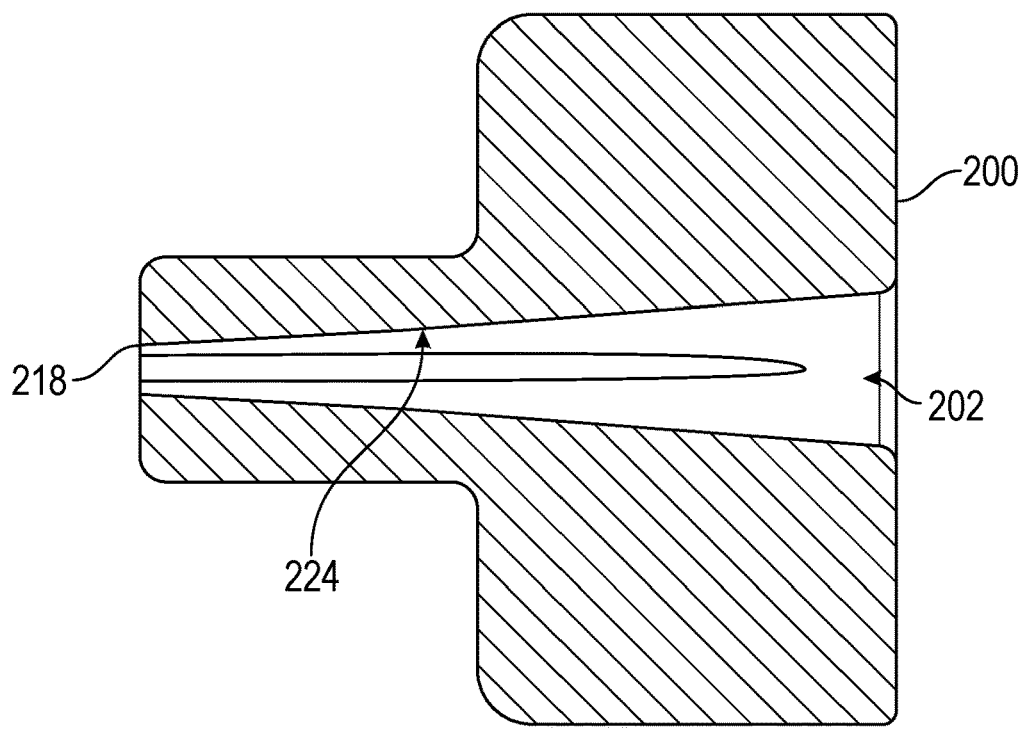
FIG. 24 illustrates a side cross sectional view of the stopper housing shown in FIG. 22.

FIG. 24 illustrates a cross sectional view of the stopper housing 200. The stopper housing may include the contact surface 224. The contact surface 224 in embodiments may comprise an interior surface of the cavity 202, and may define the shape of the cavity 202. The interior surface of the cavity 202 may be angled in embodiments, and may have a tapered shape as shown in FIG. 24. The interior surface 224 and accordingly the cavity 202 may be shaped to contour to the shape of the delivery apparatus, which may include the shape of a distal tip of the delivery apparatus 44. As such, the cavity 202 may be configured to receive the distal tip of the delivery apparatus 44 with the contact surface 224 abutting the distal tip at a certain point of distal insertion of the delivery apparatus 44. The contact surface 224 accordingly may impede distal movement of the distal tip of the delivery apparatus 44. The contact surface 224 may be shaped to impede the distal movement of the distal tip of the delivery apparatus 44 at a certain point that positions the delivery apparatus 44 at a desired position within the channel 90 of the crimping device 84.

In embodiments, the contact surface 224 may be shaped to impede distal movement of the distal tip of the delivery apparatus at a point at which the distal shoulder 70 of the interior shaft 68 (marked in FIG. 5) is positioned distal of the pressing surfaces 100 and outside of the channel 90. The contact surface 224 may be configured to abut the delivery apparatus to impede axially distal movement of the delivery apparatus within then channel 90 of the crimping device 84 to define a position of the delivery apparatus within the channel 90, with a distal shoulder 70 of the delivery apparatus 44 being positioned distal of the channel 90 and external to the channel 90. Such a feature may allow the distal shoulder 70 of the interior shaft 68 not to be compressed during crimping of the implant 10 and thus not to be damaged during a crimping process. The distal shoulder 70 accordingly may remain able to shield the leading edge of the implant 10 (such as the distal end 14 of the implant 10). The contact surface 224 accordingly may serve as a stopping point or datum that positions the distal shoulder 70 distal of the pressing surfaces 100 and outside of the channel 90.

In embodiments, the cavity 202 may be configured to receive the distal shoulder 70 of the delivery apparatus, such that the distal shoulder 70 is positioned within the cavity 202 during crimping. The distal shoulder 70 may be positioned within the cavity 202 in embodiments or may be positioned proximal of the cavity 202 in embodiments. Other configurations may be utilized as desired. Further, in embodiments, the contact surface providing the stopping point or datum may be positioned exterior to a cavity 202 for receiving the delivery apparatus.

FIG. 25 illustrates a distal perspective view of the distal opening 106, illustrating the receivers 109 positioned circumferentially about the opening 106. The receivers 109 may be configured to engage the couplers 212 shown in FIG. 23 to engage the stopper housing 200 to the crimping device 84.

Figure 26:
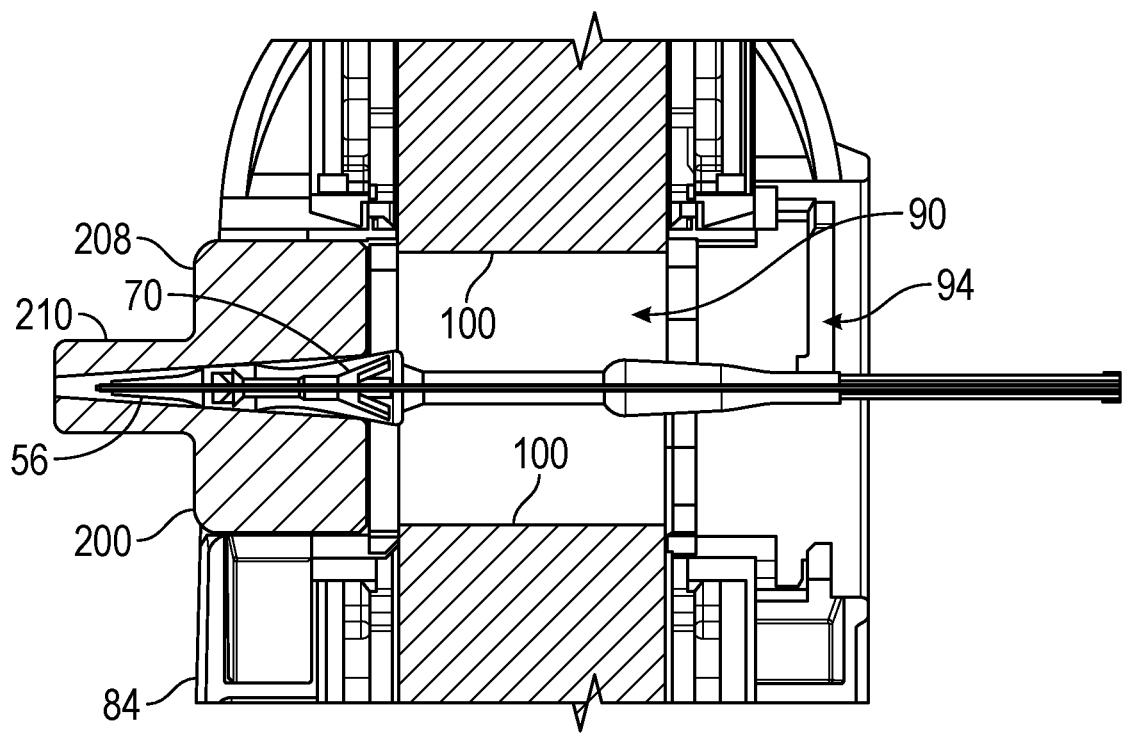
FIG. 26 illustrates a side cross sectional view of the stopper housing shown in FIG. 22 coupled to a crimping device according to an embodiment of the present disclosure.

FIG. 26 illustrates a side cross sectional view of the stopper housing 200 engaged to the crimping device 84. The stopper housing 200 may be positioned on the distal side of the crimping device 84 at the distal opening and may be coupled to the distal opening of the crimping device 84. The stopper housing 200 may be positioned with the cavity 202 positioned axially with respect to the channel 90. The delivery apparatus 44 is shown extending within the channel 90 and is inserted distally into the cavity 202.

In operation, the implant may be inserted into the channel 90 of the crimping device 84. The stopper housing 200 may be coupled to the crimping device 84 distal of the channel 90 on the distal side of the crimping device 84. The delivery apparatus 44 may then be inserted into the channel 90 distally, through the proximal opening 94 of the crimping device. The delivery apparatus 44 may be advanced axially distal through the channel towards the distal opening. A portion of the delivery apparatus 44 distal of the implant retention area 54 may be abutted against the stopper housing 200 to define the position of the delivery apparatus 44 within the channel 90 of the crimping device 84. The delivery apparatus 44 may be inserted distally until the distal tip of the delivery apparatus 44 abuts the contact surface 224 (marked in FIG. 24) of the stopper housing 200. The position at which the delivery apparatus 44 abuts the interior contact surface 224 may position the distal shoulder 70 distal of the pressing surfaces 100 and external to the channel 90. As such, the distal shoulder 70 may be positioned to avoid compression by the pressing surfaces 100.

The pressing surfaces 100 may be pressed to the implant 10 and the implant 10 may be crimped to the delivery apparatus 44. The delivery apparatus 44 may then be retracted proximally from the proximal opening 94 with the implant 10 crimped to the apparatus 44. The stopper housing 200 may be disengaged from the crimping device 84 in a distal direction if desired. The couplers 212 as shown in FIG. 23 may disengage from the crimping device 84.

Notably, a proximal positioning device 172 as shown in FIG. 19 for example, may be excluded from use if desired. The contact surface 224 of the stopper housing 200 may define the axial position of the delivery apparatus 44 within the channel 90 and thus the positioning device 172 may be excluded from use. In embodiments, however, a proximal positioning device 172 may be utilized to suspend the shaft of the delivery apparatus 44 within the channel 90.

The contour of the contact surface 224 may be defined based on the type of delivery apparatus 44 to be utilized, and the desired position of the delivery apparatus 44 within the channel 90. For example, a narrower cavity 202 defined by the contact surface 224 may position the delivery apparatus further in the proximal direction, and a wider cavity 202 may position the delivery apparatus further in the distal direction because the delivery apparatus 44 may pass further through the stopper housing 200. Other configurations of contact surfaces 224 may be utilized as desired.

In embodiments, a stopper housing 200 may be used in combination with the embodiment shown in FIGS. 54-56. For example, the stopper housing 200 may be positioned at the distal side of the crimping device 84, and the support body 110 may be positioned at the proximal side of the crimping device 84 as shown in FIG. 55 for example. The stopper housing 200 may be utilized to position the elongate shaft 46 at a desired position within the channel 90 and to position the implant 10 as desired relative to the implant retention area 54. The crimping procedure may then proceed as shown in FIG. 56 for example.

Figure 27:
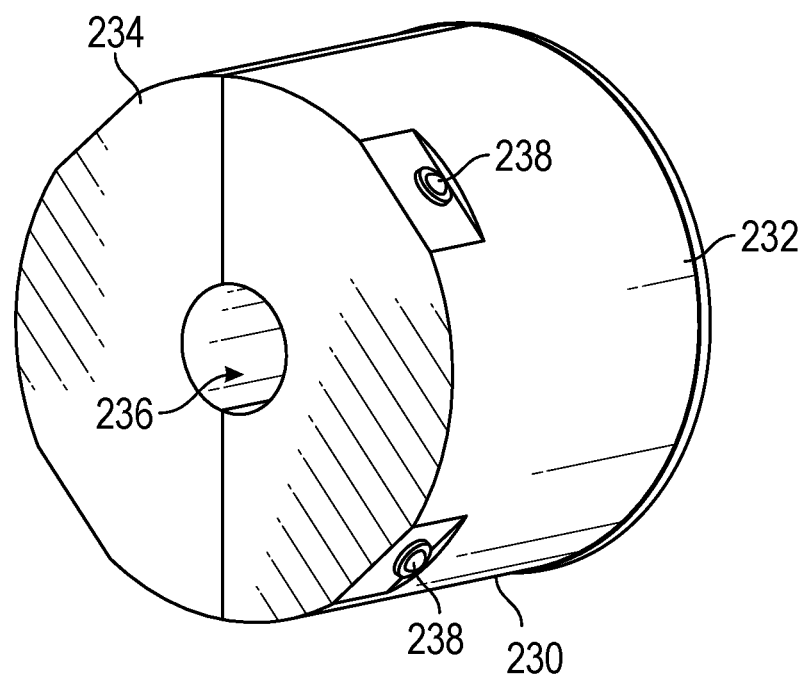
FIG. 27 illustrates a front perspective view of a stopper housing according to an embodiment of the present disclosure.

Variations in the stopper housing may be utilized. FIG. 27, for example, illustrates a proximal perspective view of a stopper housing 230 including two separable bodies 232, 234 that may separate to open the cavity 236. The stopper housing 200 shown in FIG. 22 may be split to include separable bodies as well. Such a feature may allow the stopper housing to be assembled onto the distal tip of the delivery apparatus to secure a position of the stopper housing upon the delivery apparatus.

The stopper housing 230 may further include couplers 238 in the form of spring biased protrusions that are configured to spring outward to insert into retainers of the crimping device 84 and are configured to retract to allow the stopper housing 230 to be removed from the crimping device 84. The stopper housing 230 may operate in a similar manner as the stopper housing 200 shown in FIG. 26.

Figure 28:
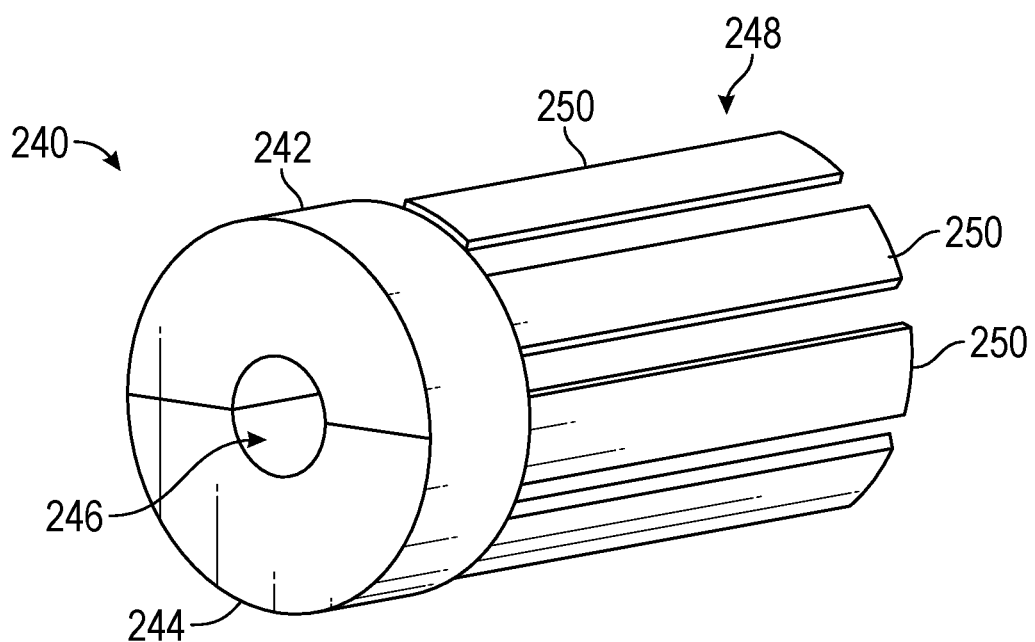
FIG. 28 illustrates a rear perspective view of a stopper housing according to an embodiment of the present disclosure.

FIG. 28 illustrates a distal perspective view of embodiment of a stopper housing 240 including two separable bodies 242, 244 surrounding an interior channel 246, similar to the stopper housing 232 shown in FIG. 27. The stopper housing 240, however, may include a proximal portion 248 including a plurality of compression arms 250 configured to extend within the channel 90 of the crimping device 84 and have the pressing surfaces 100 applied to the compression arms 250. The compression arms 250 may extend over the implant 10 and press against the implant 10 to crimp the implant 10 to the delivery apparatus 44. The compression arms 250 accordingly may serve to assist in crimping the implant 10 to the delivery apparatus 44. The proximal portion 248 may be separable from the bodies 242, 244 in embodiments.

The stopper housings may beneficially provide a datum or stopping point to impede distal axial movement of the delivery apparatus 44 and position the delivery apparatus 44 axially in a desired position within the crimping device 84. The delivery apparatus 44 may be positioned with the distal shoulder 70 distal of the pressing surfaces 100 and exterior of the channel 90. As such, the distal shoulder 70 may be positioned to avoid compression by the pressing surfaces 100. The stopper housings in embodiments may be selectively coupled to the crimping device 84 as desired.

The embodiments of stopper housings may be utilized solely, or in combination with other components disclosed herein. The configurations of stopper housings may vary from the embodiments disclosed herein.

Figure 29:
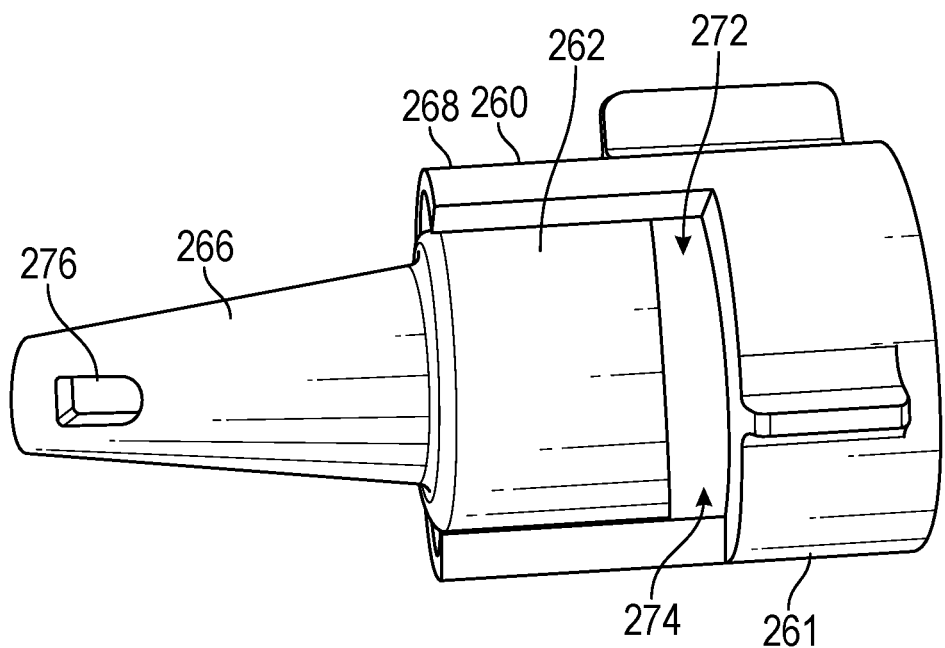
FIG. 29 illustrates a side view of a spacer body according to an embodiment of the present disclosure.

FIG. 29 illustrates an embodiment of a spacer body 260 according to an embodiment of the present disclosure. The spacer body 260 may be configured to extend over a portion of a delivery apparatus 44 distal of the implant retention area 54 of the delivery apparatus 44 and may include a contact surface 264 (marked in FIG. 30) for a distal end of an implant 10 to abut to define a position of the implant 10 upon the delivery apparatus 44.

The spacer body 260 may include a proximal portion 262 and may include a distal portion 266. The spacer body 260 may include an outer surface 268 that may be configured to be grasped by a user. The proximal portion 262 may include a plurality of cavities, each having a different size.

Figure 30:
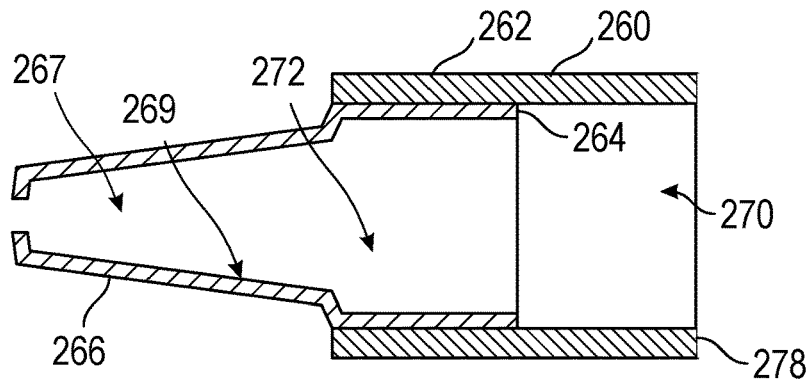
FIG. 30 illustrates a cross sectional view of the spacer body shown in FIG. 29.

FIG. 30, for example, illustrates a cross sectional view of the spacer body 260. The proximal portion 262 may include a proximal cavity 270 that may be sized to receive a crimped implant 10. The proximal portion 262 may further include a distal cavity 272 may be sized to receive a portion of the delivery apparatus 44 distal of the implant retention area 54, which may comprise the distal tip of the delivery apparatus 44. The cavity 272 may be configured to receive a distal shoulder 70 of the delivery apparatus in embodiments. The contact surface 264 may be positioned between the distal cavity 272 and the proximal cavity 270 of the proximal portion 262.

The proximal portion 262 may include an opening or window 274 (marked in FIG. 29) that may allow a user to view the implant 10 within the proximal cavity 270 and abutting the contact surface 264.

Referring to FIG. 30, the distal portion 266 may include a cavity 267 that comprises a continuation of the distal cavity 272 of the proximal portion 262. The cavity 267 of the distal portion 266 in embodiments may be sized to receive a portion of the delivery apparatus 44 distal of the implant retention area 54, such as the distal tip of the delivery apparatus 44. The cavity 267 may be sized to prevent distal movement of the distal tip. The distal portion 266 may further include an opening or window 276 (marked in FIG. 29) that may allow a user to view the distal tip positioned within the cavity 267 of the distal portion 266.

The contact surface 264 marked in FIG. 30 may comprise a first contact surface, and the spacer body 260 may include a second contact surface 269 that is configured to abut a portion of the delivery apparatus such as a distal tip of the delivery apparatus 44. The second contact surface 269 may be contoured to impede distal movement of the delivery apparatus 44, in a similar manner as the contact surface 224 of the stopper housing 200 shown in FIG. 24 for example. The second contact surface 269, for example, may be an interior surface of one or more of the cavities 272, 267 and may be contoured to abut the distal portion of the delivery apparatus such as the distal tip.

Figure 38:
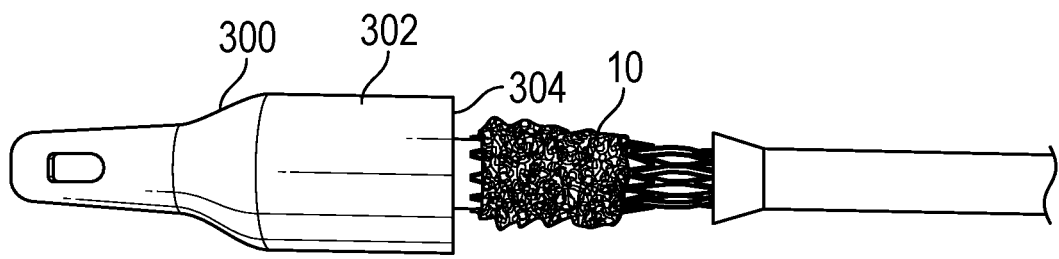
FIG. 38 illustrates a side view of a spacer body according to an embodiment of the present disclosure.
Figure 39:
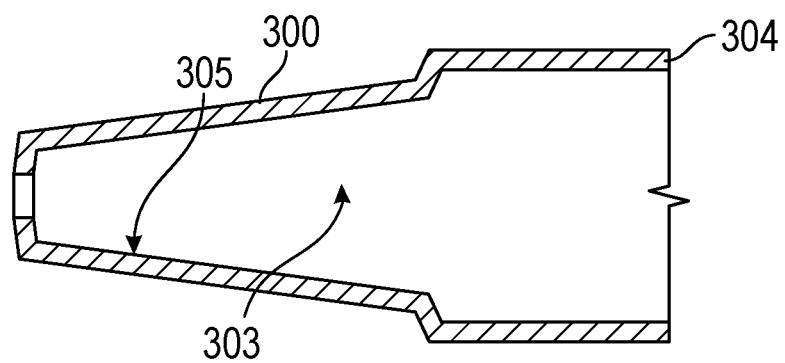
FIG. 39 illustrates a side cross sectional view of the spacer body shown in FIG. 38.

The first contact surface 264, may be positioned outside of and proximal of the cavities 272, 267, and may extend around a longitudinal axis of the spacer body 260. The first contact surface 264 may extend transverse to the longitudinal axis and may extend perpendicular as shown in FIG. 30. The first contact surface 264 may be positioned distal of the proximal face 278 of the spacer body 260 as shown in FIG. 30, or may comprise the proximal face of the spacer body, as shown in the embodiments of FIGS. 38 and 39 for example.

Figure 31:
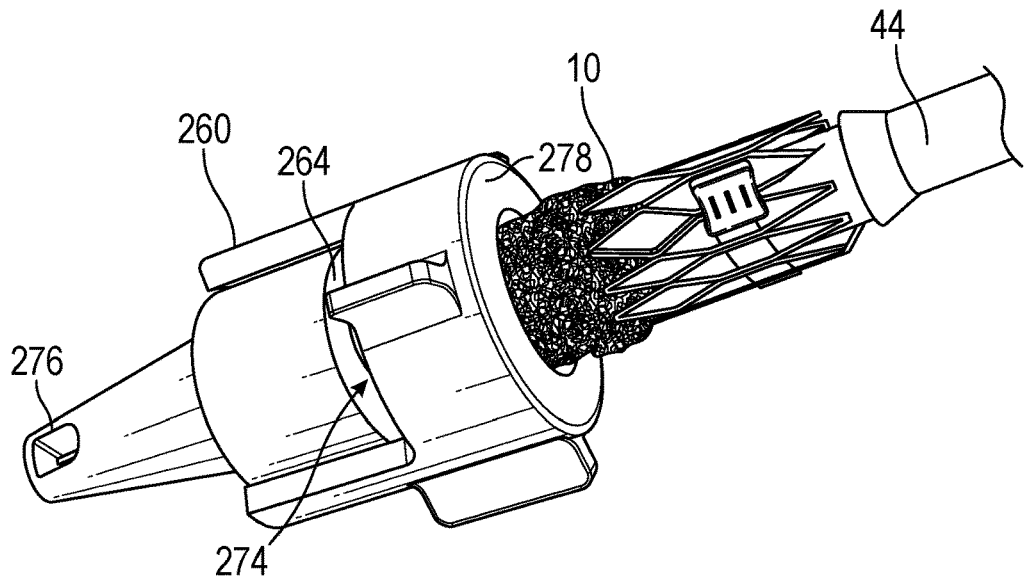
FIG. 31 illustrates a side perspective view of the spacer body shown in FIG. 29, with a partially crimped implant positioned within the spacer body.

Referring to FIG. 31, the delivery apparatus 44, with the implant 10 positioned thereon in an uncrimped or partially crimped state, may be inserted distally into the proximal cavity 270 and distal cavities 272, 267 of the spacer body 260 until the delivery apparatus 44 contacts the contact surface 269 of one or more of the cavities 272, 267 (as marked in FIG. 30) and is thus impeded from further distal movement. The position of the spacer body 260 upon the delivery apparatus 44 may thus be defined.

The implant 10, in an uncrimped or partially crimped state, may then be advanced distally along the delivery apparatus 44 until the implant 10 contacts the contact surface 264. The contact of the implant 10 to the contact surface 264 may define the position of the implant 10 upon the delivery apparatus 44. As such, the implant 10 may be placed in a desired position upon the delivery apparatus 44. The delivery apparatus 44 may remain in contact with the interior contact surface 269 and the implant 10 may remain in contact with the transverse contact surface 264 to maintain the desired position of the implant 10 upon the delivery apparatus 44.

A method of utilizing the spacer body 260 may include first placing the implant 10 within the crimping device 84. The implant 10 may be covered with a cushioning body such as Qualcrimp® or another form of cushioning body. The implant 10 may be placed within the channel 90 of the crimping device 84 and may be partially crimped by the crimping device 84. In embodiments, the implant 10 may be positioned on the delivery apparatus 44, although in other embodiments the implant 10 may not be positioned upon a delivery apparatus during such a pre-crimping procedure.

The cushioning body may be removed from the partially crimped implant 10. The partially crimped implant 10 may be crimped to a diameter that allows the implant 10 to fit within the proximal cavity 270 (marked in FIG. 30) of the spacer body 260. The spacer body 260 may then be positioned over the delivery apparatus 44 by being slid over the distal tip of the delivery apparatus 44 with the distal tip entering the cavities 272, 267 of the proximal portion 262 and the distal portion 266 respectively. The spacer body 260 may be positioned over a portion of the delivery apparatus 44 distal of the implant retention area 54 of the delivery apparatus 44. FIG. 31, for example, illustrates the delivery apparatus 44 and the implant 10 being inserted into the spacer body 260.

Figure 32:
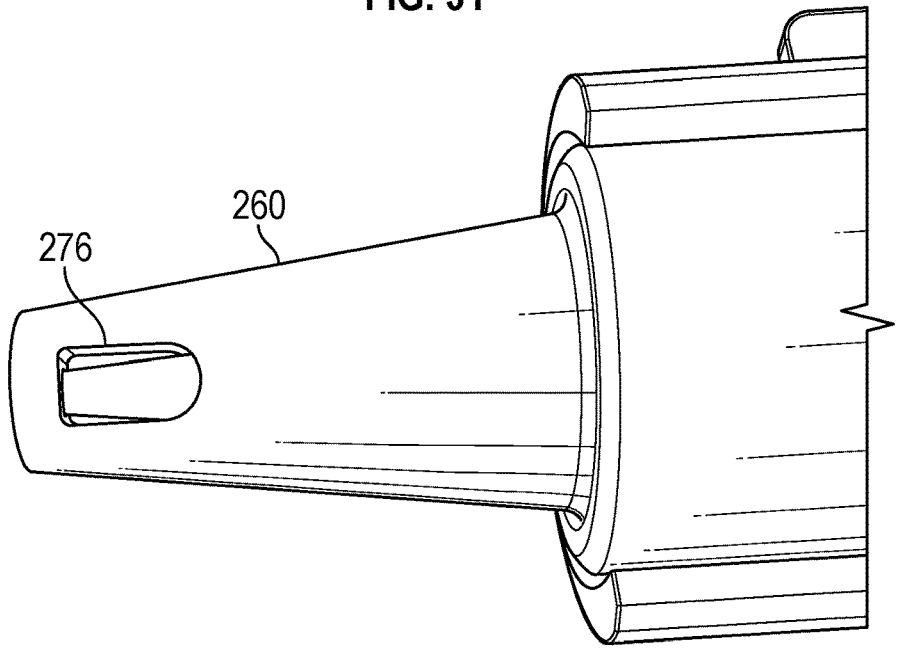
FIG. 32 illustrates a side view of a nose cone positioned within the spacer body shown in FIG. 29.

The distal tip may be inserted distally until the distal tip contacts the interior contact surface 269 of the cavity of the distal portion 266 (as marked in FIG. 30). A user may view the distal tip in position through the window 276 of the distal portion 266. FIG. 32, for example, illustrates the distal tip in position and visible through the window 276 of the distal portion 266. A user may thus confirm the delivery apparatus 44 is in the desired position with respect to the spacer body 260.

Figure 33:
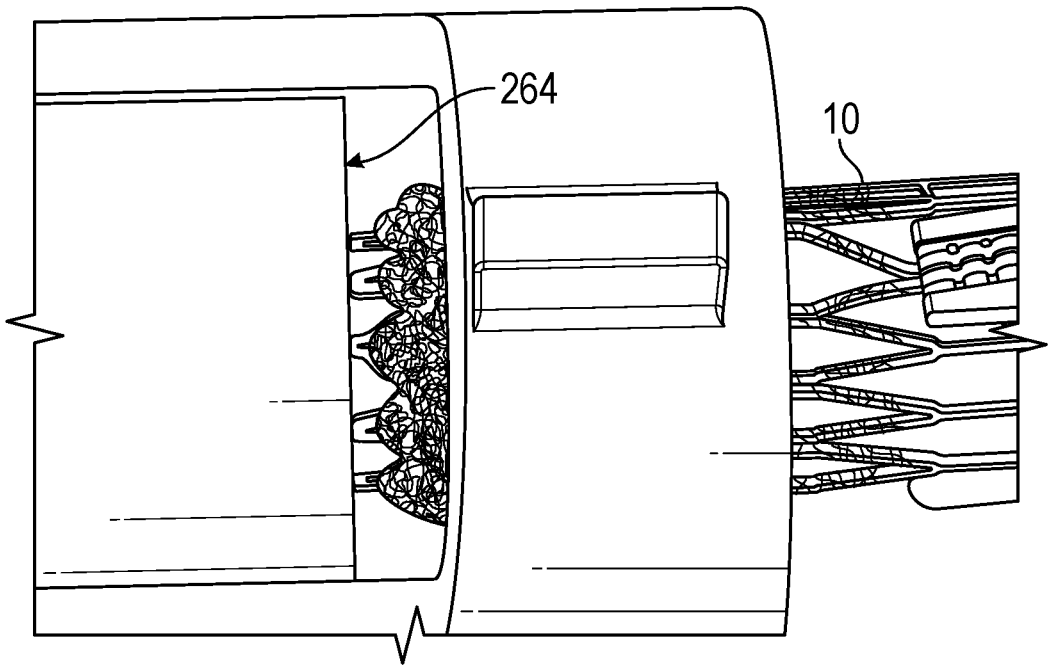
FIG. 33 illustrates a side view of a partially crimped implant positioned within the spacer body shown in FIG. 29.

The partially crimped implant 10 may be inserted distally into the proximal cavity 270 until the distal end of the implant 10 abuts the contact surface 264. The abutment of the distal end against the contact surface 264 defines the position of the implant 10 upon the delivery apparatus 44. FIG. 33, for example, illustrates the implant 10 in contact with the contact surface 264 and within the proximal cavity 270. With the spacer body 260 at a defined position upon the delivery apparatus 44, the partially crimped implant 10 may be placed at a defined position as well. The defined position may be a desired location upon the implant retention area of the delivery apparatus 44. In embodiments, the defined position may be at a marker band or other imaging marker of the delivery apparatus 44 that defines a desired location of the implant 10.

Figure 34:
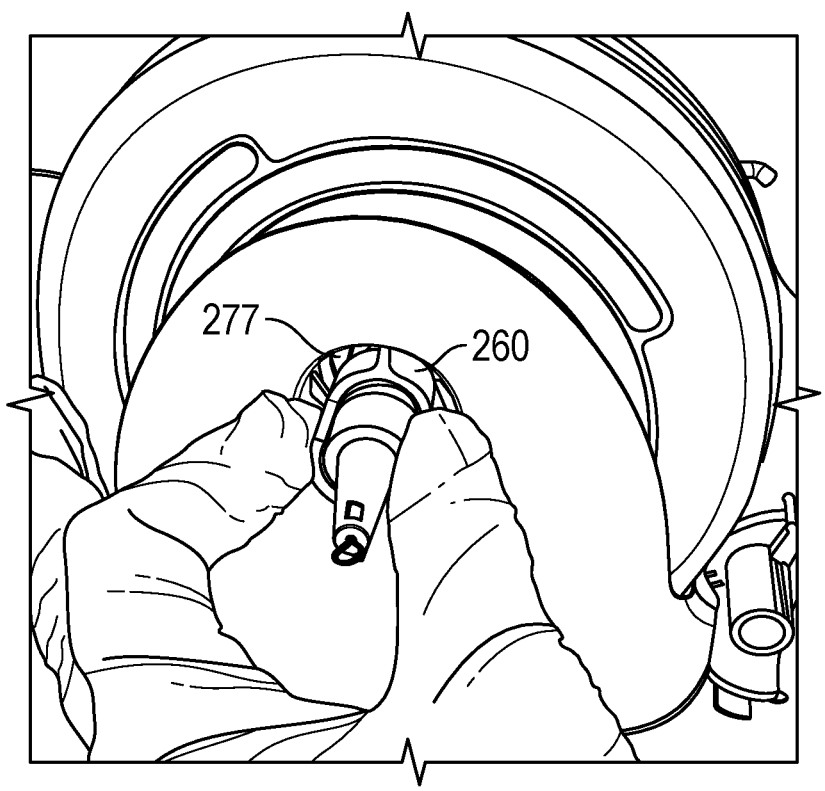
FIG. 34 illustrates the spacer body shown in FIG. 29 positioned against a crimping device according to an embodiment of the present disclosure.

With the implant 10 in position abutting the contact surface 264, the spacer body 260 and delivery apparatus 44 with the implant 10 remaining in contact with the contact surface 264 may be inserted distally through the proximal opening 94 of the crimping device 84, as shown in FIG. 6. The spacer body 260, delivery apparatus 44, and implant 10 may continue to pass distally through the channel 90 of the crimping device 84 until the spacer body 260 is positioned distal of the pressing surfaces 100. FIG. 34, for example, illustrates the spacer body 260 positioned distal of the pressing surfaces 100 and at the distal opening of the crimping device 84.

A proximal portion of the spacer body 260 may be held in abutment against the distal facing surface 277 of the bodies comprising the pressing surfaces 100. The delivery apparatus 44, and the implant 10 may remain in position against the spacer body 260 and thus may be held in a defined relationship relative to the pressing surfaces 100.

With the implant 10 in position in the channel 90, the pressing surfaces 100 may crimp the implant 10 either fully or partially. The spacer body 260 may then be removed distally from the delivery apparatus 44. The portion of the implant 10 that was covered by the spacer body 260 may then be crimped to the delivery apparatus 44 to complete the crimping procedure.

Figure 35:
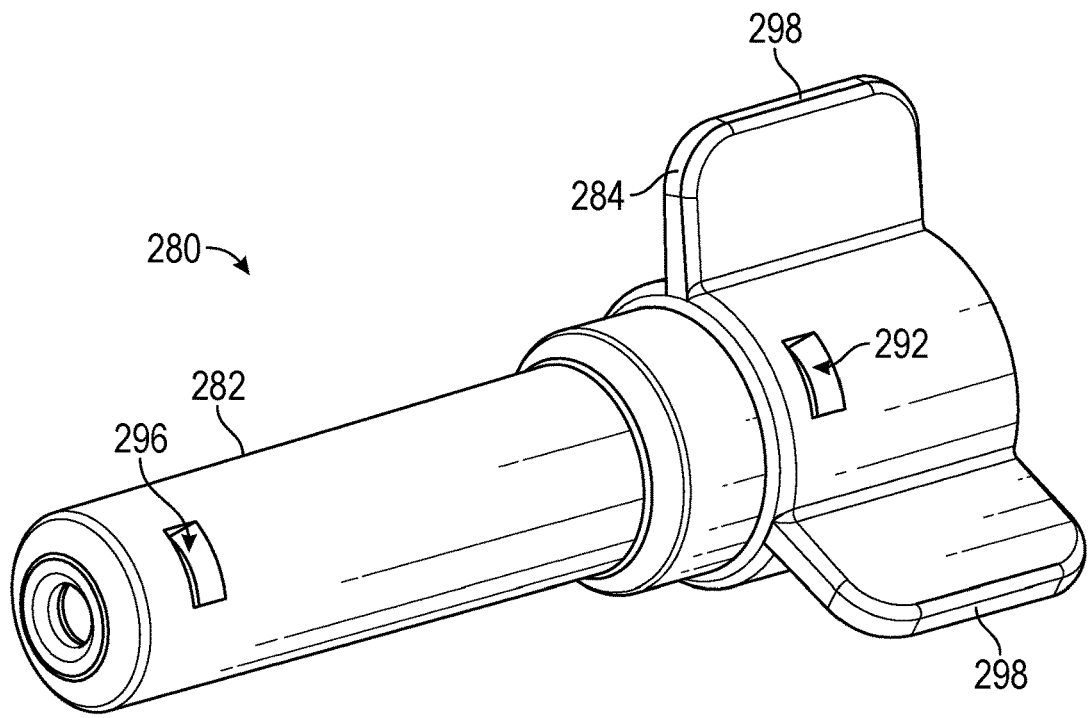
FIG. 35 illustrates a rear perspective view of a spacer body according to an embodiment of the present disclosure.

Variations in the spacer body 260 may be utilized. FIG. 35, for example, illustrates a distal perspective view of a spacer body 280 in which the distal portion 282 has a cylindrical shape. The proximal portion 284 may include a plurality of cavities 286, 288 (marked in FIG. 37) having different sizes, and the distal portion 282 may include a cavity 290 sized smaller than the cavity 288.

The proximal portion 284 may include an opening or window 292 that may be utilized to visualize the contact of the implant 10 upon a contact surface 294. The distal portion 282 may further include an opening or window 296 for viewing the distal tip of the delivery apparatus 44 within the cavity 290, and in abutment with a contact surface 295 of the cavity 290.

The proximal portion 284 may further include flanges 298 that may extend radially outward from the proximal portion 284. The flanges 298 may be utilized for gripping the proximal portion 284 and for positioning the proximal portion within the opening of the distal face of the crimping device 84, for example as shown in FIG. 34.

Figure 36:
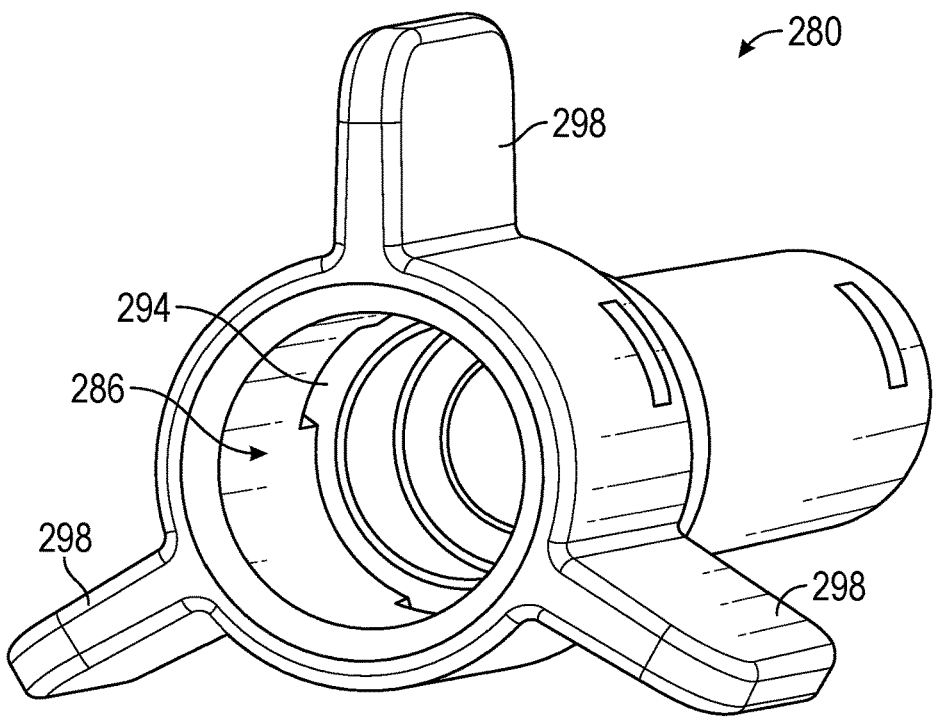
FIG. 36 illustrates a front perspective view of the spacer body shown in FIG. 35.
Figure 37:
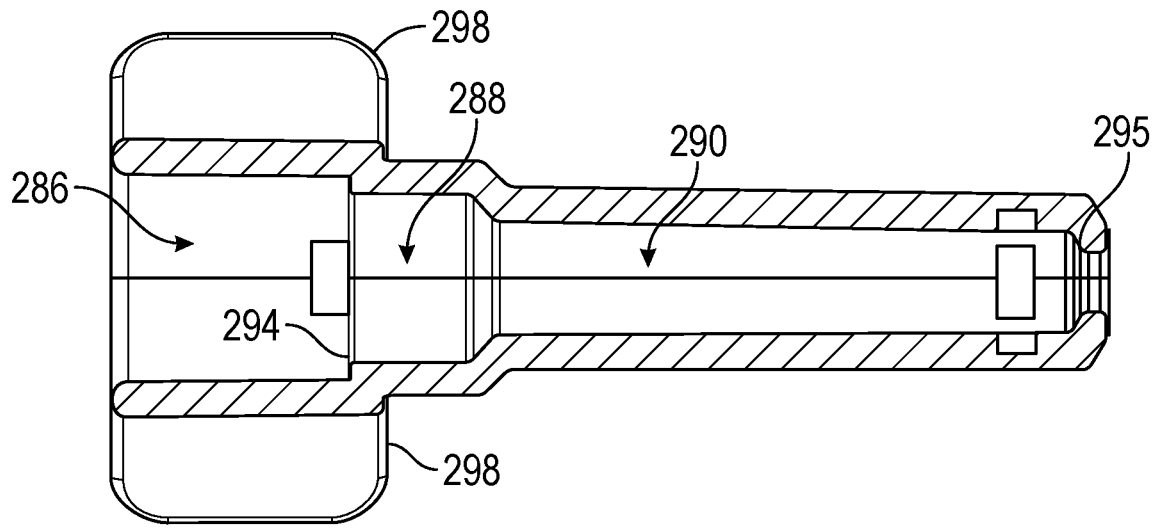
FIG. 37 illustrates a side cross sectional view of the spacer body shown in FIG. 35.

FIG. 36 illustrates a distal perspective view of the spacer body 280. FIG. 37 illustrates a side cross sectional view of the spacer body 280. The contact surface 294 for contacting the distal end of the implant 10 is shown. A contact surface 295 for contacting the distal tip of the delivery apparatus 44 is further shown.

The spacer body 280 may operate in a similar manner as the spacer body 260 shown in FIG. 29.

FIG. 38 illustrates an embodiment of a spacer body 300 in which the proximal portion 302 of the spacer body 300 lacks a housing for extending over the implant 10, similar to the housing 261 shown in FIG. 29. FIG. 39 illustrates a cross sectional view of the spacer body 300 shown in FIG. 38. The implant 10 may abut a contact surface 304 of the spacer body 300 in a similar manner as the implant 10 contacts the contact surface 264 shown in FIG. 30. The spacer body 300 may include a cavity 303 configured to receive a distal portion of a delivery apparatus, and may include an interior contact surface 305 for abutting the distal portion of the delivery apparatus. In an embodiment as shown in FIG. 38, the implant 10 may be fully crimped to the delivery apparatus 44 by the crimping device 84 without the spacer body 300 being removed from the distal tip of the delivery apparatus 44. The spacer body 300 may then be removed from the distal tip after the implant 10 has been fully crimped.

Figure 40:
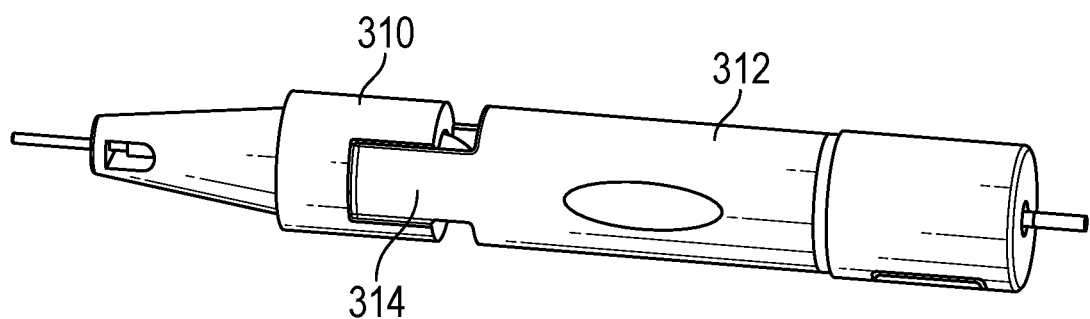
FIG. 40 illustrates a perspective view of a spacer body according to an embodiment of the present disclosure.

FIG. 40 illustrates an embodiment of a spacer body 310 that may be configured similarly as the spacer body 300, yet may include a balloon cover 312 extending proximally from the spacer body 310. The balloon cover 312 may comprise an elongate body that is configured to extend over the balloon 58 (as marked in FIG. 5) to prevent damage to the balloon 58. A coupler 314 may couple the balloon cover 312 to the spacer body 310 and may be configured to be separable from the spacer body 310. For example, the coupler 314 may comprise jaws or another form of coupler that couples the balloon cover 312 to the spacer body 310.

Figure 41:
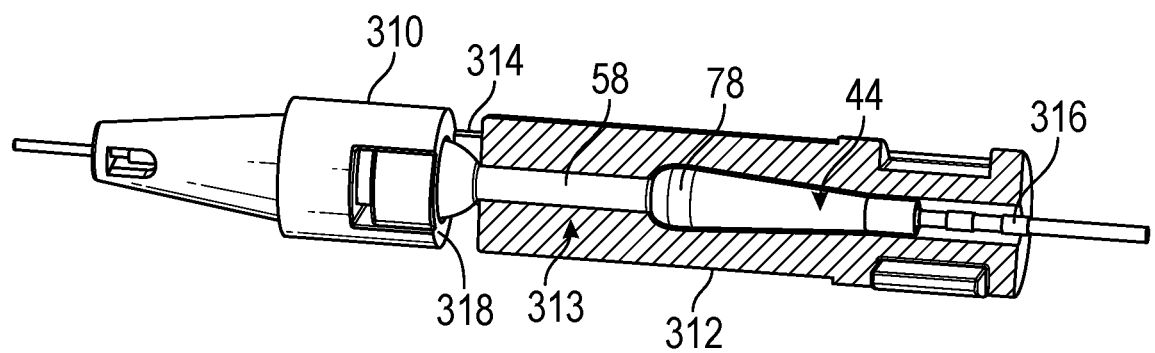
FIG. 41 illustrates a perspective view of the spacer body shown in FIG. 40 with a portion shown in cross section.

FIG. 41 illustrates a cross sectional view of the balloon cover 312, in position over the balloon 58. The balloon cover 312 may include an interior cavity 313 that may be contoured to the shape of the balloon 58, particularly the shape of the proximal shoulder 78 of the balloon 58. The balloon cover 312 may include a proximal opening 316 configured for the delivery apparatus 44 to pass through.

In operation, the spacer body 310 and the balloon cover 312 may be packaged upon the delivery apparatus 44, with the balloon cover 312 extending over the balloon 58. The balloon cover 312 may protect the balloon 58. At a desired time for crimping the implant 10 the balloon 58, the balloon cover 312 may be separated from the spacer body 310 and may be discarded. The implant 10 may then be pressed to the contact surface 318 of the spacer body 310 to position the implant 10 in the desired position relative to the implant retention area 54 of the delivery apparatus 44.

The configurations of the spacer bodies may be varied in embodiments as desired. The embodiments of spacer bodies may be utilized solely, or in combination with other components disclosed herein.

Figure 42:
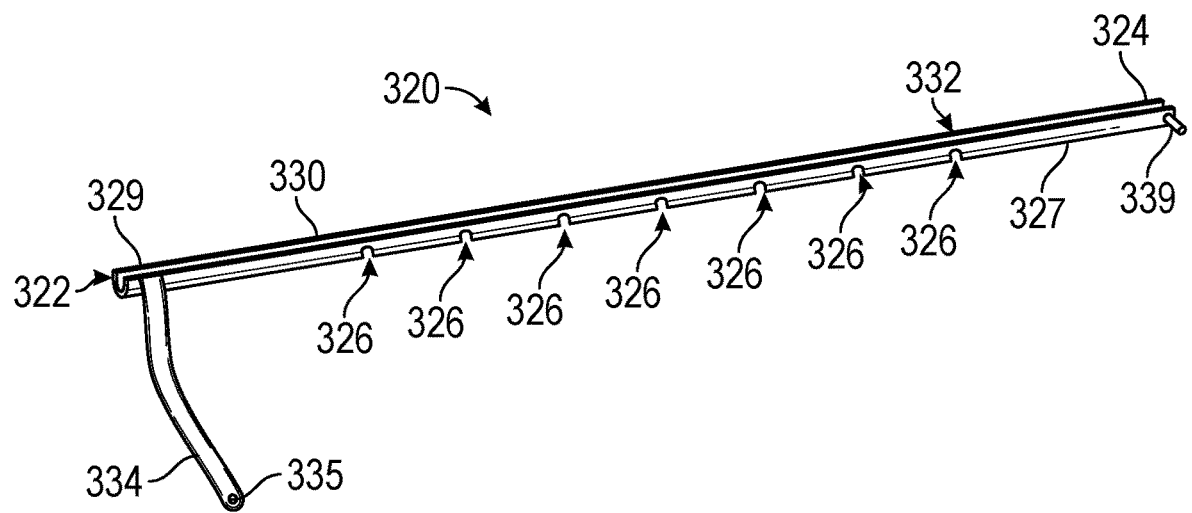
FIG. 42 illustrates a perspective view of an elongate body according to an embodiment of the present disclosure.

FIG. 42 illustrates an elongate body 320 according to an embodiment of the present disclosure. The elongate body 320 may include a channel 322 for receiving the elongate shaft 46 of the delivery apparatus 44. The delivery apparatus 44 may include a proximal portion including the handle 52 and may include a distal portion including the implant retention area 54. The elongate body 320 may be configured to bend in at least one plane to move the distal portion of the delivery apparatus 44 proximate the proximate portion of the delivery apparatus 44.

The elongate body 320 may include a proximal end 324 and a distal end 329 and a length between the ends 324, 329. The elongate body 320 may comprise a sleeve configured to extend along the elongate shaft 46. The elongate body 320 may have walls forming a "U" shape that extends around the channel 322 and may extend along the length of the elongate body 320.

Figure 44:
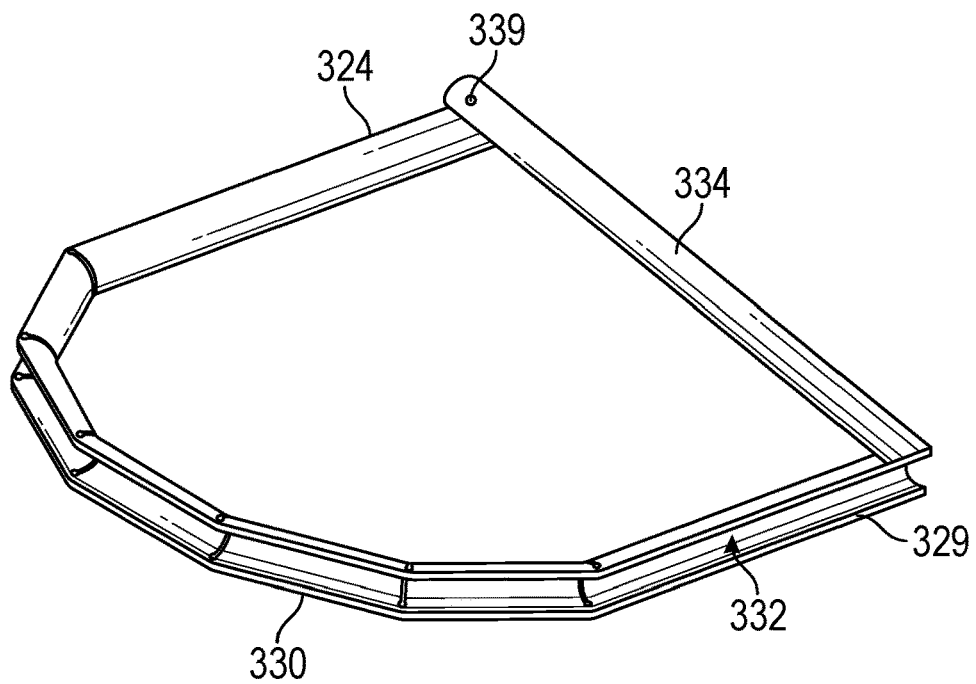
FIG. 44 illustrates a perspective view of the elongate body shown in FIG. 42 in a bent configuration.

The elongate body 320 may be configured to be in a straightened configuration, and be bent in a plane from the straightened configuration to a bent or curved configuration. The elongate body 320 may be bent to bring the ends 324, 329 towards each other and proximate each other. FIG. 44, for example, illustrates the ends 324, 329 having been brought proximate to each other. The elongate body 320 in such a bent configuration may form a "U" shape.

The elongate body 320 may include a plurality of cut out portions 326 that are positioned on a side 327 of the elongate body 320. The cut out portions 326 may be positioned on a side of the elongate body 320 forming an inner curve when the elongate body 320 is bent. The elongate body 320 may be bent such that the cut out portions 326 close and form an inner curve of the elongate body 320.

The cut out portions 326 may be shaped to define a shape of the elongate body 320 in the bent configuration. For example, each cut out portion 326 may have a wedge shape, with an angle of the opposing surfaces 328 being set to define an amount that the elongate body 320 may be bent. The plurality of cut out portions 326 may be configured such that opposing surfaces 328 (marked in FIG. 43) of the cut out portions 326 are configured to be drawn towards each other, and may contact each other, as the elongate body 320 is bent. The opposing surfaces 328 for example, may contact each other to define a radius of curvature of the elongate body 320 in the bent configuration.

Referring to FIG. 42, the cut out portions 326 may be positioned opposite a side 330 of the elongate body 320 that includes an elongate opening 332 forming the opening of the "U" shape of the elongate body 320. The elongate shaft 46 may be inserted into the elongate body 320 by being inserted through the elongate opening 332.

The elongate body 320 may include one or more couplers 334 that may be configured to retain the elongate body 320 in the bent configuration, and couple the ends 324, 329 of the elongate body 320 together when the elongate body 320 is in the bent configuration. The coupler 334 may be in the form of a tether having an opening 335 at an end of the tether, configured to couple to a pin 339 or other device positioned at the proximal end 324 of the elongate body 320. The tether may maintain a distance between the proximal end 324 and the distal end 329 of the elongate body 320 when the elongate body 320 is in the bent configuration.

Figure 43:
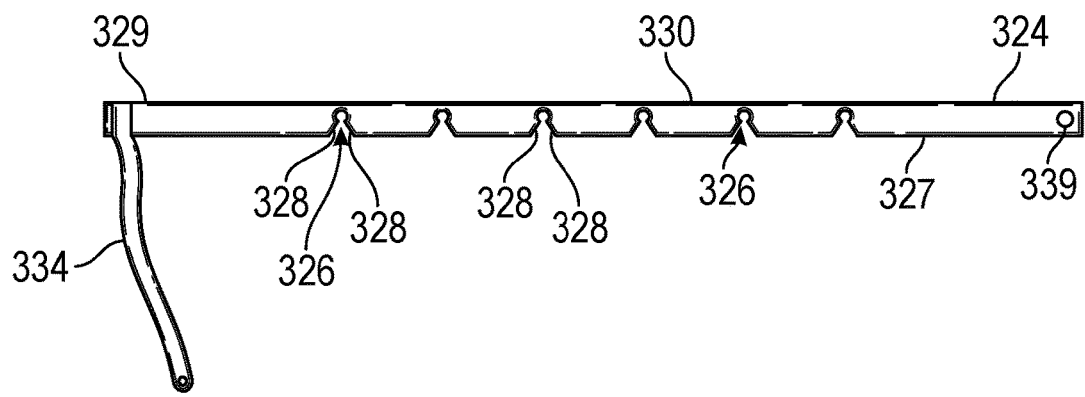
FIG. 43 illustrates a side view of the elongate body shown in FIG. 42.

FIG. 43 illustrates a side view of the elongate body 320. FIG. 44 illustrates a perspective view of the elongate body 320 in the bent configuration. The cut out portions 326 have closed to allow the elongate body 320 to move to the bent configuration. The coupler 334 may extend from the distal end 329 to the proximal end 324 and may be sturdy enough to hold the elongate body 320 in the bent configuration.

Figure 45:
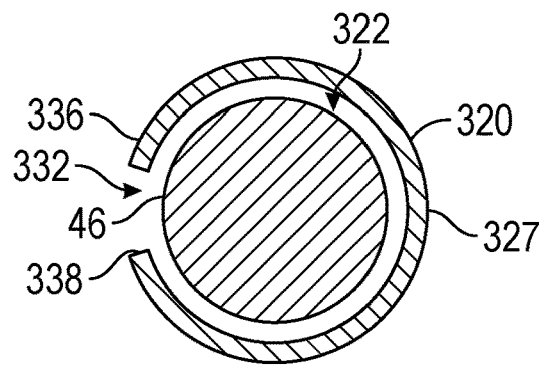
FIG. 45 illustrates a side cross sectional view of a portion of an elongate body according to an embodiment of the present disclosure.

In the bent configuration, the elongate opening 332 extending along the side 330 of the elongate body 320 may form an outer curve, and may close slightly to further enclose a delivery apparatus 44 positioned within the channel 322. FIG. 45, for example, illustrates an elongate shaft 46 positioned within the channel 322 of the elongate body 320, with the size of the opening 332 decreased to slightly close the opening 332 when the body 320 is in the bent configuration. The edges 336, 338 of the walls of the elongate body 320 are drawn towards each other to decrease the size of the opening 332. As such, the walls may serve to retain the elongate shaft 46 of the delivery apparatus 44 within the channel 322.

Figure 46:
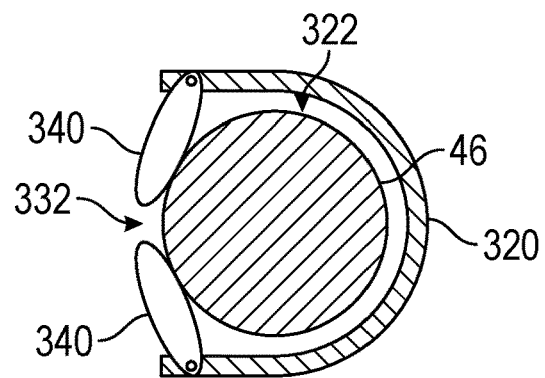
FIG. 46 illustrates a side cross sectional view of a portion of an elongate body according to an embodiment of the present disclosure.

Other methods and devices may be utilized to retain the delivery apparatus 44 within the channel 322. FIG. 46, for example, illustrates an embodiment in which couplers 340 may be utilized that pivot with respect to the elongate opening 332. The couplers 340 may be pivotal couplers configured to pivot open and closed to allow the delivery apparatus 44 to be inserted into the channel 322 and retained within the channel. The couplers 340, for example may comprise lever arms pivotally coupled to the walls of the elongate body 320. A plurality of the couplers 340 may be utilized along the length of the elongate opening 332 as desired.

Figure 47:
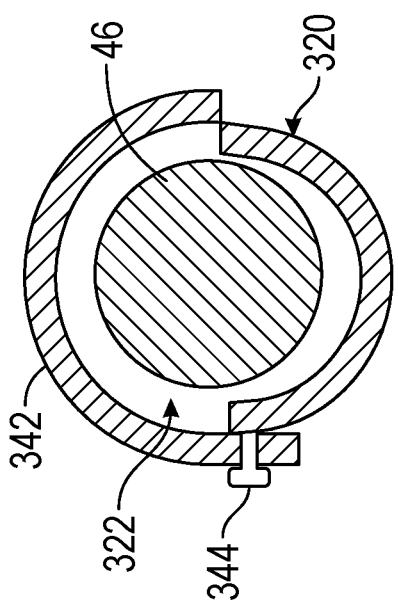
FIG. 47 illustrates a side cross sectional view of a portion of an elongate body according to an embodiment of the present disclosure.

FIG. 47 illustrates an embodiment in which a coupler 342 in the form of a strap may be utilized to retain the delivery apparatus 44 to the elongate body 320. The strap may extend over the elongate opening 332 and may be configured to release and secure to a pin 344 or other coupler that may hold the coupler 342 in a secured position. The coupler 342 may extend over the elongate shaft 46 of the delivery apparatus 44 to hold the delivery apparatus 44 to the elongate body 320.

Figure 52:
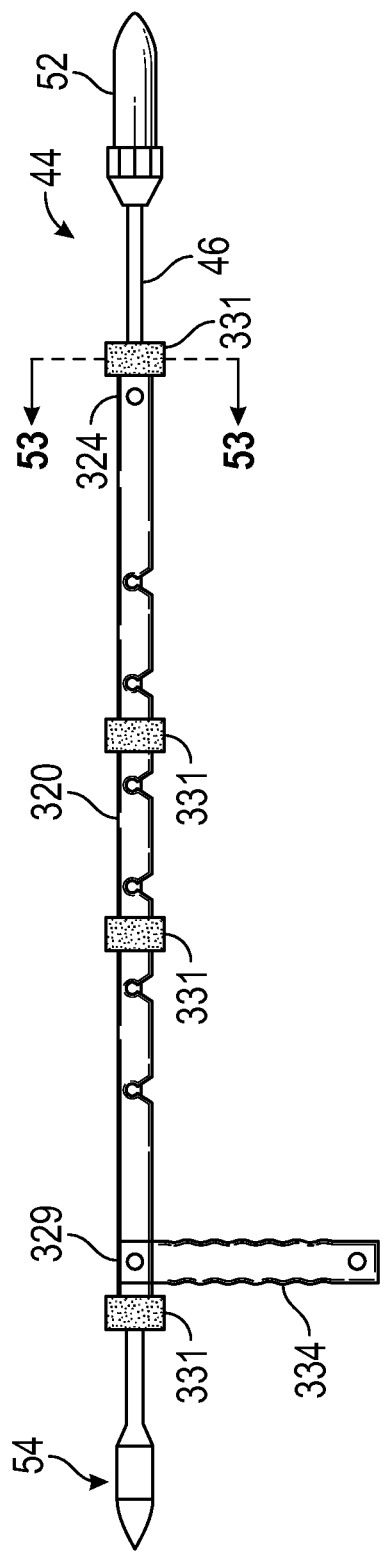
FIG. 52 illustrates a side view of an elongate body according to an embodiment of the present disclosure.

FIG. 52 illustrates an embodiment in which a coupler in the form of a resilient retainer 331 may be utilized to retain the delivery apparatus 44 to the elongate body 320. The resilient retainer 331 may be overmolded or otherwise positioned upon the elongate body 320. One or more retainers 331 may be utilized, such as a retainer at the proximal end 324, the distal end 329, and/or one or more intermediate positions of the elongate body 320 between the proximal end 324 and the distal end 329. For example, as shown, four retainers 331 may be utilized, with one at the proximal end 324, one at the distal end 329, and two positioned between the cut out portions of the elongate body 320. In embodiments, only one retainer 331 may be utilized, or multiple retainers may be utilized as desired.

Figure 53:
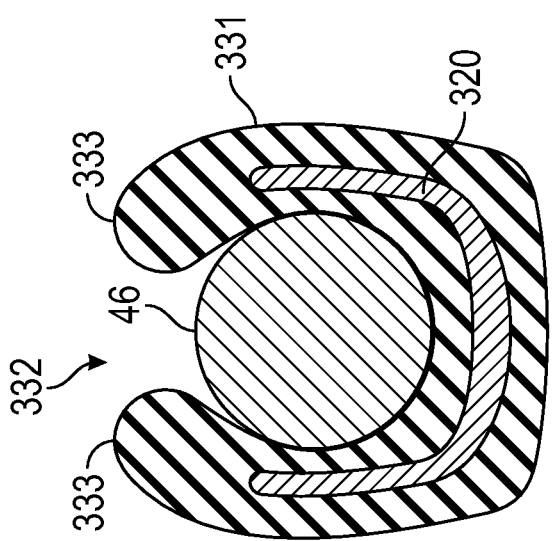
FIG. 53 illustrates a cross sectional view of the elongate body shown in FIG. 52 along line 53-53.

FIG. 53 illustrates a cross sectional view of the elongate body 320 shown in FIG. 52, along line 53-53. The resilient retainer 331 may extend around the elongate body 320 and may cover an interior surface and an outer surface of the elongate body 320. The retainer 331 may be overmolded upon the elongate body 320 to cover the interior surface and the outer surface of the elongate body 320. The retainer 331 may have two ends 333 that are positioned at the elongate opening 332 of the elongate body 320. As such, the elongate shaft 46 may be inserted into the elongate body 320 through the opening 332. The ends 333 of the retainer 331 may bend outward to allow the elongate shaft 46 to be inserted into the channel of the elongate body 320. The ends 333 may then bend inward towards the elongate shaft 46 to grip the elongate shaft 46 within the channel. The ends 333 may form arms that overlap a portion of the elongate shaft 46 to retain the elongate shaft 46 with the channel of the elongate body 320. The ends 333 of the retainer 331 may be spaced from each other as shown in FIG. 53, or may be in contact with each other in embodiments.

To remove the elongate shaft 46 from the resilient retainer 331, the elongate shaft 46 may be pulled out of the elongate opening 332. The ends 333 may bend outward to allow the elongate shaft 46 to exit the channel of the elongate body 320. Other retainers 331 utilized with the elongate body 320 may each be configured similarly and operate in a similar manner.

The retainer 331 may be flexible, to allow the ends 333 to bend outward and inward. The retainer 331 may further be flexible to allow the retainer 331 to cushion the elongate shaft 46 from a force that may be applied to the elongate body 320. The retainer 331 may be made of an elastic material that may be configured to return back to its original shape upon deformation. The material of the retainer 331 may be a rubber material, or in embodiments may be a variety of resilient polymers, or other materials as desired. One or more retainers 331 may be configured to be overmolded upon one or more desired portions of the elongate body 320, such as the ends 324, 329 of the elongate body 320 or intermediate portions. The configuration of the retainer 331 may be varied from the configuration shown in FIGS. 52 and 53 in embodiments.

Other devices and methods may be utilized to couple the delivery apparatus 44 to the elongate body 320 as desired.

Figure 48:
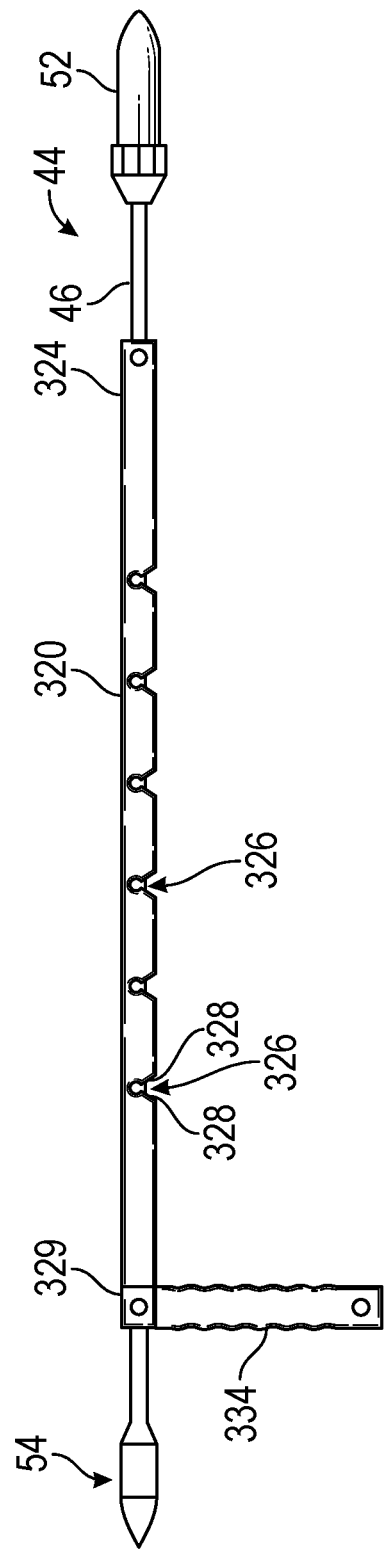
FIG. 48 illustrates a delivery apparatus positioned within an elongate body according to an embodiment of the present disclosure.

In operation, the elongate body 320 may be packaged coupled to the delivery apparatus 44 as the delivery apparatus 44 is provided to a user that may prepare or otherwise utilize the delivery apparatus 44. FIG. 48, for example, illustrates the elongate body 320 coupled to the delivery apparatus 44 with the elongate shaft 46 positioned within the channel 322 of the elongate body 320. The elongate body 320 is in a straightened configuration, with the elongate shaft 46 in the straightened configuration as well. The delivery apparatus 44 may be provided to the user with the elongate body 320 positioned thereon, with both in the straightened configuration.

It may be desirable for the user to position the distal tip, and implant retention area 54 of the elongate shaft 46 proximate the handle 52 and control mechanism of the delivery apparatus 44. Such a feature may be beneficial, for example, if the user desires to perform an operation at the distal end of the delivery apparatus 44 while controlling the control mechanism. For example, if a crimping operation is performed at the distal end of the delivery apparatus 44, the user may desire to control the position of the outer sheath 64 shown in FIG. 5 to either cover or uncover all or a portion of the balloon 58, or the implant 10. The user may otherwise desire to have the proximal end of the delivery apparatus 44 proximate the distal end of the delivery apparatus 44 in embodiments.

Figure 49:
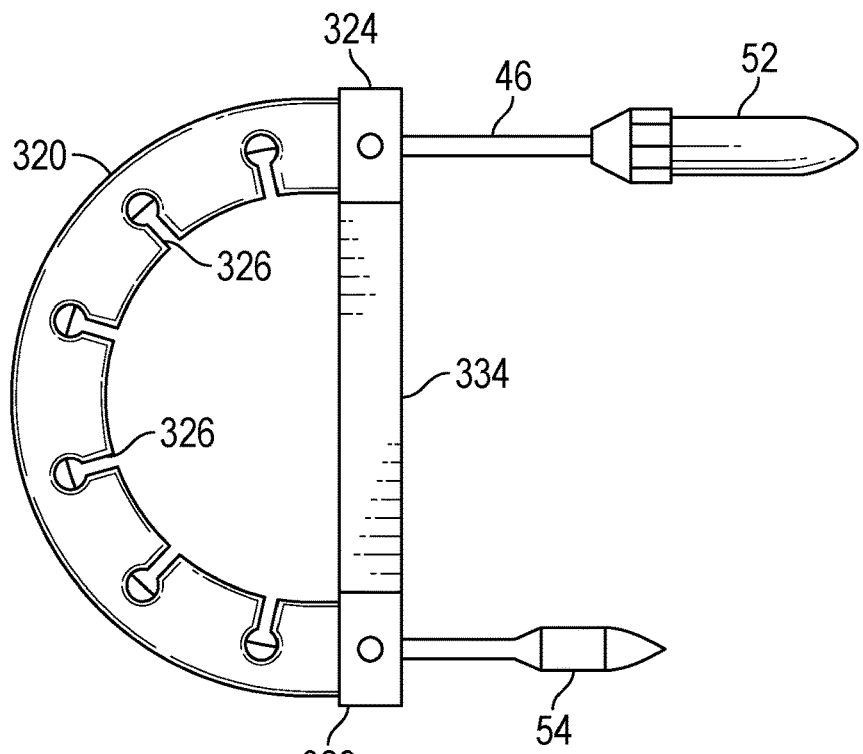
FIG. 49 illustrates the elongate body shown in FIG. 48 in a bent configuration according to an embodiment of the present disclosure.

The elongate body 320 may be utilized to assist the user in bending the elongate shaft 46 such that the distal end of the delivery apparatus 44 is proximate the proximal end of the delivery apparatus 44. The user may grasp the distal end 329 and/or the proximal end 324 of the elongate body 320 to draw the ends 324, 329 together. The elongate body 320 is bent in at least one plane to bend the elongate shaft of the delivery apparatus such that a distal portion of the delivery apparatus is positioned proximate a proximal portion of the delivery apparatus. The elongate body 320 may be moved from the straightened configuration shown in FIG. 48 to the bent or curved configuration as shown in FIG. 49. The size of the cut out portions 326 may decrease and the opposing surfaces 328 may contact each other. The elongate opening 332 (marked in FIG. 45) may close fully or partially to close the elongate shaft 46 within the channel 322. In embodiments, other devices or methods may be utilized to couple the elongate shaft 46 to the elongate body 320, such as the couplers shown in FIG. 46 or 47, among other forms of couplers.

The elongate body 320 may be retained in the bent or curved configuration by the coupler 334 extending between the ends 324, 329 of the elongate body 320. One or more couplers may be engaged between portions of the elongate body 320 to maintain a bent configuration of the elongate body 320. The coupler 334 may retain the elongate body 320 and the elongate shaft 46 in the bent or curved configuration.

In a bent or curved configuration, the user may be able to view the distal end of the delivery apparatus 44 while also manually operating the control mechanism at the handle 52. The proximity of the handle 52 to the distal end may allow for ease of operation at the distal end. A crimping operation, or other operation, may be performed at the distal end. For example, the distal end of the delivery apparatus 44 may be inserted into a channel 90 of a crimping device 84 and an implant 10 may be crimped to the implant retention area 54. The crimping procedure may comprise a crimping procedure as disclosed herein or another form of crimping procedure.

With the desired operation performed to the distal end of the delivery apparatus 44, the delivery apparatus 44 may be released from the elongate body 320. For example, the coupler 334 may be released and the elongate shaft 46 may be straightened. The elongate shaft 46 may then be removed from the channel 322 of the elongate body 320. The delivery apparatus 44 may then be prepared for insertion into a portion of a patient's body or may have another operation performed to the delivery apparatus 44.

The elongate body 320 may beneficially allow the ends of the delivery apparatus 44 to be efficiently brought in proximity to each other. The ends may be brought in proximity to allow an operation to be more efficiently performed to an end of the delivery apparatus. The elongate body 320 may be provided packaged on the elongate shaft 46 of the delivery apparatus 44 to allow for ease of packaging and delivery to a user. The elongate body 320 may be separated and discarded after use.

Figure 50:
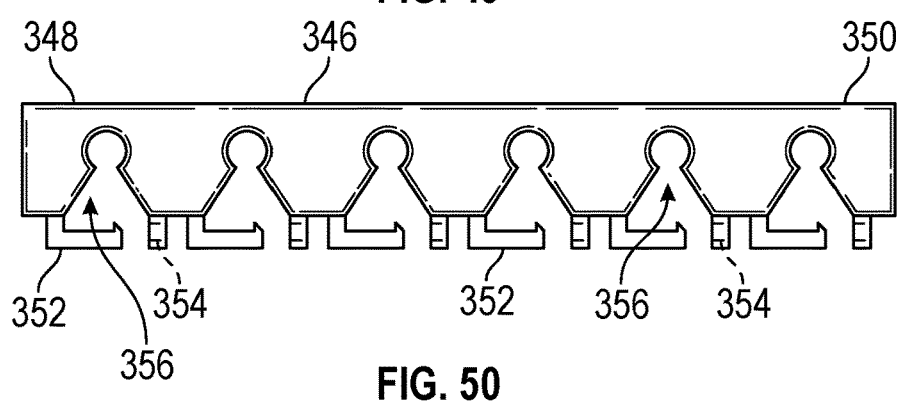
FIG. 50 illustrates a side view of a portion of an elongate body according to an embodiment of the present disclosure.
Figure 51:
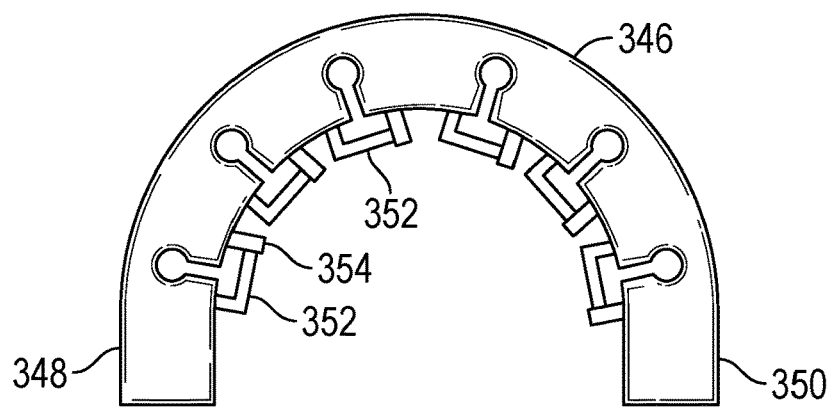
FIG. 51 illustrates a side view of a portion of an elongate body shown in FIG. 50 in a bent configuration.

FIG. 50 illustrates a variation of an elongate body 346 in which the coupler configured to retain the elongate body 346 in the bent configuration may comprise a plurality of couplers in the form of pins 352 configured to engage apertures 354. The pins 352 may be coupled to one side of a cut out portion 356 and the apertures 354 may be coupled to another side. The pins 352 may be configured to engage the apertures 354 in a ratcheting manner, in which the pins 352 include barbs or another structure configured such that the pins 352 may engage the apertures 354. As the elongate body 346 is moved to the bent or curved configuration, as shown in FIG. 51, the pins 352 may engage the apertures 354 to retain the elongate body 346 in the bent or curved configuration. Other configurations of couplers may be utilized as desired.

The elongate bodies may be utilized solely, or in combination with other components disclosed herein. The configuration of elongate body may be varied in embodiments.

Figure 57:
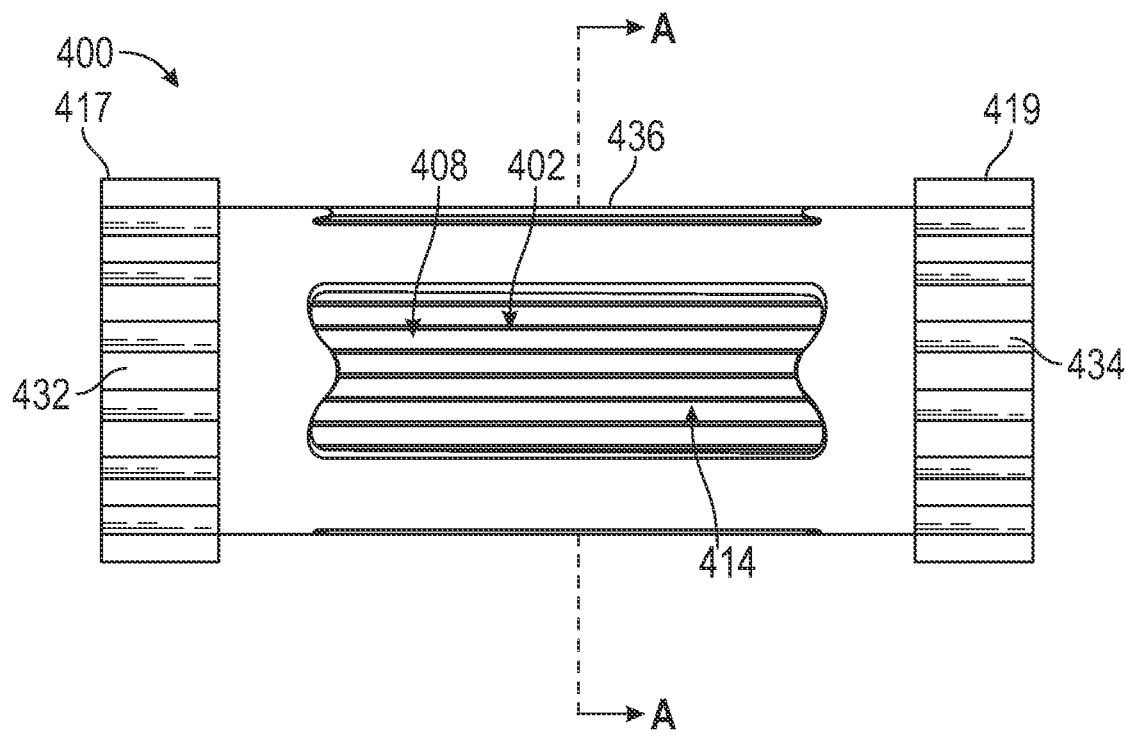
FIG. 57 illustrates a side view of a crimping device according to an embodiment of the present disclosure.

FIG. 57 illustrates a side view of a crimping system that may be utilized in embodiments herein. The crimping system may be for a prosthetic implant. The crimping system may utilize a crimping device 400 to crimp an implant according to embodiments herein.

Figure 58:
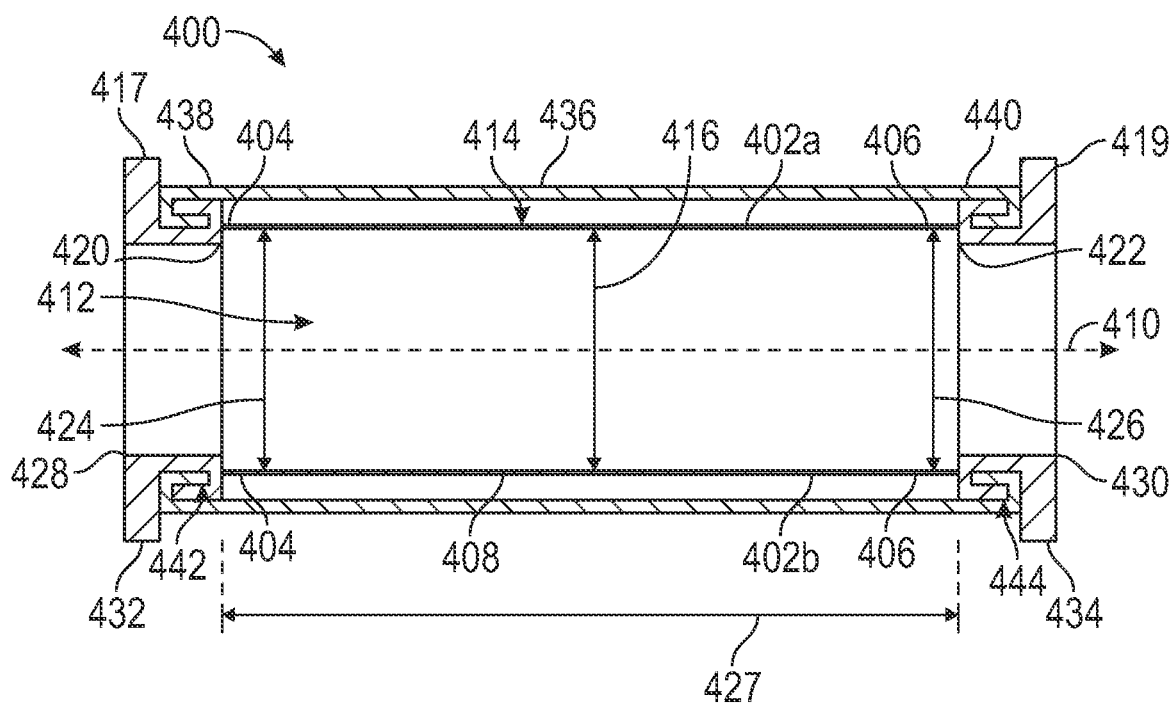
FIG. 58 illustrates a cross sectional schematic view of the crimping device shown in FIG. 57.

The crimping device 400 may include a plurality of elongate strands 402 each having a first end 404 (shown in the cross sectional view of FIG. 58) and a second end 406 (shown in the cross sectional view of FIG. 58). Referring to the cross sectional view of FIG. 58, the plurality of elongate strands 402 (with exemplary strands 402a, b marked in FIG. 58) may be arranged to form an elongate tube 408 extending around an axis 410 and surrounding a channel 412 configured to receive the implant and having a central portion 414 with an interior diameter 416.

In embodiments, the crimping device 400 may include a first support body 417 that may be coupled to the first end 404 of each of the plurality of elongate strands 402. The crimping device 400 may include a second support body 419 that may be coupled to the second end 406 of each of the plurality of elongate strands 402 and may be configured to rotate about the axis 410 relative to the first support body 417 to reduce the interior diameter 416 and compress the prosthetic implant within the channel 412.

Referring to FIG. 57, the elongate strands 402 may comprise string-like or wire-like bodies that each have a length that is greater than a diameter of the respective strand 402. The strands 402 may have circular cross sections or may be provided as flattened strips, or may have another configuration as desired.

Each of the strands 402 may be configured to be flexible in embodiments and in certain embodiments may be configured to stretch longitudinally. In embodiments, the strands 402 may be configured to stretch longitudinally, which may allow for rotation of the ends of the strands 402 relative to each other. The degree of stretch may be at least 5%, 7%, 10%, or a greater or lesser degree of stretch in embodiments as desired. The elongate strands 402 may each comprise a single strand body or a multi-strand body that may be configured to flex.

The elongate strands 402 may be made of a polymer material (such as nylon or other form of polymer) or may be made of a metal (such as stainless steel or nitinol or other metal as desired). The elongate strands 402 may be textured or provided with a friction coating to improve grip upon the implant in embodiments. In embodiments, the elongate strands 402 may be coated with a lubricious coating for example to minimize the possibility of damage to the implant, and to improve the ability of a portion of a delivery apparatus such as a sheath to contact and slide against the strands 402. In embodiments, other forms of elongate strands 402 may be utilized.

Figure 59:
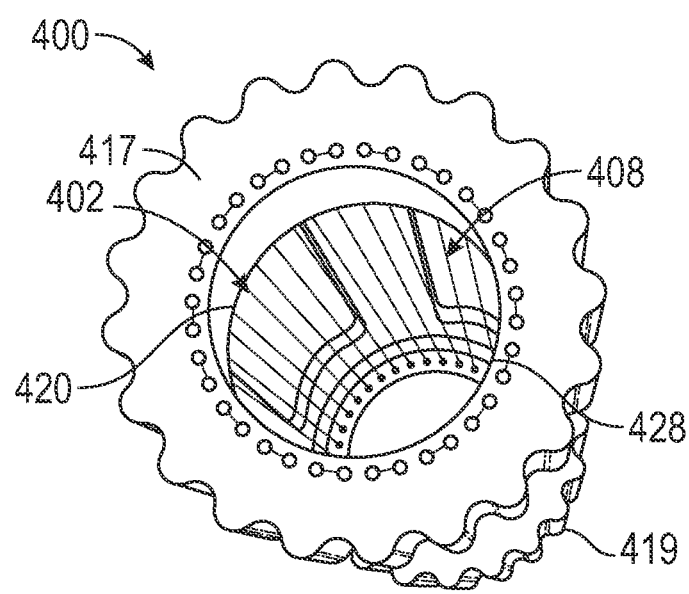
FIG. 59 illustrates a perspective end view of the crimping device shown in FIG. 57.

The plurality of elongate strands 402 may be arranged to form the elongate tube 408, with the plurality of elongate strands 402 circumferentially spaced from each other as shown in FIGS. 57 and 59. For example, the first ends 404 of the elongate strands 402 may each be coupled to a first support body 417 (as shown in FIG. 59) at a circumferential spacing from each other. The first ends 404 may be arranged in a ring. The spacing may be the same between the ends 404 of the elongate strands 402 or in embodiments the spacing may be different. The second ends 406 of the elongate strands 402 may each be coupled to a second support body 419 in a similar manner as is shown in FIG. 59 at the opposite end of the elongate strands 402. The second ends 406 may be arranged in a ring.

The arrangement of the respective ends 404, 406 of the elongate strands 402 may form the elongate tube 408 between the ends 404, 406. The elongate tube 408, for example, may have a cylindrical configuration as shown in FIGS. 57 and 59, or in embodiments may have another configuration such as a rectangular or triangular configuration.

The number of elongate strands 402 may vary in embodiments. As shown in FIGS. 57 and 59, the number of elongate strands may be thirty-six, although in embodiments a greater or lesser number may be utilized. For example, the number of elongate strands may be ten or greater, twenty or greater, thirty or greater, or a greater or lesser amount as desired. The number of elongate strands may be greater than fifty in embodiments.

Referring to FIG. 58, the first ends 404 of the plurality of elongate strands 402 may be arranged to form an opening 420 for the channel 412. The second ends 406 of the plurality of elongate strands 402 in embodiments may further be arranged to form an opening 422 for the channel 412. One or more of the openings 420, 422 may allow an object such as the prosthetic implant to be passed through and into the channel 412 for crimping.

Figure 65:
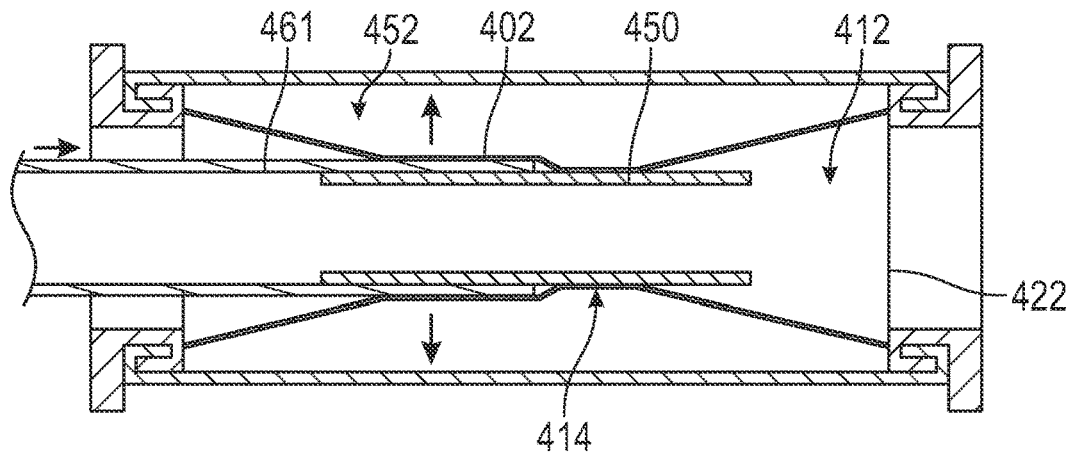
FIG. 65 illustrates a cross sectional schematic view of the crimping device shown in FIG. 57 with a capsule extending over the crimped prosthetic implant.

The first ends 404 of the plurality of elongate strands 402 may further be arranged to have a diameter 424. The diameter 424 may comprise the diameter of the opening 420 in embodiments. The second ends 406 of the plurality of elongate strands 402 in embodiments may further be arranged to have a diameter 426. The diameter 426 may comprise the diameter of the opening 422 in embodiments. One or more of the diameters 424, 426 in embodiments may be configured to be less than the length 427 of the elongate tube 408. As such, the elongate strands 402 may form an elongate structure that may be configured to accommodate elongate implants, as well as providing the ability for an elongate sheath (as shown in FIG. 65) to enter into the channel 412 and capture the crimped implant. The proportion of the diameters 424, 426 to the length 427 of the elongate tube 408 may provide improved crimping and capture of the crimped implant in the crimping process. The relative proportions of the elongate tube 408 may be varied from the proportions shown herein in embodiments.

The support bodies 417, 419 may be positioned at the ends 404, 406 of the plurality of elongate strands 402. One or more of the support bodies 417, 419 may include a respective opening 428, 430 that may lead to the respective openings 420, 422 of the plurality of elongate strands 402. In embodiments, the support bodies 417, 419 may have a variety of forms, including ring bodies as shown in FIGS. 57-60 or other configurations such as lever arms or mechanical actuators, or other configurations as desired. The support bodies 417, 419 may include respective grip portions 432, 434 that may allow for grip of the support bodies 417, 419 during use. The grip portions 432, 434 may be gripped to allow for rotation of the support bodies 417, 419 relative to each other as desired. The grip may comprise a manual grip in embodiments. For example, a user may grasp one or more of the grip portions 432, 434 and rotate one or more of the support bodies 417, 419 relative to each other. In embodiments, grip may be provided with a tool.

In embodiments, a retainer body 436 may be coupled to the first support body 417 and the second support body 419. The retainer body 436 may comprise a central body positioned between the first support body 417 and the second support body 419. The retainer body 436 may define a distance (corresponding the length 427 shown in FIG. 58) between the first support body 417 and the second support body 419. The retainer body 436 may comprise a housing that retains the components of the crimping device 400 together. The retainer body 436 may include a plurality of openings as shown in FIGS. 57 and 59 that may allow for view of the interior of the retainer body 436.

The retainer body 436 may have a first portion 438 coupled to the first support body 417 and a second portion 440 coupled to the second support body 419. The retainer body 436 may comprise a tube with an internal cavity for retaining the plurality of elongate strands 402 therein in embodiments, or may have another configuration as desired.

Figure 66:
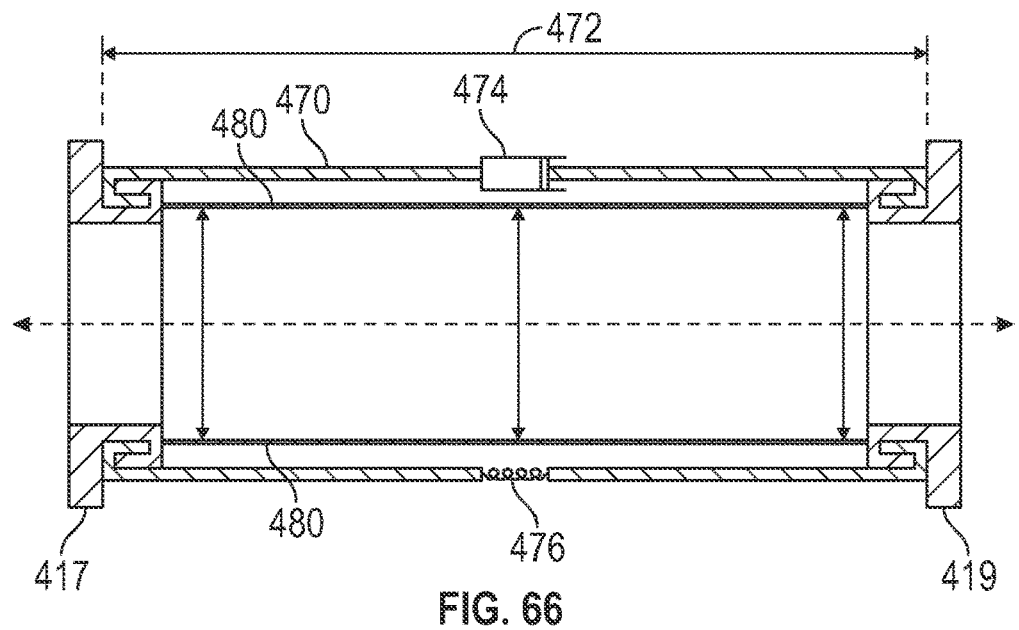
FIG. 66 illustrates a cross sectional view of a crimping device according to an embodiment of the present disclosure.

In embodiments, the retainer body 436 may define a static distance between the first support body 417 and the second support body 419. For example, as shown in FIGS. 57-59, the retainer body 436 may be rigid and thus may maintain the relative positions of the first support body 417 and the second support body 419. In embodiments such as shown in FIG. 66, a retainer body may have a length that varies to provide a variable distance between the first support body and the second support body.

One or more of the first support body 417 or the second support body 419 may be configured to rotate relative to the retainer body 436. For example, as shown in FIG. 58, the first support body 417 and second support body 419 may couple to the retainer body 436 with a respective rotation coupler 442, 444 that may allow for rotation about the axis 410. For example, each rotation coupler 442, 444 may include a bearing surface that allows for rotation. The retainer body 436 may maintain a distance between the first support body 417 and the second support body 419 during rotation in embodiments. In embodiments, one of the first support body 417 or the second support body 419 may be configured to rotate relative to the retainer body 436 while the other support body remains fixed in position relative to the retainer body 436. Thus, a user may only rotate one of the support bodies 417, 419 in such an embodiment. Various other configurations of retainer bodies may be utilized as desired.

Figure 60:
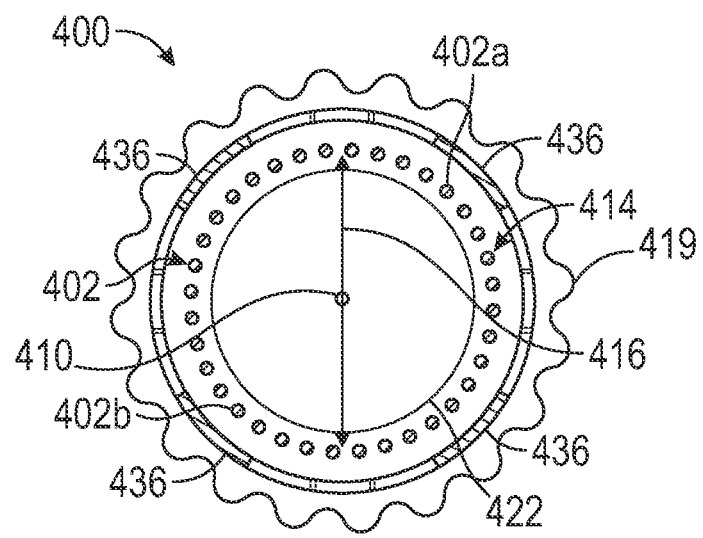
FIG. 60 illustrates a cross sectional schematic view of the crimping device along line A-A in FIG. 57.

The plurality of elongate strands 402 may be configured to rotate from an expanded configuration to a reduced diameter configuration. An expanded configuration may be shown in FIGS. 57-62. In an expanded configuration, the channel 412 may be available for an implant to be inserted therein. In an expanded configuration, as shown in FIGS. 57-60, each of the first ends 404 of the elongate strands 402 may be aligned circumferentially with a respective one of the second ends 406 of the elongate strands 402. FIG. 59, for example, illustrates such an arrangement. The elongate strands 402 may extend parallel with the axis 410. FIG. 60 comprises a cross sectional view of the crimping device 400 along line A-A in FIG. 57. The elongate strands 402 are shown to extend parallel with the axis 410.

Referring to FIG. 58, in an expanded configuration, the interior diameter 416 of the central portion 414 of the elongate tube 408 may be at a maximum. The interior diameter 416 of the central portion 414 may be the same as the diameters 424, 426 of the ends 404, 406 of the strands 402. In embodiments, an expanded configuration may include some rotation of the first ends 404 of the elongate strands 402 relative to the second ends 406. For example, FIG. 61 illustrates an expanded configuration with some rotation of the first ends 404 of the elongate strands 402 relative to the second ends 406.

In the expanded configuration, the implant may be inserted into the channel 412. FIG. 61, for example, illustrates an implant 450 (with a frame of the implant 450 shown and other features of the implant 450 excluded from view for clarity) positioned within the channel 412. The implant 450 may preferably be positioned at the central portion 414 of the elongate tube 408.

Figure 61:
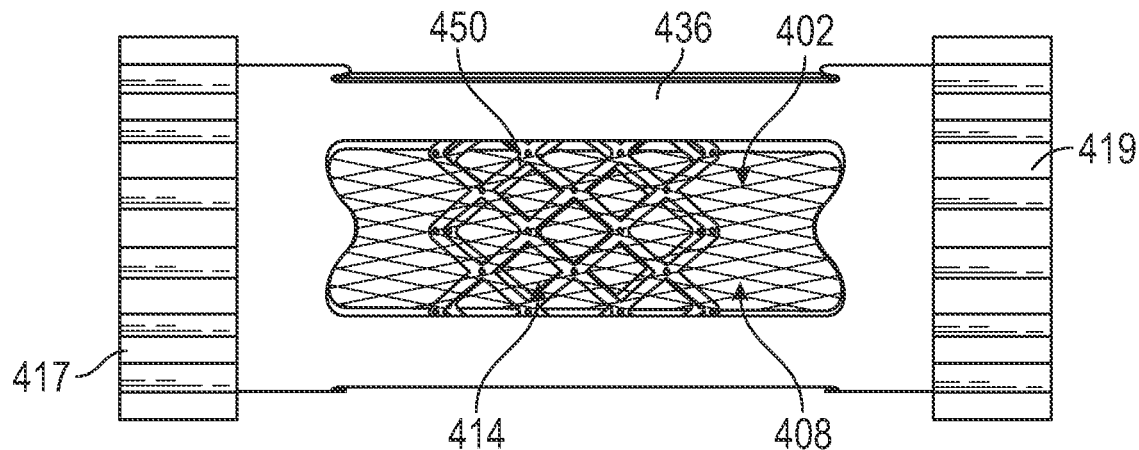
FIG. 61 illustrates the crimping device shown in FIG. 57 with a prosthetic implant positioned therein.
Figure 62:
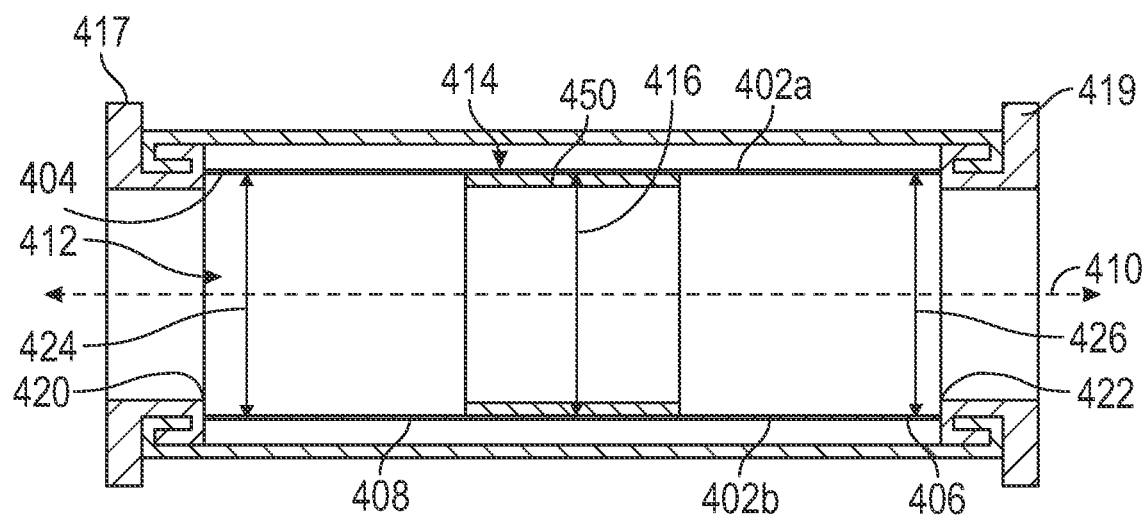
FIG. 62 illustrates a cross sectional schematic view of the crimping device shown in FIG. 57 with a prosthetic implant positioned therein.

FIG. 62 illustrates a cross sectional view of the implant 450 positioned within the channel 412. The implant 450 may be aligned axially within the channel 412 as shown in FIGS. 61 and 62. In embodiments, the implant 450 may be inserted into the channel 412 through one of the openings 420, 422 of the plurality of elongate strands 402, and may be inserted through one of the openings 428, 430 of the support bodies 417, 419. In embodiments in which the implant 450 is to be positioned on a portion of a delivery apparatus, such as a balloon expandable implant, a portion of the delivery apparatus may extend through the channel 412 from one opening 422 to another opening 420 as desired. The openings 420, 422 of the channel 412 accordingly may allow for an elongate shaft of a delivery apparatus, as may be disclosed herein, to pass therethrough if desired. An elongate shaft of a delivery apparatus is excluded from view in FIGS. 61 and 62.

In the configuration shown in FIGS. 61 and 62, one or more of the support bodies 417, 419 may be rotated relative to each other to rotate the plurality of elongate strands 402. The second support body 419 may be rotated about the axis 410 relative to the first support body 417 to reduce the interior diameter 416 and compress the implant 450 within the channel 412. The plurality of elongate strands 402 may be rotated to the reduced diameter configuration. The ends 404, 406 of the plurality of elongate strands 402 may be rotated relative to each other. The plurality of elongate strands 402 may be twisted in the reduced diameter configuration.

Figure 63:
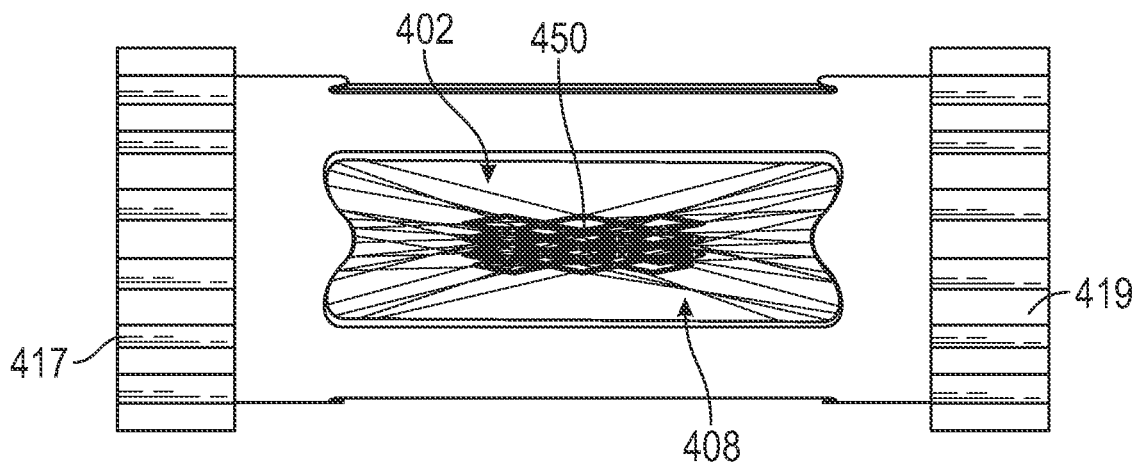
FIG. 63 illustrates a side view of the crimping device shown in FIG. 57 with a prosthetic implant crimped.
Figure 64:
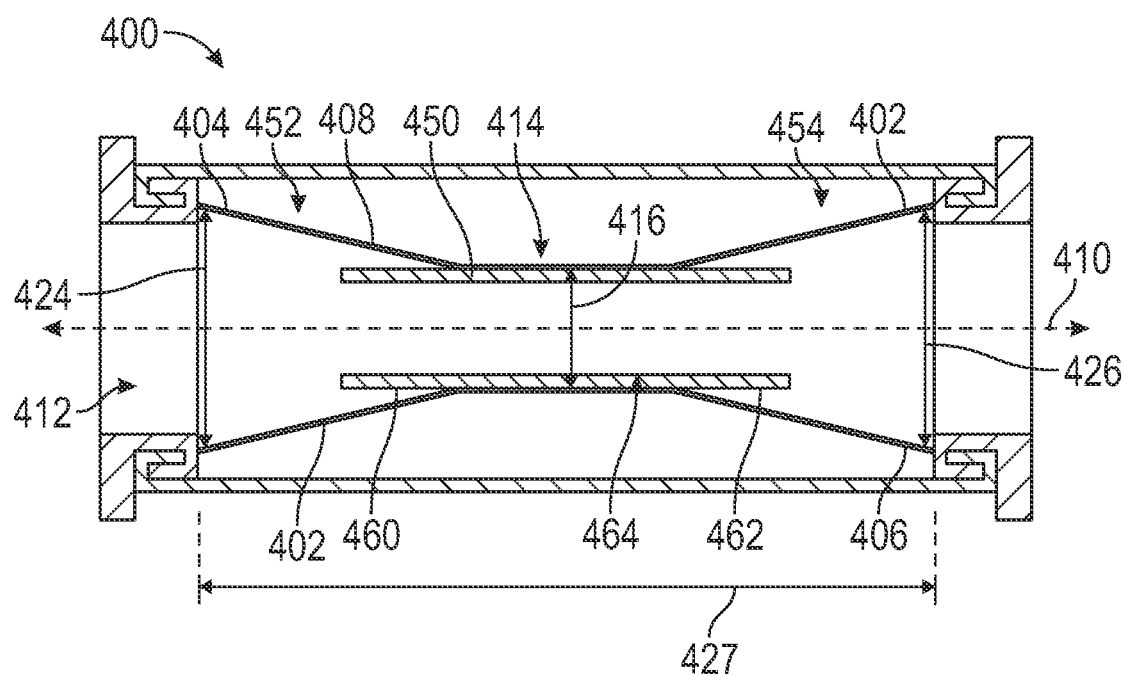
FIG. 64 illustrates a cross sectional view of the crimping device shown in FIG. 57 with a prosthetic implant crimped.

FIGS. 63 and 64, for example, illustrate the plurality of elongate strands 402 in the reduced diameter configuration. The plurality of elongate strands 402 and the elongate tube 408 have formed a hyperboloid or hourglass shape with the interior diameter 416 having reduced and the respective diameter 424 at the first end 404 and the diameter 426 at the second end 406 being greater than the interior diameter 416.

Each of the plurality of elongate strands 402 may have the circumferential position of the first end 404 rotate relative to the second end 406 to cause each strand to rotate about the axis 410 and extend transverse relative to the axis 410. The strands 402 may each stretch longitudinally to allow for the circumferential position of the first end 404 to rotate relative to the second end 406 in light of the length 427 of the elongate tube 408 remaining constant as shown in FIG. 64.

FIG. 64 illustrates a schematic cross sectional view of the crimping device 400, with a profile of the strands 402 illustrated and individual strands not illustrated. As shown in FIG. 64, the plurality of elongate strands 402 may form a first funnel 452 extending radially outward from the central portion 414 toward the first ends 404 of the plurality of elongate strands 402 when the plurality of elongate strands 402 are in the reduced diameter configuration. The plurality of elongate strands 402 may form a second funnel 454 extending radially outward from the central portion 414 toward the second ends 406 of the plurality of elongate strands 402 when the plurality of elongate strands 402 are in the reduced diameter configuration. Each funnel may have a conical frustum shape, with the wide portion directed away from the central portion 414 of the elongate tube 408 and the narrow portion at the central portion 414. Other configurations of funnels may result as desired.

The central portion 414 may apply a compressive force to the implant 450 due to the plurality of elongate strands 402 contacting the implant 450 and pressing radially inward against the implant 450. The central portion 414 accordingly may crimp the implant 450. The central portion 414 may have a cylindrical shape positioned between the funnels 452, 454 caused by the implant 450 deflecting the elongate strands 402 at the central portion 414.

In embodiments, the implant 450 may be configured to elongate and be axially lengthened in response to the radially compressive force applied to the implant 450 by the plurality of elongate strands 402. The diameter of the implant, for example, may decrease, with the length of the implant correspondingly increasing. The implant 450 shown in FIGS. 63 and 64, for example, has increased in length. End portions 460, 462 of the implant 450 in embodiments may remain within the channel 412 and may be positioned within respective funnels 452, 454.

In embodiments, the implant 450 may be crimped to an elongate shaft of a delivery apparatus in the configuration shown in FIG. 64. For example, the elongate shaft of the delivery apparatus may pass through the channel 412 and the implant may be crimped to the elongate shaft (e.g., a balloon inflatable implant may be crimped to an inflatable balloon). The implant 450 may be crimped to an implant retention area of the elongate shaft. In embodiments however, in the configuration shown in FIG. 64, a portion of a delivery apparatus may be inserted into the channel 412 to couple to and extend over the crimped implant 450.

FIG. 65, for example, illustrates a sheath 461 of a delivery apparatus may be inserted into the channel 412 and passed over the implant 450 compressed within the channel 412. In embodiments, the sheath 461 may comprise a capsule for retaining the implant 450 prior to deployment of the implant 450. The capsule for example, may cover the implant 450 during delivery of the implant 450, and may comprise an implant retention area of the delivery apparatus. In embodiments, other forms of sheaths may be utilized to capture the implant, such as loaders for loading the implant into a delivery apparatus or other device.

The plurality of elongate strands 402 may stretch radially outward from the central portion 414 when the plurality of elongate strands are in the reduced diameter configuration and the sheath passes over the implant 450 (as marked by the arrows pointing radially outward in FIG. 65). The strands 402 may stretch radially outward from the central portion 414 to allow the sheath 461 to extend over the outer surface of the implant 450 when the plurality of elongate strands are in the reduced diameter configuration. The sheath 461 may contact the strands 402 and press the strands 402 radially outward. The sheath 461 may slide between the strands 402 and the outer surface of the implant 450.

The sheath 461 may extend over the entirety of the crimped implant 450 to capture the implant 450, and may then be removed and retracted from the channel 412 with the implant 450 positioned therein. As such, the implant 450 may be captured with a sheath 461 in the crimped state in a single crimping operation. Other features of the delivery apparatus such as a guide wire shaft or nose cone may pass through the channel 412 and possibly out of the opening 422 in embodiments if desired.

The funnel 452 formed by the plurality of elongate strands 402 may be configured to receive the sheath 461 of the delivery apparatus for extending over the prosthetic implant. The funnel 452 may guide the sheath 461 to capture the implant 450. For example, the funnel 452 may deflect and orient the sheath 461 towards the implant 450 to improve each of capture of the crimped implant 450.

Figure 68A:
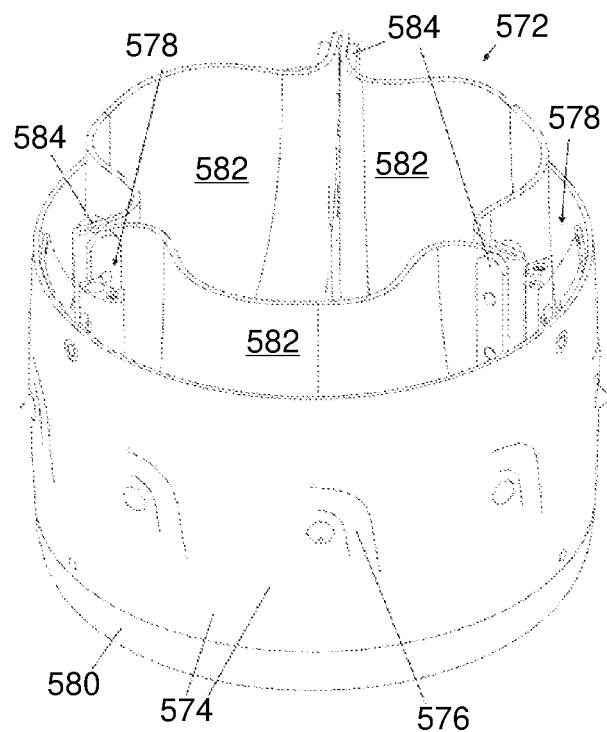
FIGS. 68A-C illustrates perspective views of a prosthetic implant according to an embodiment of the present disclosure.
Figure 68B:
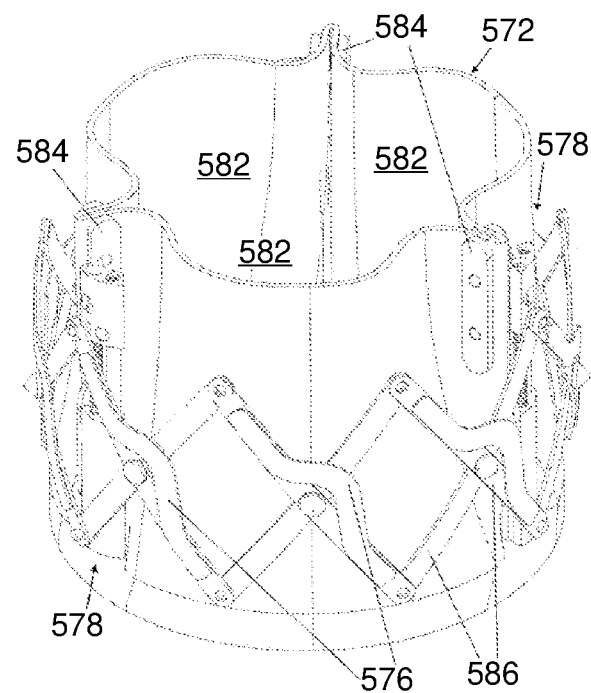
Figure 68C:
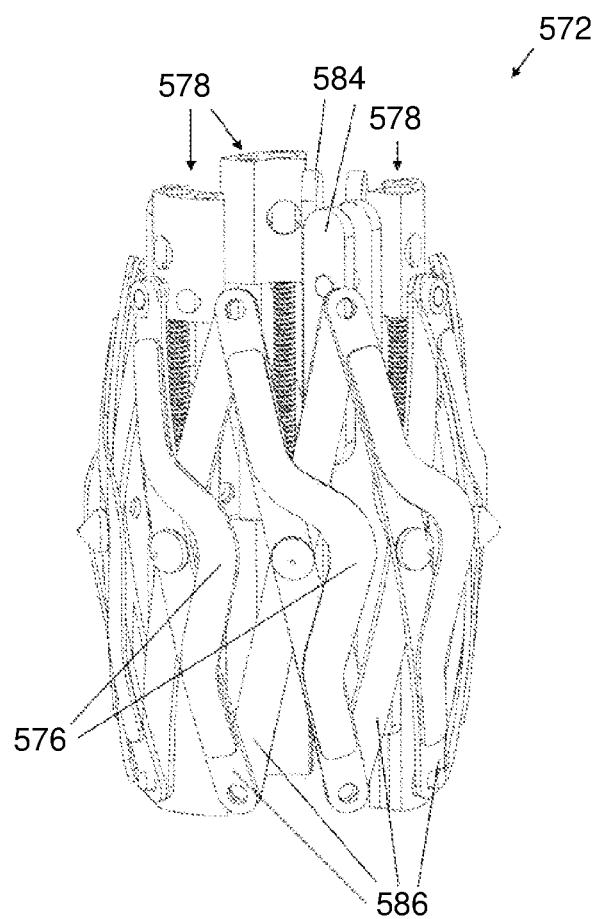

In embodiments, the implant 450 may include a mechanical frame that may have a plurality of struts connected by rotatable hinges. The implant 450 may comprise a mechanically expandable implant. FIGS. 68A-68C, for example, illustrate an exemplary configuration of an implant having a mechanical frame. An implant with a mechanical frame may expand due to operation of a mechanical assembly. An example of such an implant is disclosed in U.S. Pat. No. 9,913,716, filed Jan. 24, 2017 and issued Mar. 13, 2018, the entire contents of which are incorporated herein. FIGS. 72, 77, and 81 of U.S. Pat. No. 9,913,716 are reproduced here as FIGS. 68A-68C. The implant may include a prosthetic replacement heart valve assembly 572, a stent lattice 574, graft enclosures 576, jack assemblies 578, graft material 580, valve leaflets 582, and commissure plates 584. The frame may include a plurality of struts. A cover is removed in FIG. 68B to show the plurality of struts 586. The plurality of struts 586 may be connected by rotatable hinges. FIG. 68C illustrates the implant with the cover removed, and in a compressed state. The crimping device disclosed herein may be utilized to move the implant to a compressed state as shown in FIG. 68C. A mechanical assembly may then be utilized to expand the implant at a desired location within the patient's body.

The use of a mechanical frame may allow the entirety of the frame to crimp due to a compression of a single portion or mid portion of the implant. For example, referring to FIG. 64, end portions 460, 462 of the implant 450 may protrude from the central portion 414 and may be in a compressed state due to a mid portion 464 having been compressed by the plurality of elongate strands 402. As such, a compressive force need only be applied to a portion of the implant 450 to produce a crimped state for the entirety of the implant 450. The protruding end portions 460, 462 of the implant 450 may allow for ease of capture by a portion of a delivery apparatus such as the sheath 461 shown in FIG. 65. The implant 450 may be configured to have a length increase in response to a radial compression of the implant 450.

In embodiments, other forms of implants may be utilized and crimped, including self-expandable implants, balloon expandable implants, and other forms of expandable implants. The implants crimped with the crimping device 400 may comprise implants that may be biased to expand upon the compressive force of the crimping device being removed. For example, a mechanically expandable implant may expand upon the compressive force being removed, which may render it difficult to capture such an implant in a sheath of a delivery apparatus. As such, these implants may beneficially remain in a compressed state when a sheath captures them as shown in FIG. 65 for example. The compressive force against the implants, for example, may remain during capture of the implants, to reduce the possibility of the implants radially expanding outward. A simplified crimping and capture process may result. In embodiments, other forms of implants may be utilized in embodiments herein. The implants utilized may be for deployment to an aortic valve, a mitral valve, a tricuspid valve, or a pulmonary valve, among other deployment sites. The implant may comprise replacement heart valves in embodiments. The implants may include leaflets and other components such as one or more skirts as disclosed herein. Other forms of implants may be utilized as desired In embodiments, an insert may be utilized that may have a mechanical frame similar to the frame of the implant 450. The insert, for example, may include a plurality of struts connected by rotatable hinges. The insert may be configured to crimp due to a compression of a single portion or mid portion of the insert. The insert may be configured to receive the prosthetic implant within the insert. The implant, for example, may comprise a self-expandable or balloon expandable implant, which may have a plastically deformable frame. The insert may have the implant positioned therein. The insert, with the implant positioned therein, may be positioned within the channel 412 and crimped with the crimping device 400. As such, a central force applied to a single portion of the insert by the crimping device 400 may result in the entire insert being crimped. The insert may radially compress the implant and thus the entire implant may be crimped along its length.

Variations in the crimping device 400 may be provided. FIG. 66, for example, illustrates an embodiment in which the retainer body 470 is configured to have a length 472 that varies to provide a variable distance between the first support body 417 and the second support body 419. The retainer body 470 for example, may include a length varying body such as a piston 474 and/or a spring 476 to allow the length 472 to vary. The plurality of elongate strands 480 in such an embodiment may have a fixed length and may be non-stretchable. The distance between the support bodies 417, 419 may vary to allow the plurality of elongate strands 480 to rotate upon relative rotation of the support bodies 417, 419. Other forms of length varying bodies or combinations of length varying bodies may be utilized as desired.

Figure 67:
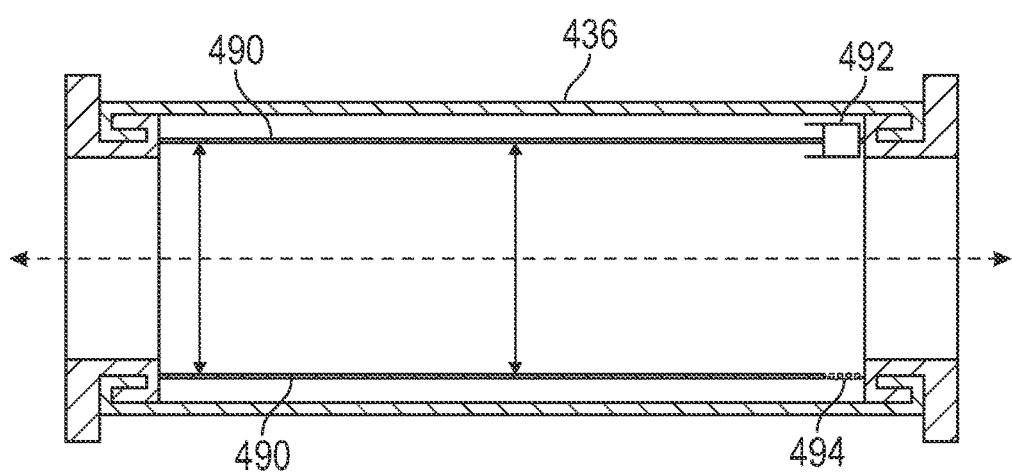
FIG. 67 illustrates a cross sectional view of a crimping device according to an embodiment of the present disclosure.

FIG. 67 illustrates an embodiment in which a length varying body comprises a portion of the elongate strands 490. The length varying body may comprise a body such as a piston 492 or a spring 494 to allow the length of the elongate strands 490 to vary. A first portion of the elongate strands accordingly may be stretchable and a second portion may be non-stretchable in such an embodiment. The length of the retainer body 436 may remain constant.

In embodiments, in manufacture, the plurality of elongate strands may be formed and coupled to the support bodies in separate steps. In embodiments, the plurality of elongate strands may be formed integral with the first support body and/or the second support body. For example, the support bodies and the plurality of elongate strands may be formed in a mold such as a single mold and may be integral with each other. Injection molding may be utilized. As such, reduced manufacturing complexity may result. Various other methods of manufacture may be utilized as desired.

The crimping systems and devices disclosed herein may be utilized solely or in combination with other embodiments disclosed herein.

The crimped or otherwise prepared implants and devices may be utilized for treatment to a portion of a patient's body. Such treatment may include implantation of the implant, among other procedures.

As discussed, various forms of implants may be utilized with the embodiments disclosed herein, including prosthetic heart valves, or other forms of implants, such as stents or filters, or diagnostic devices, among others. The implants may be expandable implants configured to move from a compressed or undeployed state to an expanded or deployed state. The implants may be compressible implants configured to be compressed inward to have a reduced outer profile and to move the implant to the compressed or undeployed state. A crimping device as disclosed herein may assist in moving the implant to the compressed or undeployed state.

The delivery apparatuses as disclosed herein may be utilized for aortic, mitral, tricuspid, and pulmonary replacement and repair as well. The delivery apparatuses may comprise delivery apparatuses for delivery of other forms of implants, such as stents or filters, or diagnostic devices, among others.

The delivery apparatuses and the systems disclosed herein may be used in transcatheter aortic valve implantation (TAVI) or replacement of other native heart valves (e.g., mitral, tricuspid, or pulmonary). The delivery apparatuses and the systems disclosed herein may be utilized for transarterial access, including transfemoral access, to a patient's heart. The delivery apparatuses and systems may be utilized in transcatheter percutaneous procedures, including transarterial procedures, which may be transfemoral or transjugular. Transapical procedures, among others, may also be utilized. Other procedures may be utilized as desired.

Features of embodiments may be modified, substituted, excluded, or combined across embodiments as desired.

In addition, the methods herein are not limited to the methods specifically described, and may include methods of utilizing the systems and apparatuses disclosed herein. The steps of the methods may be modified, excluded, or added to, with systems, apparatuses, and methods disclosed herein.

The features of the embodiments disclosed herein may be implemented independently of the crimping devices, or independent of other components disclosed herein. The various apparatuses of the system may be implemented independently.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A support body for a prosthetic heart valve, comprising:
   a first portion comprising an alignment device configured to couple with a crimping device;

a second portion comprising a support surface that tapers from a wider end disposed adjacent the first portion to a narrower end, wherein the support surface is configured to receive the prosthetic heart valve thereon and hold one or more leaflets of the prosthetic heart valve in an open position; and a central channel extending through the first portion and the second portion, the central channel configured to receive a delivery apparatus for the prosthetic heart valve therethrough.

2. The support body of claim 1, wherein the alignment device is an axially extending protrusion that extends from a first end of the first portion toward a second end of the first portion that is disposed adjacent to the second portion.

3. The support body of claim 1, wherein the first portion has a cylindrical outer surface, and wherein the alignment device extends outward from the cylindrical outer surface.

4. The support body of claim 3, wherein a second end of the first portion comprises a proximally facing surface that extends perpendicular to the cylindrical outer surface and radially inward toward the wider end of the support surface.

5. The support body of claim 4, wherein the proximally facing surface joins the first portion to the second portion and includes a recess therein configured to receive a coupler of a ring body, the ring body configured to rotationally align the prosthetic heart valve on the support surface.

6. The support body of claim 1, wherein the second portion comprises a connector portion adjacent to the first portion, the connector portion having a cylindrical shape with a diameter that is smaller than a diameter of the wider end of the support surface.

\* \* \* \* \*